United States Patent
Böhm et al.

(10) Patent No.: US 9,545,436 B2
(45) Date of Patent: *Jan. 17, 2017

(54) METHODS FOR TREATING BLEEDING DISORDERS USING A PLATELET SUBPOPULATION

(71) Applicants: BAXALTA INCORPORATED, Bannockburn, IL (US); BAXALTA GMBH, Glattpark (Opfikon) (CH)

(72) Inventors: Ernst Böhm, Vienna (AT); Michael Dockal, Vienna (AT); Andrea Sedivy, Vienna (AT)

(73) Assignees: BAXALTA GMBH (CH); BAXALTA INCORPORATED, Bannockburn (IL)

( * ) Notice: Subject to any disclaimer, the term of this patent is extended or adjusted under 35 U.S.C. 154(b) by 13 days.

This patent is subject to a terminal disclaimer.

(21) Appl. No.: 14/211,978

(22) Filed: Mar. 14, 2014

(65) Prior Publication Data

US 2014/0294794 A1    Oct. 2, 2014

Related U.S. Application Data

(60) Provisional application No. 61/799,875, filed on Mar. 15, 2013.

(51) Int. Cl.
| | | |
|---|---|---|
| *A01N 63/00* | (2006.01) | |
| *A61K 38/48* | (2006.01) | |
| *A61K 35/19* | (2015.01) | |
| *A61K 45/06* | (2006.01) | |
| *G01N 33/86* | (2006.01) | |
| *C12N 5/078* | (2010.01) | |

(52) U.S. Cl.
CPC ........... *A61K 38/4846* (2013.01); *A61K 35/19* (2013.01); *A61K 45/06* (2013.01); *C12N 5/0644* (2013.01); *G01N 33/86* (2013.01); *C12Y 304/21021* (2013.01); *G01N 2333/96447* (2013.01); *G01N 2800/52* (2013.01)

(58) Field of Classification Search
CPC .... A61K 45/06; A61K 38/4846; A61K 35/19; G01N 33/89; G01N 2800/52; G01N 2333/96447; C12N 5/0644; C12Y 304/21021
See application file for complete search history.

(56) References Cited

U.S. PATENT DOCUMENTS 4,784,950 A    11/1988    Hagen et al.

FOREIGN PATENT DOCUMENTS

| EP | 1952822 A1 | 8/2008 |
| WO | WO-2006/020773 A2 | 2/2006 |

OTHER PUBLICATIONS

Fenger-Eriksen et al. (2009) Ann. Hematol. (2009) 88(3): 255-260.*
Carr et al. Thromb. Haemost. (2003) 89(5): 803-811.*
Schulman et al. Haemophilia (2006) 12(3): 223-227.*
Livnat et al. Haemophilia (2008) 14: 782-786.*
Poon Current Op. Hematol. (2001) 8: 312-318.*
Rowe et al. Am. J. Health-Sys. Pharm. (2010) 67: 361-365.*
Salcioglu et al. Blood Coag. Fibrinolysis (2013) 24: 854-861.*
Midathada et al. Am. J. Clin. Pathol. (2004) 121: 124-137.*
Johansson et al. British J. Haematology (2008) 143: 559-569.*
Abshire et al., Recombinant factor VIIa: review of efficacy, dosing regimens and safety in patients with congenital and acquired factor VIII or IX inhibitors. *J. Thromb. Haemost.* 2(6): 899-909 (2004).
Bouchard et al., Measurement of procoagulant platelet subpopulations in whole blood: Development of an assay for population-based studies. *Thromb. Res.* 127(1): 62-4 (2011).
Dale, Coated-platelets: an emerging component of the procoagulant response. *J. Thromb. Haemost.* (10): 2185-92 (2005).
Franchini et al., Past, present and future of hemophilia: A narrative review.*Orphan. J. Rare Dis.* 7(1): 24 (2012).
Harrison et al., Clinical Tests of Platelet Function, Platelets, 3rd Edition, Chapter 26, pp. 519-545 (2013).
Hedner et al., Potential role for rFVIIa in transfusion medicine. *Transfusion*, 42(1): 114-24 (2002).
Heemskerk et al., Platelet-based coagulation: Different populations, different functions. *J. Thromb. Haemost.* 11: 2-16 (2013).
Hoffman et al., Mechanisms and monitoring of bypassing agent therapy. *J. Thromb. Haemost.* 10: 1478-85 (2012).
Hoffman, FVIIa: You've come a long way, baby! *Blood*, 112: 3002-3 (2008).
Kjalke et al., Preferential localization of recombinant factor VIIa to platelets activated with a combination of thrombin and a glycoprotein VI receptor agonist. *J. Thromb. Haemost.* (5): 77480 (2007).
Koehn et al., Binding of recombinant activated factor VII (rFVIIIa) to human platelets identifies donor variation and platelet subpopulations with increased binding of rFVIIa in platelet concentrations. *Blood*, 122(21): 3565 (2013).
Lopez-Vilchez et al., Redistribution and hemostatic action of recombinant activated factor VII associate with platelets. *Am. J. Pathol.* 178(6): 2938-48 (2011).
Ng et al., Recombinant activated clotting factor VII (rFVIIa) in the treatment of surgical and spontaneous bleeding episodes in hemophilic patients. *Vasc Health Risk Manag.* 2(4): 433-40 (2006).
NovoSeven RT Coagulation Factor VIIa (Recombinant) Room Temperature Stable, Lyophilized Powder product label, revised Jan. 2010 (1999).
Ratko et al., Off-label use of recombinant activated factor VII (NovoSeven®). *P & T*, 29(11): 712-20 (2004).
Stroncek et al., Platelet transfusions, *Lancet*, 370(9585): 427-38 (2007).
Sweeney et al., Quality of platelet concentrates, *Immunol. invest.* 24(1&2): 353-70 (1995).
International Search Report and Written Opinion of the International Searching Authority for International Application No. PCT/US2014/028865, dated Aug. 13, 2014.

* cited by examiner

*Primary Examiner* — Susan Hanley
(74) *Attorney, Agent, or Firm* — Troutman Sanders LLP

(57) ABSTRACT

The present invention relates to a platelet subpopulation with high binding capacity to recombinant activated factor VII (rFVIIa), and its use for the treatment of bleeding disorders and for determining whether a subject is a candidate for treatment with rFVIIa.

26 Claims, 17 Drawing Sheets

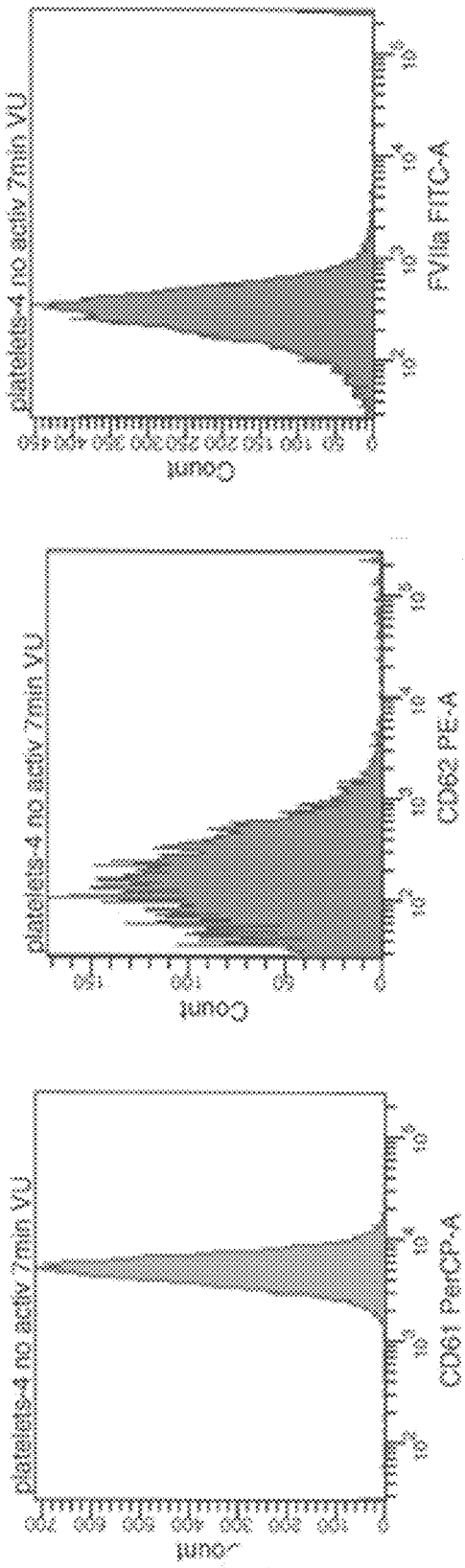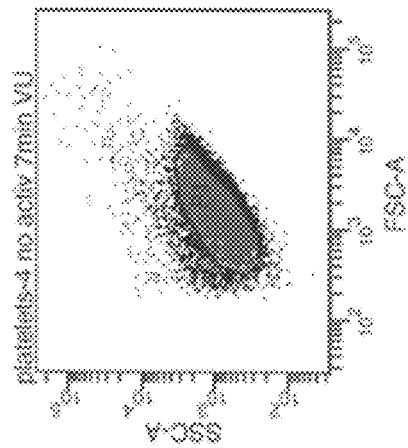
FIGURE 1A

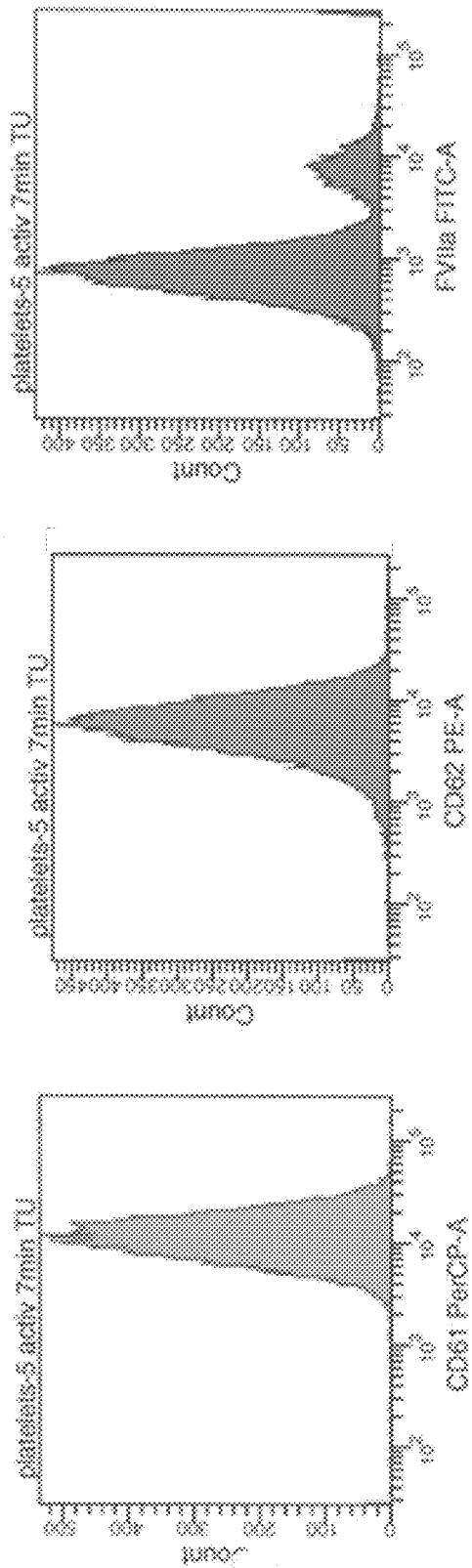
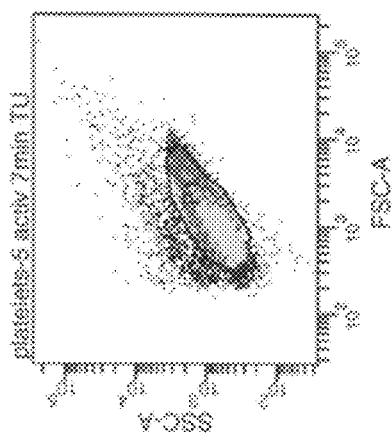
FIGURE 2A

FIGURE 6A-B

METHODS FOR TREATING BLEEDING DISORDERS USING A PLATELET SUBPOPULATION

All patents, patent applications and publications, and non-patent publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

The body can engage in blood clotting through the "extrinsic pathway" and the "intrinsic pathway." Clotting factors mediate the clotting response in both pathways. Both pathways are activated by different stimuli and ultimately feed into a common machinery. In the extrinsic pathway, when vascular injury occurs, a subendothelial cell-surface glycoprotein called "Tissue Factor" (TF) (also known as Factor III) is released at the site of injury triggering blood coagulation in healthy individuals. Tissue factor is found on the outside of blood vessels—normally not exposed to the bloodstream.

Coagulation is mainly triggered by FVIIa activating FX after exposure of TF at the broken vessel wall. Approximately one percent of FVII is circulating in its activated enzyme form (FVIIa). FVIIa forms the so-called "extrinsic tenase" complex with TF leading to activation of factor X to FXa, which leads to activation of initial levels of thrombin, and to activation of FIX to FIXa. Thrombin is required to activate FVIII, FV, and platelets. Formation of the "intrinsic tenase" complex consisting of FIXa and FVIIIa leads to activation of FX at a rate which is several orders of magnitude higher than by the FVIIa/TF complex. These amounts of FXa are required to cause the "thrombin burst" leading to formation of enough fibrin to form a stable blood clot. All these processes occur on the membrane surfaces of activated platelets.

Platelets are anucleic cells that circulate in the blood of mammals. In the absence of trauma, the inner surface of blood vessels is lined with a thin layer of endothelial cells that acts to inhibit platelet activation. When blood vessels are damaged, fibrils of collagen in the extracellular matrix (ECM) are exposed. Platelets then begin to adhere to the collagen through the action of specific receptors for collagen present on their plasma membrane. These adhesions activate the platelets in addition to the earlier described mechanisms. Platelets are also activated by thrombin after initiation of coagulation.

Hemophilia refers to a group of bleeding disorders in which it takes a long time for the blood to clot. Hemophilia A is the most common form of the disorder and is caused by a deficiency in Factor VIII. Hemophilia B is less frequent and is caused by a deficiency in Factor IX. Both forms of hemophilia can be effectively treated by administration of either recombinant or plasma derived FVIII or FIX concentrates. Treatment of hemophilia is complicated by the development of inhibitory antibodies to factors VIII or IX. In the case of Factor VIII (FVIII), inhibitors develop in ~30% of the patients. Currently approved therapies in these cases include the infusion of plasma-derived prothrombin complex concentrates, like FEIBA, or recombinant Factor VIIa (rFVIIa), as the therapies for acute bleeds.

BRIEF DESCRIPTION OF THE FIGURES

FIGS. 1A-1B. FACS analyses of non-activated platelets with 100 nM rFVIIa (Novoseven) added for 7 minutes at 37° C. using CD61 PerCP, CD62 PE, and FVII DyLight 488 as markers.

FIGS. 2A-2B. FACS analyses of platelets activated for 7 minutes at 37° C. with thrombin/convulxin and with 100 nM NovoSeven added using CD61 PerCP, CD62 PE, and FVII DyLight 488 as markers.

FIG. 6A. Ratio of binding of rFVIIa to activated vs. non-activated platelets. FIG. 6B. Fluorescence signal to noise ratios of rFVIIa bound to activated or non-activated platelets.

SUMMARY OF THE INVENTION

Figure 1B:
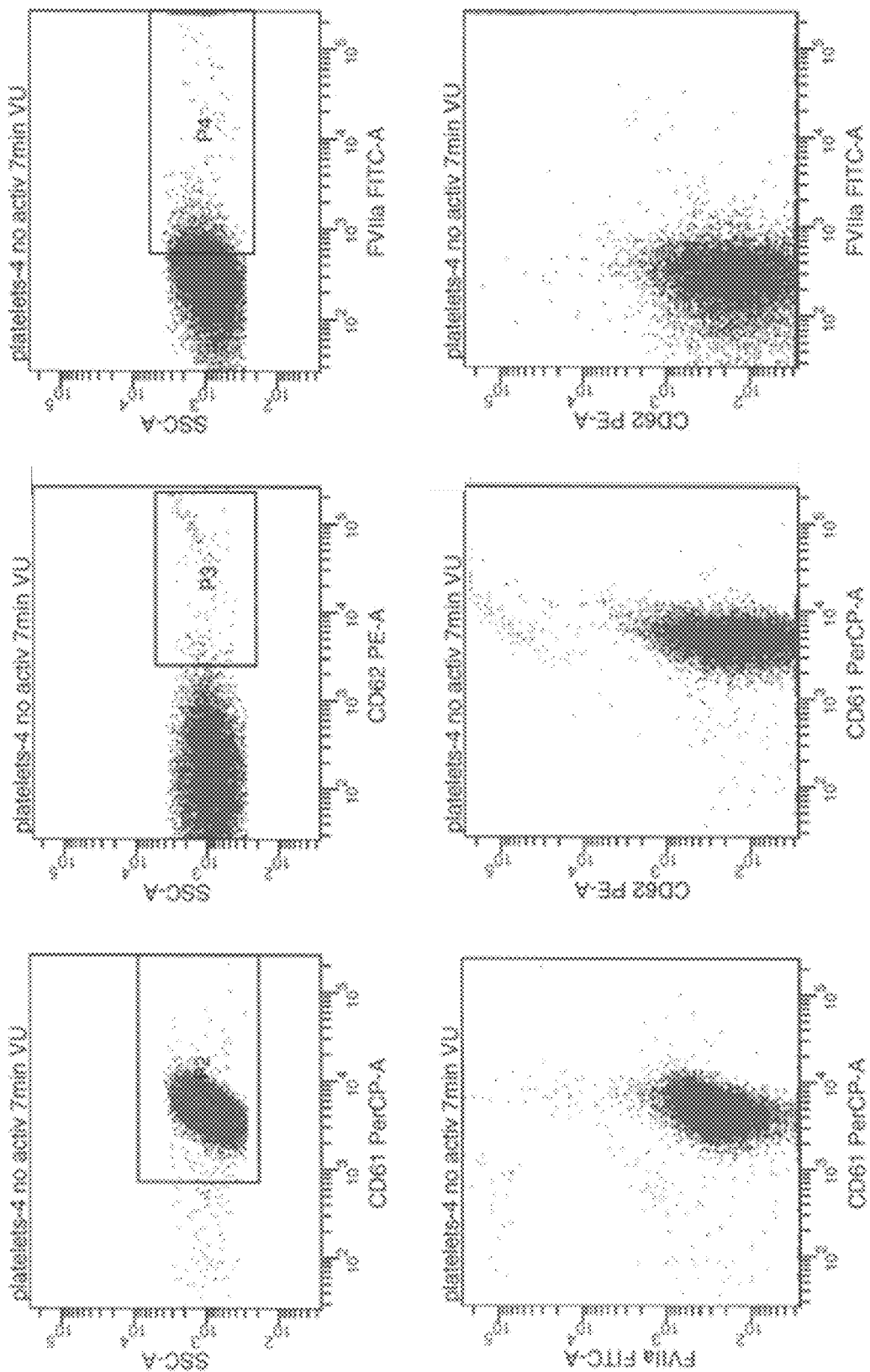

The present invention relates to a platelet subpopulation with high binding capacity to recombinant activated factor VII (rFVIIa), and its use for the treatment of bleeding disorders. The present invention also relates to methods for determining whether a subject is a candidate for treatment with rFVIIa or alternative therapies.

In one aspect, the present invention provides a method of treating hemophilia in a subject in need thereof, the method comprising administering a therapeutically effective amount of rFVIIa to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was detected in the platelet population.

In another aspect, the present invention provides a method of treating hemophilia in a subject in need thereof, the method comprising administering a therapeutically effective amount of an alternative therapy to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was not detected in the platelet population.

In another aspect, the present invention provides a method of treating a non-hemophilia bleeding disorder in a subject in need thereof, the method comprising administering a therapeutically effective amount of rFVIIa to the subject, wherein (a) a sample of platelets derived from the subject was obtained; (b) a platelet population from the sample was incubated with rFVIIa; (c) a subpopulation of platelets having at least a 4-fold higher binding capacity to rFVIIa, as compared to the binding capacity to rFVIIa of the other platelets in the platelet population, was detected in the platelet population; and (d) the subject does not have an unacceptable risk of thrombosis.

In another aspect, the present invention provides a method of treating a non-hemophilia bleeding disorder in a subject in need thereof, the method comprising administering a therapeutically effective amount of an alternative therapy to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was not detected in the platelet population.

In yet another aspect, the invention provides a method of treating a bleeding disorder in a subject in need thereof, the method comprising administering to the subject a therapeutically effective amount of a platelet population enriched with a subpopulation of platelets having at least a 4-fold higher binding capacity to rFVIIa, as compared to the binding capacity to rFVIIa of the other platelets in the platelet population.

In one aspect, the present invention provides a method of treating a bleeding disorder in a subject in need thereof, the method comprising administering a therapeutically effective amount of rFVIIa to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was detected in the platelet population.

In yet another aspect, the present invention provides a method of treating a bleeding disorder in a subject in need thereof, the method comprising administering a therapeutically effective amount of an alternative therapy to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was not detected in the platelet population.

In one embodiment, the detection is by flow cytometry. In one embodiment, the platelets in the subpopulation of platelets are activated. In another embodiment, the platelets in the subpopulation of platelets are non-activated. In one embodiment, the platelets in the subpopulation of platelets are coated.

In one embodiment, the platelet population contains a subpopulation of platelets having about a 6-fold higher binding capacity to rFVIIa, as compared to the binding capacity to rFVIIa of the other platelets in the platelet population. In another embodiment, the platelet population contains a subpopulation of platelets having about a 20-fold higher binding capacity to rFVIIa, as compared to the binding capacity to rFVIIa of the other platelets in the platelet population. In another embodiment, the platelet population contains a subpopulation of platelets having about a 30-fold higher binding capacity to rFVIIa, as compared to the binding capacity to rFVIIa of the other platelets in the platelet population. In one embodiment, the platelet population contains a subpopulation of platelets having about a 40-fold higher binding capacity to rFVIIa, as compared to the binding capacity to rFVIIa of the other platelets in the platelet population.

In one embodiment, the sample of platelets is obtained from a blood sample or a serum sample from the subject. In another embodiment, the sample of platelets is a fresh sample, a concentrate, a preserved sample, a rehydrated lyophilized sample, or a frozen sample.

In one embodiment, the bleeding disorder is hemophilia. In one embodiment, the hemophilia is hemophilia A. In another embodiment, the hemophilia is hemophilia B. In one embodiment, the hemophilia A is congenital hemophilia A with inhibitors or acquired hemophilia A with inhibitory auto antibodies to FVIII, and the hemophilia B is congenital hemophilia B with inhibitors or acquired hemophilia B with inhibitory auto antibodies to FIX.

In one embodiment, the subject does not have an unacceptable risk of thrombosis. In another embodiment, the subject has an unacceptable risk of thrombosis.

In one embodiment, the alternative therapy is Prothrombin Complex Concentrate or activated Prothrombin Complex Concentrate. In one embodiment, the activated Prothrombin Complex Concentrate is FEIBA.

In one embodiment, the alternative therapy is BeneFix®, Kogenate® FS, Recombinate, Advate®, Helixate® FS, Koāte®-DVI, Stimate®, DDAVP®, Bebulin, Hemofil M®, cryoprecipitated antihaemophilic factor (AHF), or fresh frozen plasma (FFP).

In another embodiment, the alternative therapy is recombinant porcine FVIII, recombinant FV variants, recombinant FVIIa variants, recombinant FXa variants, FXIII, prothrombin, fibrinogen, a mix of coagulation factors, antibodies mimicking FVIII, peptides mimicking FVIII, compounds mimicking FVIII, peptide inhibitors of TFPI, antibody inhibitors of TFPI, compounds inhibiting TFPI or compounds inhibiting anti-coagulant proteins.

In one embodiment, the bleeding disorder is a non-hemophilia bleeding disorder. In one embodiment, the non-hemophilia bleeding disorder is blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease or von Willebrand disease with inhibitors to von Willebrand factor.

In one embodiment, the bleeding disorder is hemophilia, blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease or von Willebrand disease with inhibitors to von Willebrand factor.

In another aspect, the present invention provides a subpopulation of platelets isolated from a platelet population, wherein the platelets in the subpopulation of platelets have at least a 4-fold higher binding capacity to rFVIIa as compared to the binding capacity to rFVIIa of the other platelets in the platelet population.

In one embodiment, the higher binding capacity to rFVIIa is determined by flow cytometry. In one embodiment, the platelets in the subpopulation of platelets are activated. In another embodiment, the platelets in the subpopulation of platelets are non-activated. In another embodiment, the platelets in the subpopulation of platelets are coated.

In one embodiment, the platelets in the subpopulation of platelets have about a 6-fold higher binding capacity to rFVIIa, as compared to the binding capacity to rFVIIa of the other platelets in the platelet population. In another embodiment, the platelets in the subpopulation of platelets have about a 20-fold higher binding capacity to rFVIIa, as compared to the binding capacity to rFVIIa of the other platelets in the platelet population. In one embodiment, the platelets in the subpopulation of platelets have about a 30-fold higher binding capacity to rFVIIa, as compared to the binding capacity to rFVIIa of the other platelets in the platelet population. In another embodiment, the platelets in the subpopulation of platelets have about a 40-fold higher binding capacity to rFVIIa, as compared to the binding capacity to rFVIIa of the other platelets in the platelet population.

In one embodiment, the subpopulation of platelets is supplied in the form of a pharmaceutical composition. In one embodiment, the pharmaceutical composition is administered systemically to a subject in need thereof.

In one embodiment, the pharmaceutical composition is used to treat a bleeding disorder. In one embodiment, the bleeding disorder is hemophilia, blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease, or von Willebrand disease with inhibitors to von Willebrand factor.

In another aspect, the present invention provides a method of determining whether a subject is a candidate for treatment with rFVIIa, the method comprising (a) obtaining a sample of platelets derived from the subject; (b) incubating a platelet population from the sample with rFVIIa; (c) detecting whether the platelet population contains a subpopulation of platelets having at least a 4-fold higher binding capacity to rFVIIa, as compared to the binding capacity to rFVIIa of the other platelets in the platelet population, wherein a subject is a candidate for treatment with rFVIIa if the subject does not have an unacceptable risk of thrombosis, and if the platelet population contains a subpopulation of platelets having at least a 4-fold higher binding capacity to rFVIIa, as compared to the binding capacity to rFVIIa of the other platelets in the platelet population.

In one embodiment, the detection is by flow cytometry. In one embodiment, the platelets in the subpopulation of platelets are activated. In another embodiment, the platelets in the subpopulation of platelets are non-activated. In one embodiment, the platelets in the subpopulation of platelets are coated.

In one embodiment, the platelet population contains a subpopulation of platelets having about a 6-fold higher binding capacity to rFVIIa, as compared to the binding capacity to rFVIIa of the other platelets in the platelet population. In another embodiment, the platelet population contains a subpopulation of platelets having about a 20-fold higher binding capacity to rFVIIa, as compared to the binding capacity to rFVIIa of the other platelets in the platelet population. In another embodiment, the platelet population contains a subpopulation of platelets having about a 30-fold higher binding capacity to rFVIIa, as compared to the binding capacity to rFVIIa of the other platelets in the platelet population. In one embodiment, the platelet population contains a subpopulation of platelets having about a 40-fold higher binding capacity to rFVIIa, as compared to the binding capacity to rFVIIa of the other platelets in the platelet population.

In one embodiment, the sample of platelets is obtained from a blood sample or a serum sample from the subject. In another embodiment, the sample of platelets is a fresh sample, a concentrate, a preserved sample, a rehydrated lyophilized sample, or a frozen sample.

In one embodiment, the subject has a bleeding disorder. In one embodiment, the bleeding disorder is hemophilia, blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease or von Willebrand disease with inhibitors to von Willebrand factor. In another embodiment, the bleeding disorder is blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease or von Willebrand disease with inhibitors to von Willebrand factor.

In another aspect, the present invention provides a method of treating a bleeding disorder in a subject in, need thereof, the method comprising administering to the subject a therapeutically effective amount of a platelet population, wherein the platelets in the platelet population have a higher binding capacity to rFVIIa, as compared to the binding capacity to rFVIIa of platelets in a control platelet population.

In one embodiment, the platelets in the subpopulation of platelets are activated. In another embodiment, the platelets in the subpopulation of platelets are non-activated. In one embodiment, the platelets in the subpopulation of platelets are coated.

In one embodiment, the platelets in the platelet population have about a 2-fold higher binding capacity to rFVIIa, as compared to the binding capacity to rFVIIa of platelets in a control platelet population. In one embodiment, the platelets in the platelet population have about a 5-fold higher binding capacity to rFVIIa, as compared to the binding capacity to rFVIIa of platelets in a control platelet population. In one embodiment, the platelets in the platelet population have about a 10-fold higher binding capacity to rFVIIa, as compared to the binding capacity to rFVIIa of platelets in a control platelet population. In another embodiment, the platelets in the platelet population have about a 20-fold higher binding capacity to rFVIIa, as compared to the binding capacity to rFVIIa of platelets in a control platelet population. In one embodiment, the platelets in the platelet population have about a 30-fold higher binding capacity to rFVIIa, as compared to the binding capacity to rFVIIa of platelets in a control platelet population. In another embodiment, the platelets in the platelet population have about a 40-fold higher binding capacity to rFVIIa, as compared to the binding capacity to rFVIIa of platelets in a control platelet population.

In one embodiment, the platelets in the control platelet population are platelets not exposed to rFVIIa. In one embodiment, the platelets in the platelet population have a rFVIIa binding constant of about 50 to 400 nM. In another embodiment, the platelets in the platelet population have a rFVIIa binding constant of about 25 to 1100 nM.

In one embodiment, the bleeding disorder is hemophilia, blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease or von Willebrand disease with inhibitors to von Willebrand factor.

In one embodiment, the subject is a human.

In another aspect, the present invention provides a method of treating a bleeding disorder in a subject in need thereof, the method comprising administering a therapeutically effective amount of rFVIIa to the subject, wherein (a) a sample of platelets derived from the subject was obtained; (b) a platelet population from the sample was incubated with rFVIIa; and (c) platelets having a high binding capacity to rFVIIa, as compared to the binding capacity to rFVIIa of a control platelet population, were detected in the platelet population.

In another aspect, the present invention provides a method of treating a bleeding disorder in a subject in need thereof, the method comprising administering a therapeutically effective amount of an alternative therapy to the subject, wherein (a) a sample of platelets derived from the subject was obtained; (b) a platelet population from the sample was incubated with rFVIIa; and (c) platelets having a high binding capacity to rFVIIa, as compared to the binding capacity to rFVIIa of a control platelet population, were detected in the platelet population.

In another aspect, the present invention provides a method of treating a bleeding disorder in a subject m need thereof, the method comprising administering a therapeutically effective amount of an alternative therapy to the subject, wherein (a) a sample of platelets derived from the subject was obtained; (b) a platelet population from the sample was incubated with rFVIIa; and (c) platelets having a low binding capacity to rFVIIa, as compared to the binding capacity to rFVIIa of a control platelet population, were detected in the platelet population.

In one embodiment, the detection is by flow cytometry. In one embodiment, the platelets are activated. In another embodiment; the platelets are non-activated. In one embodiment, the platelets are coated.

In one embodiment, the control platelet population is a platelet population not exposed to rFVIIa.

In one embodiment the control platelet population has a rFVIIa binding constant of about 200 nM.

In one embodiment, the platelets having a high binding capacity to rFVIIa have about a 25-fold higher binding capacity to rFVIIa, as compared to the binding capacity to rFVIIa of a control platelet population. In another embodiment, the platelets having a high binding capacity to rFVIIa have about a 35-fold higher binding capacity to rFVIIa, as compared to the binding capacity to rFVIIa of a control platelet population.

In one embodiment, the platelets having a low binding capacity to rFVIIa have about a 5-fold higher binding capacity to rFVIIa, as compared to the binding capacity to rFVIIa of a control platelet population. In another embodiment, the platelets having a low binding capacity to rFVIIa have about a 10-fold higher binding capacity to rFVIIa, as compared to the binding capacity to rFVIIa of a control platelet population.

In one embodiment, the sample of platelets is obtained from a blood sample or a serum sample from the subject. In another embodiment, the sample of platelets is a fresh sample, a concentrate; a preserved sample, a rehydrated lyophilized sample, or a frozen sample.

In one embodiment, the bleeding disorder is hemophilia. In one embodiment, the hemophilia is hemophilia A or hemophilia B. In another embodiment, the hemophilia A is congenital hemophilia A with inhibitors or acquired hemophilia A with inhibitory auto antibodies to FVIII, and the hemophilia B is congenital hemophilia B with inhibitors or acquired hemophilia B with inhibitory auto antibodies to FIX.

In one embodiment, the subject does not have an unacceptable risk of thrombosis. In another embodiment, the subject has an unacceptable risk of thrombosis.

In one embodiment, the bleeding disorder is a non-hemophilia bleeding disorder. In one embodiment, the non-hemophilia bleeding disorder is blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease or von Willebrand disease with inhibitors to von Willebrand factor.

In one embodiment, the alternative therapy is Prothrombin Complex Concentrate or activated Prothrombin Complex Concentrate. In one embodiment, the activated Prothrombin Complex Concentrate is FEIBA.

In one embodiment, the alternative therapy is BeneFix®, Kogenate® FS, Recombinate, Advate®, Helixate® FS, Koāe®-DVI, Stimate®, DDAVP®, Bebulin, Hemofil M®, cryoprecipitated antihaemophilic factor (AHF), or fresh frozen plasma (FFP).

In another embodiment, the alternative therapy is recombinant porcine FVIII, recombinant FV variants, recombinant FVIIa variants, recombinant FXa variants, FXIII, prothrombin, fibrinogen, a mix of coagulation factors, antibodies mimicking FVIII, peptides mimicking FVIII, compounds mimicking FVIII, peptide inhibitors of TFPI, antibody inhibitors of TFPI, compounds inhibiting TFPI or compounds inhibiting anti-coagulant proteins.

In one embodiment, the subject is a human.

DETAILED DESCRIPTION

Definitions and Abbreviations

The term "N7" designates the drugs Novoseven® and Novoseven® RT. Novoseven® and Novoseven® RT are recombinant human Factor VIIa (rFVIIa), intended for promoting hemostasis by activating the extrinsic pathway of the coagulation cascade. Dosage and methods of administration of Novoseven® and Novoseven® RT are known to one of skill in the art. For more information, see e.g., www.novosevenrt.com/.

The term "BAX817" designates the drug BAX 817. BAX817 is recombinant Factor VIIa therapy, intended for treating acute bleedings in subjects with hemophilia A or B with Factor VIII or Factor IX inhibitors.

The term "rFVIIa" designates Recombinant Factor VIIa. Indications, dosage and methods of administration of rFVIIa are known to one of skill in the art (see e.g., Ng and Lee, 2006, *Vasc Health Risk Alanag.*, 2(4): 433-440; see also Abshire and Kenet, 2004, *J Thromb Haemost.*, 2(6):899-909.)

The term "non-hemophilia bleeding disorder" designates a bleeding disorder that is not hemophilia, including, but not limited to, hemophilia A, hemophilia B, hemophilia A with inhibitors, hemophilia B with inhibitors.

An "unacceptable risk of thrombosis" is a risk that is not medically appropriate in view of the potential benefit to the patient.

The term "coated", as applied to coated platelets, represents a subpopulation of cells observed after dual agonist stimulation of platelets with collagen and thrombin. These platelets retain on their surface high levels of several procoagulant proteins, including fibrinogen, von Willebrand factor, fibronectin, factor V and thrombospondin. For additional information, see e.g., Dale G L., 2005, *J Thromb Haemost.* (10):2185-92. rFVIIa has been shown to preferentially bind to the "coated" platelet population emerging after activation with thrombin and convulxin, a GPVI agonist (Kjalke M., 2007, *J Thromb Haemost.* (5):774-80.). It has also been shown that a "coated" platelet sub-population exposes high levels of Factor V, fibrinogen/fibrin, vWF (von Willebrand Factor), fibronectin, negatively charged phospholipids (see Kjalke et al., JTH 2007; 5: 774-80).

The singular forms "a," "an," and "the" include plural reference unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

DETAILED DESCRIPTION

The present invention relates to a platelet subpopulation with high binding capacity to recombinant activated factor VII (rFVIIa), and its use for the treatment of blood disorders. The present invention also relates to a method for determining whether a subject is a candidate for treatment with rFVIIa or alternative therapies.

1. Methods of Treatment

In one aspect, the present invention provides a method of treating hemophilia in a subject in need thereof, the method comprising administering a therapeutically effective amount of rFVIIa to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was detected in the platelet population.

In another aspect, the present invention provides a method of treating hemophilia in a subject in need thereof, the method comprising administering a therapeutically effective amount of an alternative therapy to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was not detected in the platelet population.

In another aspect, the present invention provides a method of treating a non-hemophilia bleeding disorder in a subject in need thereof, the method comprising administering a therapeutically effective amount of rFVIIa to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was detected in the platelet population. In addition, the rFVIIa might be administered if the subject does not have an unacceptable risk of thrombosis.

In another aspect, the present invention provides a method of treating a non-hemophilia bleeding disorder in a subject in need thereof, the method comprising administering a therapeutically effective amount of an alternative therapy to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was not detected in the platelet population.

In yet another aspect, the invention provides a method of treating a bleeding disorder in a subject in need thereof, the method comprising administering to the subject a therapeutically effective amount of a platelet population enriched with a subpopulation of platelets having at least a 4-fold higher binding capacity to rFVIIa, as compared to the binding capacity to rFVIIa of the other platelets in the platelet population.

In one aspect, the present invention provides a method of treating a bleeding disorder in a subject in need thereof, the method comprising administering a therapeutically effective amount of rFVIIa to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was detected in the platelet population.

In yet another aspect, the present invention provides a method of treating a bleeding disorder in a subject in need thereof, the method comprising administering a therapeutically effective amount of an alternative therapy to the subject, wherein (a) a sample of platelets derived from the subject was obtained; (b) a platelet population from the sample was incubated with rFVIIa; and (c) a subpopulation of platelets having at least a 4-fold higher binding capacity to rFVIIa, as compared to the binding capacity to rFVIIa of the other platelets in the platelet population, was not detected in the platelet population.

In another aspect, the invention provides a method of treating a bleeding disorder in a subject in need thereof, the method comprising administering to the subject a therapeutically effective amount of a platelet population, wherein the platelets in the platelet population have a higher binding capacity to rFVIIa, as compared to the binding capacity to rFVIIa of platelets in a control platelet population.

In another aspect, the invention provides a method of treating a bleeding disorder in a subject in need thereof, the method comprising administering to the subject a therapeutically effective amount of a platelet population, wherein the platelets in the platelet population have at least a 0.25 fold, 0.5-fold, 1-fold, 1.5-fold, 2-fold, 2.5 fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, or higher binding capacity to rFVIIa, as compared to the binding capacity to rFVIIa of platelets in a control platelet population.

In one embodiment, the platelets in the control platelet population are platelets not exposed to rFVIIa.

In one embodiment, the detection is by flow cytometry. In another embodiment, the detection is by immunofluorescence. In yet another embodiment, the detection is by microscopy, such as, but not limited to, electron microscopy or confocal laser scanning microscopy (CLSM or LSCM). In a further embodiment, the detection is by an immunoassay, such as, but not limited to, cell-based enzyme-linked immunosorbent assay. In another embodiment, the detection is by any method known to one skill in the art that would detect rFVIIa bound platelets.

In one embodiment, the binding capacity to rFVIIa of platelets in a platelet population or in a subpopulation of platelets is measured through detection of fluorescence intensity. In one embodiment, the fluorescence intensity is proportional to the amount of rFVIIa bound to the platelets.

In one embodiment, the platelets in the platelet population are activated. In another embodiment, the platelets in the platelet population are non-activated. In one embodiment, the platelets in the platelet population are coated. In another embodiment, the platelets in the platelet population are not coated.

In one embodiment, the platelets in the subpopulation of platelets are activated. In another embodiment, the platelets in the subpopulation of platelets are non-activated. In one embodiment, the platelets in the subpopulation of platelets are coated. In another embodiment, the platelets in the subpopulation of platelets are not coated.

In one embodiment, the platelets in the control platelet population are activated. In another embodiment, the platelets in the control platelet population are non-activated. In one embodiment, the platelets in the control platelet population are coated. In another embodiment, the platelets in the control platelet population are not coated.

In one embodiment, the platelets in the platelet population have a rFVIIa binding constant of about 25 to 1100 nM. In another embodiment, the platelets in the platelet population have a rFVIIa binding constant of about 50 to 400 nM. In further embodiments, the platelets in the platelet population have a rFVIIa binding constant of about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 1100 nM, about 1200 nM, about 1300 nM, about 1400 nM, about 1500 nM, about 1600 nM, about 1700 nM, about 1800 nM, about 1900 nM, about 2000 nM, about 3000 nM, about 4000 nM, or about 5000 nM, about 6000 nM, about 7000 nM, about 8000 nM, about 9000 nM, about 10,000 nM, or more.

In other embodiments, the platelets in the platelet population have a rFVIIa binding constant of about 10 nM to 30 nM, about 20 nM to 40 nM, about 30 nM to 50 nM, about 40 nM to 60 nM, about 50 nM to 70 nM, about 60 nM to 80 nM, about 70 nM to 90 nM, about 80 nM to 100 nM, 90 nM to 110 nM, about 100 nM to 120 nM, about 110 nM to 130 nM, about 120 nM to 140 nM, about 130 nM to 150 nM, about 140 nM to 160 nM, about 150 nM to 170 nM, about 160 nM to 180 nM, about 170 nM to 190 nM, about 180 nM to 200 nM, about 190 nM to 210 nM, about 200 nM to 220 nM, about 210 nM to 230 nM, about 220 nM to 240 nM, about 230 nM to 250 nM, about 240 nM to 260 nM, about 250 nM to 270 nM, about 260 nM to 280 nM, about 270 nM to 290 nM, about 280 nM to 300 nM, about 290 nM to 310 nM, about 300 nM to 320 nM, about 310 nM to 330 nM, about 320 nM to 340 nM, about 330 nM to 350 nM, about 340 nM to 360 nM, about 350 nM to 370 nM, about 360 nM to 380 nM, about 370 nM to 390 nM, about 380 nM to 400 nM, about 390 nM to 410 nM, about 400 nM to 450 nM, about 450 nM to 500 nM, about 500 nM to 550 nM, about 550 nM to 600 nM, about 600 nM to 650 nM, about 650 nM to 700 nM, about 700 nM to 750 nM, about 750 nM to 800 nM, about 800 nM to 850 nM, about 850 nM to 900 nM, about 900 nM to 950 nM, about 950 nM to 1000 nM, about 1000 nM to 1050 nM, about 1050 nM to 1100 nM, about 1100 nM to 1150 nM, about 1150 nM to 1200 nM, about 1200 nM to 1250 nM, about 1250 nM to 1300 nM, about 1300 nM to 1350 nM, about 1350 nM to 1400 nM, about 1400 nM to 1450 nM, or about 1450 nM to 1500 nM, or any range in between.

In other embodiments, the platelets in the subpopulation of platelets have a rFVIIa binding constant of about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 1100 nM, about 1200 nM, about 1300 nM, about 1400 nM, about 1500 nM, about 1600 nM, about 1700 nM, about 1800 nM, about 1900 nM, about 2000 nM, about 3000 nM, about 4000 nM, about 5000 nM, about 6000 nM, about 7000 nM, about 8000 nM, about 9000 nM, about 10,000 nM, or more.

In other embodiments, the platelets in the subpopulation of platelets have a rFVIIa binding constant of about 10 nM to 30 nM, about 20 nM to 40 nM, about 30 nM to 50 nM, about 40 nM to 60 nM, about 50 nM to 70 nM, about 60 nM to 80 nM, about 70 nM to 90 nM, about 80 nM to 100 nM, 90 nM to 110 nM, about 100 nM to 120 nM, about 110 nM to 130 nM, about 120 nM to 140 nM, about 130 nM to 150 nM, about 140 nM to 160 nM, about 150 nM to 170 nM, about 160 nM to 180 nM, about 170 nM to 190 nM, about 180 nM to 200 nM, about 190 nM to 210 nM, about 200 nM to 220 nM, about 210 nM to 230 nM, about 220 nM to 240 nM, about 230 nM to 250 nM, about 240 nM to 260 nM, about 250 nM to 270 nM, about 260 nM to 280 nM, about 270 nM to 290 nM, about 280 nM to 300 nM, about 290 nM to 310 nM, about 300 nM to 320 nM, about 310 nM to 330 nM, about 320 nM to 340 nM, about 330 nM to 350 nM, about 340 nM to 360 nM, about 350 nM to 370 nM, about 360 nM to 380 nM, about 370 nM to 390 nM, about 380 nM to 400 nM, about 390 nM to 410 nM, about 400 nM to 450 nM, about 450 nM to 500 nM, about 500 nM to 550 nM, about 550 nM to 600 nM, about 600 nM to 650 nM, about 650 nM to 700 nM, about 700 nM to 750 nM, about 750 nM to 800 nM, about 800 nM to 850 nM, about 850 nM to 900 nM, about 900 nM to 950 nM, about 950 nM to 1000 nM, about 1000 nM to 1050 nM, about 1050 nM to 1100 nM, about 1100 nM to 1150 nM, about 1150 nM to 1200 nM, about 1200 nM to 1250 nM, about 1250 nM to 1300 nM, about 1300 nM to 1350 nM, about 1350 nM to 1400 nM, about 1400 nM to 1450 nM, or about 1450 nM to 1500 nM, or any range in between.

In one embodiment, the platelets in the control platelet population have a rFVIIa binding constant of about 25 to 1100 nM. In another embodiment, the platelets in the control platelet population have a rFVIIa binding constant of about 50 to 400 nM. In further embodiments, the platelets in the control platelet population have a rFVIIa binding constant of about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 1100 nM, about 1200 nM, about 1300 nM, about 1400 nM, about 1500 nM, about 1600 nM, about 1700 nM, about 1800 nM, about 1900 nM, about 2000 nM, about 3000 nM, about 4000 nM, or about 5000 nM, about 6000 nM, about 7000 nM, about 8000 nM, about 9000 nM, about 10,000 nM, or more.

In other embodiments, the platelets in the control platelet population have a rFVIIa binding constant of about 10 nM to 30 nM, about 20 nM to 40 nM, about 30 nM to 50 nM, about 40 nM to 60 nM about 50 nM to 70 nM, about 60 nM to 80 nM, about 70 nM to 90 nM, about 80 nM to 100 nM, 90 nM to 110 nM, about 100 nM to 120 nM, about 110 nM to 130 nM, about 120 nM to 140 nM, about 130 nM to 150 nM, about 140 nM to 160 nM, about 150 nM to 170 nM, about 160 nM to 180 nM, about 170 nM to 190 nM, about 180 nM to 200 nM, about 190 nM to 210 nM, about 200 nM to 220 nM, about 210 nM to 230 nM, about 220 nM to 240 nM, about 230 nM to 250 nM, about 240 nM to 260 nM, about 250 nM to 270 nM, about 260 nM to 280 nM, about 270 nM to 290 nM, about 280 nM to 300 nM, about 290 nM to 310 nM, about 300 nM to 320 nM, about 310 nM to 330 nM, about 320 nM to 340 nM, about 330 nM to 350 nM, about 340 nM to 360 nM, about 350 nM to 370 nM, about 360 nM to 380 nM, about 370 nM to 390 nM, about 380 nM to 400 nM, about 390 nM to 410 nM, about 400 nM to 450 nM, about 450 nM to 500 nM, about 500 nM to 550 nM, about 550 nM to 600 nM, about 600 nM to 650 nM, about 650 nM to 700 nM, about 700 nM to 750 nM, about 750 nM to 800 nM, about 800 nM to 850 nM, about 850 nM to 900 nM, about 900 nM to 950 nM, about 950 nM to 1000 nM, about 1000 nM to 1050 nM, about 1050 nM to 1100 nM, about 1100 nM to 1150 nM, about 1150 nM to 1200 nM, about 1200 nM to 1250 nM, about 1250 nM to 1300 nM, about 1300 nM to 1350 nM, about 1350 nM to 1400 nM, about 1400 nM to 1450 nM, or about 1450 nM to 1500 nM, or any range in between.

In one embodiment, the platelet population contains a subpopulation of platelets having about a 0.1-fold, 0.15-fold, 0.2-fold, 0.25-fold, 0.3-fold, 0.4-fold, 0.5 fold, 0.6-fold, 0.7-fold, 0.8-fold, 0.9-fold, 1-fold, 1.5-fold, 2 fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, or about a 9-fold higher binding capacity to rFVIIa, as compared to the binding capacity to rFVIIa of the other platelets in the platelet population.

In another embodiment, the platelet population contains a subpopulation of platelets having about a 10-fold, 11-fold, 12 fold, 13-fold, 14-fold, 15-fold, 16-fold, 17-fold, 18-fold, or a 19-fold higher binding capacity to rFVIIa, as compared to the binding capacity to rFVIIa of the other platelets in the platelet population.

In one embodiment, the platelet population contains a subpopulation of platelets having about a 20-fold, 21-fold, 22-fold, 23-fold, 24-fold, 25-fold, 26-fold, 27-fold, 28-fold, or a 29-fold higher binding capacity to rFVIIa, as compared to the binding capacity to rFVIIa of the other platelets in the platelet population.

In another embodiment, the platelet population contains a subpopulation of platelets having about a 30-fold, 31-fold, 32-fold, 33-fold, 34-fold, 35-fold, 36-fold, 37-fold, 38-fold, or a 39-fold higher binding capacity to rFVIIa, as compared to the binding capacity to rFVIIa of the other platelets in the platelet population.

In one embodiment, the platelet population contains a subpopulation of platelets having about a 40-fold, 41-fold, 42-fold, 43-fold, 44-fold, 45-fold, 46-fold, 47-fold, 48-fold, or a 49-fold higher binding capacity to rFVIIa, as compared to the binding capacity to rFVIIa of the other platelets in the platelet population.

In another embodiment, the platelet population contains a subpopulation of platelets having about a 50-fold, 51-fold, 52-fold, 53-fold, 54-fold, 55-fold, 56-fold, 57-fold, 58-fold, 59-fold, 60-fold, 70-fold, 80-fold, 90-fold, 100-fold, 150-fold, 200-fold, 250-fold, 300-fold, 350-fold, 400-fold, 450-fold, or about a 500-fold higher binding capacity to rFVIIa, as compared to the binding capacity to rFVIIa of the other platelets in the platelet population.

In another embodiment, the platelet population contains a subpopulation of platelets having about a 0.1-fold to 0.3- fold, 0.2-fold to 0.4-fold, 0.3-fold to 0.5-fold, 0.4-fold to 0.6-fold, 0.5-fold to 0.7-fold, 0.6-fold to 0.8-fold, 0.7-fold to 0.9-fold, 0.8-fold to 1.0-fold, 0.9-fold to 1.1-fold, 1-fold to 1.5-fold, 1.25-fold to 1.75-fold, 1.5-fold to 2-fold, 1.75-fold to 2.25-fold, 2-fold to 2.5-fold, 2.25-fold to 2.75-fold, 2.5-fold to 3-fold, 2.75-fold to 3.25-fold, 3-fold to 4-fold, 3.5-fold to 4.5-fold, 4-fold to 5-fold, 4.5-fold to 5.5-fold, 5-fold to 6-fold, 6-fold to 8-fold, 8-fold to 10-fold, 10-fold to 12-fold, 12-fold to 14-fold, 14-fold to 16-fold, 16-fold to 18-fold, 18-fold to 20-fold, 20-fold to 25-fold, 25-fold to 3-fold, 30-fold to 40-fold, 40-fold to 50-fold, 50-fold to 70-fold, 70-fold to 90-fold, 90-fold to 100-fold, 100-fold to 120-fold, 120-fold to 140-fold, 140-fold to 160-fold, 1-fold to 20-fold, 10-fold to 30-fold, 20-fold to 40-fold, 30-fold to 50-fold, 40-fold to 60-fold, 50-fold to 80-fold, 60-fold to 80-fold, 70-fold to 90-fold, 80-fold to 100-fold, 100-fold to 150-fold, 130-fold to 180-fold, or any range in between, higher binding capacity to rFVIIa, as compared to the binding capacity to rFVIIa of the other platelets in the platelet population.

In one embodiment, the platelets in the platelet population have about a 0.1-fold, 0.15-fold, 0.2-fold, 0.25-fold, 0.3-fold, 0.4-fold, 0.5-fold, 0.6-fold, 0.7-fold, 0.8-fold, 0.9-fold, 1-fold, 1.5-fold, 2 fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, or about a 9-fold higher binding capacity to rFVIIa, as compared to the binding capacity to rFVIIa of platelets in a control platelet population.

In another embodiment, the platelets in the platelet population have about a 10-fold, 11-fold, 12 fold, 13-fold, 14-fold, 15-fold, 16-fold, 17-fold, 18-fold, or a 19-fold higher binding capacity to rFVIIa, as compared to the binding capacity to rFVIIa of platelets in a control platelet population.

In one embodiment, the platelets in the platelet population have about a 20-fold, 21-fold, 22-fold, 23-fold, 24-fold, 25-fold, 26-fold, 27-fold, 28-fold, or a 29-fold higher binding capacity to rFVIIa, as compared to the binding capacity to rFVIIa of platelets in a control platelet population.

In another embodiment; the platelets in the platelet population have about a 30-fold, 31-fold, 32-fold, 33-fold, 34-fold, 35-fold, 36-fold, 37-fold, 38-fold, or a 39-fold higher binding capacity to rFVIIa, as compared to the binding capacity to rFVIIa of platelets in a control platelet population.

In another embodiment, the platelets in the platelet population have about a 40-fold, 41-fold, 42-fold, 43-fold, 44-fold, 45-fold, 46-fold, 47-fold, 48-fold, or a 49-fold higher binding capacity to rFVIIa, as compared to the binding capacity to rFVIIa of platelets in a control platelet population.

In another embodiment; the platelets in the platelet population have about a 50-fold, 51-fold, 52-fold, 53-fold, 54-fold, 55-fold, 56-fold, 57-fold, 58-fold, 59-fold, 60-fold, 70-fold, 80-fold, 90-fold, 100-fold, 150-fold, 200-fold, 250-fold, 300-fold, 350-fold, 400-fold, 450-fold, or about a 500-fold higher binding capacity to rFVIIa, as compared to the binding capacity to rFVIIa of platelets in a control platelet population.

In another embodiment, the platelets in the platelet population have about a 4-fold to 33-fold higher binding capacity, as compared to the binding capacity to rFVIIa of platelets in a control platelet population. In another embodiment, the platelets in the platelet population have about a 5-fold to 37-fold higher binding capacity, as compared to the binding capacity to rFVIIa of platelets in a control platelet population.

In another embodiment, the platelets in the platelet population have about a 0.3-fold to 2.4-fold higher binding capacity, as compared to the binding capacity to rFVIIa of platelets in a control platelet population. In another embodiment, the platelets in the platelet population have about a 0.3-fold to 2.5-fold higher binding capacity, as compared to the binding capacity to rFVIIa of platelets in a control platelet population.

In, another embodiment; the platelets in the platelet population have about a 0.1-fold to 0.3-fold, 0.2-fold to 0.4-fold, 0.3-fold to 0.5-fold, 0.4-fold to 0.6-fold, 0.5-fold to 0.7-fold, 0.6-fold to 0.8-fold, 0.7-fold to 0.9-fold, 0.8-fold to 1.0-fold, 0.9-fold to 1.1-fold, 1-fold to 1.5-fold, 1.25-fold to 1.75-fold, 1.5-fold to 2-fold, 1.75-fold to 2.25-fold, 2-fold to 2.5-fold, 2.25-fold to 2.75-fold, 2.5-fold to 3-fold, 2.75-fold to 3.25-fold, 3-fold to 4-fold, 3.5-fold to 4.5-fold, 4-fold to 5-fold, 4.5-fold to 5.5-fold, 5-fold to 6-fold, 6-fold to 8-fold, 8-fold to 10-fold, 10-fold to 12-fold, 12-fold to 14-fold, 14-fold to 16-fold, 16-fold to 18-fold, 18-fold to 20-fold, 20-fold to 25-fold, 25-fold to 3-fold, 30-fold to 40-fold, 40-fold to 50-fold, 50-fold to 70-fold, 70-fold to 90-fold, 90-fold to 100-fold, 100-fold to 120-fold, 120-fold to 140-fold, 140-fold to 160-fold, 1-fold to 20-fold, 10-fold to 30-fold, 20-fold to 40-fold, 30-fold to 50-fold, 40-fold to 60-fold, 50-fold to 80-fold, 60-fold to 80-fold, 70-fold to 90-fold, 80-fold to 100-fold, 100-fold to 150-fold, 130-fold to 180-fold, or any range in between higher binding capacity to rFVIIa, as compared to the binding capacity to rFVIIa of platelets in a control platelet population.

In another embodiment, the platelet population contains a subpopulation of platelets having about a 50%, 75%, 100%, 125%, 150%, 175%, 200%, 300%, 400%, or a 500% higher binding capacity to rFVIIa, as compared to the binding capacity to rFVIIa of the other platelets in the platelet population.

In one embodiment, the platelet subpopulation with a higher binding capacity to rFVIIa, as compared to the binding capacity to rFVIIa of the other platelets in the platelet population, consists of at least 2% of the platelet population. In another embodiment, the platelet subpopulation consists of at least 0.5%, 1%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 40%, 50%, or higher, of the platelet population.

In one embodiment, rFVIIa is incubated with a platelet population or a platelet subpopulation. In one embodiment, the platelet population or the platelet subpopulation is from a sample of platelets derived from a subject.

In one embodiment, the concentration of rFVIIa is about 5 nM, 10 nM, 20 nM, 30 nM, 40 nM, 50 nM, 100 nM, 200 nM, 300 nM, 400 nM, 500 nM, 600 nM, 700 nM, 800 nM, 900 nM, 1000 nM, 1100 nM, 1200 nM, 1300 nM, 1400 nM, 1500 nM, 1600 nM, 1700 nM, 1800 nM, 1900 nM, 2000 nM, 3000 nM, 4000 nM, 5000 nM, 6000 nM, or more.

In one embodiment, the platelets in the control platelet population are platelets not exposed to rFVIIa. In one embodiment, the platelets in the platelet population have a rFVIIa binding constant of about 50 to 400 nM. In another embodiment, the platelets in the platelet population have a rFVIIa binding constant of about 25 to 1100 nM.

In one embodiment, the sample of platelets is obtained from a blood sample from the subject. In another embodiment, the sample of platelets is obtained from a serum sample from the subject. In one embodiment, the sample of platelets is a fresh sample. In another embodiment, the sample of platelets is a concentrate. In one embodiment, the sample of platelets is a preserved sample. In another embodiment, the sample of platelets is a rehydrated lyophilized sample. In one embodiment, the sample of platelets is a frozen sample.

In one embodiment, the bleeding disorder is hemophilia. In one embodiment, the hemophilia is hemophilia with inhibitors. In another embodiment, the hemophilia is hemophilia without inhibitors. In a further embodiment, the hemophilia is hemophilia A. In yet another embodiment the hemophilia is hemophilia B. In one embodiment, the hemophilia is hemophilia A with inhibitors. In another embodiment, the hemophilia is hemophilia B with inhibitors. In one embodiment, the inhibitors are to Factor VIII. In another embodiment the inhibitors are to Factor IX. In another embodiment, the hemophilia is acquired hemophilia. In one embodiment, the hemophilia is, congenital hemophilia A with inhibitors. In another embodiment, the hemophilia is acquired hemophilia A with inhibitory auto antibodies to FVIII. In one embodiment, the hemophilia is congenital hemophilia B with inhibitors. In another embodiment, the hemophilia is acquired hemophilia B with inhibitory auto antibodies to FIX.

In one embodiment, the bleeding disorder is a non-hemophilia bleeding disorder. In one embodiment, the bleeding disorder is blood loss from trauma. In another embodiment, the bleeding disorder is FVII deficiency. In one embodiment, the bleeding disorder is FV deficiency. In another embodiment, the bleeding disorder is FX deficiency. In one embodiment, the bleeding disorder is FXI deficiency. In one embodiment, the bleeding disorder is FXIII deficiency. In one embodiment, the bleeding disorder is fibrinogen deficiency. In one embodiment, the bleeding disorder is prothrombin deficiency. In another embodiment, the bleeding disorder is dilutional coagulopathy. In a further embodiment, the bleeding disorder is thrombocytopenia. In yet another embodiment, the bleeding disorder is blood loss from high-risk surgeries. In another embodiment, the bleeding disorder is intracerebral hemorrhage. In one embodiment, the bleeding disorder is von Willebrand disease. In a further embodiment, the bleeding disorder is von Willebrand disease with inhibitors to von Willebrand factor.

In one embodiment, the bleeding disorder is a congenital platelet function defect, including, but not limited to, platelet storage pool disorder, Glanzmann's thrombasthenia, or Bernard-Soulier syndrome. In one embodiment, the bleeding disorder is an acquired platelet function defect. In one embodiment, the bleeding disorder is a congenital deficiency of Factor II, Factor V, Factor VII, Factor X, or Factor XI. In one embodiment, the bleeding disorder is neonatal and pediatric coagulopathies. In one embodiment, the bleeding disorder is a platelet function disorder. In another embodiment, the bleeding disorder is heparin-induced thrombocytopenia. In one embodiment, the bleeding disorder is disseminated intravascular coagulation. In other embodiments, the bleeding disorder is any disorder known to one of skill in the art (for additional information, see e.g., The Absite Review, by Steven M. Fiser, Lippincott Williams and Wilkins 2004).

In one embodiment, the non-hemophilia bleeding disorder is blood loss from trauma. In another embodiment, the non-hemophilia bleeding disorder is FVII deficiency. In one embodiment, the non-hemophilia bleeding disorder is FV deficiency. In another embodiment, the non-hemophilia bleeding disorder is FX deficiency. In one embodiment, the non-hemophilia bleeding disorder is FXI deficiency. In one embodiment, the non-hemophilia bleeding disorder is FXIII deficiency. In one embodiment, the non-hemophilia bleeding disorder is fibrinogen deficiency. In one embodiment, the non-hemophilia bleeding disorder is prothrombin deficiency. In another embodiment, the non-hemophilia bleeding disorder is dilutional coagulopathy. In a further embodiment, the non-hemophilia bleeding disorder is thrombocytopenia. In yet another embodiment, the non-hemophilia bleeding disorder is blood loss from high-risk surgeries. In another embodiment, the non-hemophilia bleeding disorder is intracerebral hemorrhage. In one embodiment, the non-hemophilia bleeding disorder is von Willebrand disease. In a further embodiment, the non-hemophilia bleeding disorder is von Willebrand disease with inhibitors to von Willebrand factor.

In one embodiment, the non-hemophilia bleeding disorder is a congenital platelet function defect, including, but not limited to, platelet storage pool disorder, Glanzmann's thrombasthenia, or Bernard-Soulier syndrome. In one embodiment, the non-hemophilia bleeding disorder is an acquired platelet function defect. In one embodiment, the non-hemophilia bleeding disorder is a congenital deficiency of Factor II, Factor V, Factor VII, Factor X, or Factor XI. In one embodiment, the non-hemophilia bleeding disorder is neonatal and pediatric coagulopathies. In one embodiment, the non-hemophilia bleeding disorder is a platelet function disorder. In another embodiment, the non-hemophilia bleeding disorder is heparin-induced thrombocytopenia. In one embodiment, the non-hemophilia bleeding disorder is disseminated intravascular coagulation. In other embodiments, the non-hemophilia bleeding disorder is any disorder known to one of skill in the art. For additional information on bleeding disorders, see e.g., The Absite Review, by Steven M. Fiser, Lippincott Williams and Wilkins 2004).

In one embodiment, the alternative therapy is Prothrombin Complex Concentrate or activated Prothrombin Complex Concentrate. In one embodiment, the activated Prothrombin Complex Concentrate is FEIBA.

In one embodiment; the alternative therapy is FEIBA. In one embodiment, the alternative therapy is BeneFix® (recombinant Factor IX). In another embodiment, the alternative therapy is Kogenate® FS (recombinant Factor VIII). In one embodiment, the alternative therapy is Recombinate (recombinant Factor VIII). In one embodiment, the alternative therapy is Advate® (recombinant Factor VIII). In one embodiment, the alternative therapy is Helixate® FS (recombinant Factor VIII). In one embodiment, the alternative therapy is Koāte®-DVI (recombinant Factor VIII). In one embodiment, the alternative therapy is Stimate® (desmopressin acetate). In another embodiment, the alternative therapy is DDAVP® (desmopressin acetate). In another embodiment, the alternative therapy is Bebulin (Factor IX Complex). In a further embodiment, the alternative therapy is cryoprecipitated antihaemophilic factor (AHF). In another embodiment, the alternative therapy is Hemofil M® (human factor VIII). In yet another embodiment, the alternative therapy is fresh frozen plasma (FFP). For additional information on therapies to treat bleeding disorders, including dosage and administration, see e.g., The Absite Review, by Steven M. Fiser, Lippincott Williams and Wilkins 2004.

The term "FEIBA" designates the drug Factor VIII Inhibitor. Bypassing Complex, or Anti-Inhibitor Coagulant Complex. Indications, dosage and methods of administration of this drug are known to one of skill in the art. For additional information, see www.feiba.com.

The term "Benefix®" is a brand name for the drug Coagulation Factor IX (Recombinant). Indications, dosage and methods of administration of this drug are known to one of skill in the art. For additional information, see www.benefix.com.

The term "Kogenate® FS" is a brand name for a recombinant factor VIII product. Indications, dosage and methods of administration of this drug are known to one of skill in the art. For additional information, see www.kogenate.com.

The term "Recombinate" is a brand name for a drug that is a recombinant antihemophilic factor. Indications, dosage and methods of administration of this drug are known to one of skill in the art. For additional information, see www.recombinate.com.

The term "Advate®" designates a drug that is a recombinant antihemophilic factor, used to replace clotting factor VIII. Indications, dosage and methods of administration of this drug are known to one of skill in the art. For additional information, see www.advate.com.

The term "Helixate FS" is a brand name for a drug that is a recombinant factor VIII treatment. Indications, dosage and methods of administration of this drug are known to one of skill in the art. For additional information, see www.helixatefs.com.

The term "Koāte®-DVI" is a brand name for a drug that is a human antihemophilic factor treatment. Indications, dosage and methods of administration of this drug are known to one of skill in the art. For additional information, see www.koate-dvi.com/.

The term "Stimate®" is a brand of desmopressin used to help stop bleeding in patients with von Willebrand's disease or mild hemophilia A. Indications, dosage and methods of administration of this drug are known to one of skill in the art. For additional information, see www.stimate.com/.

The term "DDAVP®" is a brand of desmopressin used to help stop bleeding in patients with von Willebrand's disease or mild hemophilia A. Indications, dosage and methods of administration of this drug are known to one of skill in the art.

The term "Bebulin" designates the drug Factor IX Complex. Indications, dosage and methods of administration of this drug are known to one of skill in the art. For additional information, see www.baxter.com.

The term "Hemofil M®" is a brand of antihemophilic human factor VIII. Indications, dosage and methods of administration of this drug are known to one of skill in the art. For additional information, see www.baxter.com.

In one embodiment, the alternative therapy is recombinant porcine FVIII. In another embodiment, the alternative therapy is recombinant FV variants. In one embodiment, the alternative therapy is recombinant FVIIa variants. In one embodiment, the alternative therapy is recombinant FXa variants. In another embodiment, the alternative therapy is FXIII. In one embodiment, the alternative therapy is prothrombin. In one embodiment, the alternative therapy is fibrinogen. In another embodiment, the alternative therapy is a mix of coagulation factors. In one embodiment, the alternative therapy is antibodies mimicking FVIII. In one embodiment, the alternative therapy is peptides mimicking FVIII. In another embodiment, the alternative therapy is compounds mimicking FVIII. In one embodiment, the alternative therapy is peptide inhibitors of TFPI. In another embodiment, the alternative therapy is antibody inhibitors of TFPI. In one embodiment, the alternative therapy is compounds inhibiting TFPI. In another embodiment, the alternative therapy is compounds inhibiting anti-coagulant proteins.

In one embodiment, the alternative therapy is a therapy that is used for treating a bleeding disorder and that is not rFVIIa, as determined by a person of skill in the art. In one embodiment, the alternative therapy is a therapy that is used for treating a bleeding disorder and that is not rFVIIa as a single agent, as determined by a person of skill in the art. In another embodiment, the alternative therapy is a therapy used for treating a bleeding disorder and that does not comprise rFVIIa, as determined by a person of skill in the art. For additional information on therapies to treat bleeding disorders, including dosage and administration, see e.g., The Absite Review, by Steven M. Fiser, Lippincott Williams and Wilkins 2004.

In one embodiment, the alternative therapy is a coagulation factor that is not recombinant rFVIIa, or a variant of a coagulation factor that is not recombinant rFVIIa, including, but not limited, to FI (fibrinogen), FII (prothrombin), FIII (tissue factor), FIV, FV, FVa, FVIII, FIX, FX, FXa, FXI, FXIII, von Willebrand factor, prekallikrein, or high-molecular weight kininogen. In one embodiment, the coagulation factor is a recombinant coagulation factor that is not recombinant rFVIIa. In another embodiment, the coagulation factor is a non-recombinant coagulation factor. In one embodiment, the coagulation factor is an activated coagulation factor. In another embodiment, the coagulation factor is a non-activated coagulation factor. In one embodiment the alternative therapy is a mixture of coagulation factors. In another embodiment, the mixture of coagulation factors can include, but is not limited to, one, two, three, or more coagulation factors. In one embodiment the alternative therapy is a mixture of recombinant, activated or non-activated coagulation factors.

In one embodiment, the alternative therapy is a molecule that can mimic a coagulation factor. In another embodiment, the alternative therapy is a molecule that can mimic the activity of a coagulation factor. In further embodiment, the alternative therapy is a molecule which has procoagulation activity. In a further embodiment, the alternative therapy can be a mixture of molecules that mimic coagulation factors, or the activity of coagulation factors. In one embodiment, the molecule is a small molecule. In another embodiment, the molecule is a peptide. In one embodiment, the molecule is an antibody or a fragment thereof.

In one embodiment, the alternative therapy is an inhibitor of an anti-coagulant. In one embodiment, the inhibitor can include, but is not limited to, a small molecule, a peptide, or an antibody. In one embodiment the anti-coagulant can include, but is not limited to protein C, heparin cofactor II, heparin cofactor III, anti-thrombin, protein Z, protein S, protein Z-related protease inhibitor, plasminogen, alpha 2-antiplasmin, tissue plasminogen activator, urokinase, plasminogen activator inhibitor-1, plasminogen activator inhibitor-2, or cancer procoagulant. In a further embodiment, the alternative therapy can be a mixture of inhibitors of an anti-coagulant.

In one embodiment, the subject is an animal. In another embodiment, the subject is an animal that has or is diagnosed with a bleeding disorder. In one embodiment, the subject is an animal that is predisposed to or is at risk of developing a bleeding disorder. In other embodiments, the subject is a human. In other embodiments, the subject is a mammal. In some embodiments, the subject is a rodent, such as a mouse or a rat. In some embodiments, the subject is a cow, pig, sheep, goat, cat, horse, dog, and/or any other species of animal used as livestock or kept as pets.

In some embodiments, the subject is already suspected to have a bleeding disorder. In other embodiments, the subject is being treated for a bleeding disorder, before being treated according to the methods of the invention. In other embodiments, the subject is not being treated for a bleeding disorder, before being treated according to the methods of the invention.

In one embodiment, the subject has a risk of thrombosis. In another embodiment, the subject does not have a risk of thrombosis. In one embodiment, the subject has an unacceptable risk of thrombosis. In another embodiment, the subject does not have an unacceptable risk of thrombosis.

In another aspect, the present invention provides a method of treating a bleeding disorder in a subject in need thereof, the method comprising administering a therapeutically effective amount of rFVIIa to the subject, wherein (a) a sample of platelets derived from the subject was obtained; (b) a platelet population from the sample was incubated with rFVIIa; and (c) platelets having a high binding capacity to rFVIIa, as compared to the binding capacity to rFVIIa of a control platelet population, were detected in the platelet population.

In another aspect, the present invention provides a method of treating a bleeding disorder in a subject in need thereof, the method comprising administering a therapeutically effective amount of rFVIIa to the subject, wherein (a) a sample of platelets derived from the subject was obtained; (b) a platelet population from the sample was incubated with rFVIIa; and (c) platelets having a low binding capacity to rFVIIa, as compared to the binding capacity to rFVIIa of a control platelet population, were detected in the platelet population.

In another aspect, the present invention provides a method of treating a bleeding disorder in a subject in need thereof, the method comprising administering a therapeutically effective amount of an alternative therapy to the subject, wherein (a) a sample of platelets derived from the subject was obtained; (b) a platelet population from the sample was incubated with rFVIIa; and (c) platelets having a high binding capacity to rFVIIa, as compared to the binding capacity to rFVIIa of a control platelet population, were detected in the platelet population.

In another aspect, the present invention provides a method of treating a bleeding disorder in a subject in need thereof, the method comprising administering a therapeutically effective amount of an alternative therapy to the subject, wherein (a) a sample of platelets derived from the subject was obtained; (b) a platelet population from the sample was incubated with rFVIIa; and (c) platelets having a low binding capacity to rFVIIa, as compared to the binding capacity to rFVIIa of a control platelet population, were detected in the platelet population.

In one embodiment, the detection is by flow cytometry. In another embodiment, the detection is by immunofluorescence. In yet another embodiment, the detection is by microscopy, such as, but not limited to, electron microscopy or confocal laser scanning microscopy (CLSM or LSCM). In a further embodiment, the detection is by an immunoassay, such as, but not limited to, cell-based enzyme-linked immunosorbent assay. In another embodiment, the detection is by any method known to one skill in the art that would detect rFVIIa bound platelets.

In one embodiment, the binding capacity to rFVIIa of platelets is measured through detection of fluorescence intensity. In one embodiment, the fluorescence intensity is proportional to the amount of rFVIIa bound to the platelets.

In one embodiment, the platelets are activated. In another embodiment, the platelets are non-activated. In one embodiment, the platelets are coated. In another embodiment, the platelets are not coated.

In one embodiment, the control platelet population is a platelet population not exposed to rFVIIa. In another embodiment, the control platelet population is a platelet population exposed to rFVIIa. In one embodiment, the concentration of rFVIIa is about 5 nM, 10 nM, 20 nM, 30 nM, 40 nM, 50 nM, 100 nM, 200 nM, 300 nM, 400 nM, 500 nM, 600 nM, 700 nM, 800 nM, 900 nM, 1000 nM, 1100 nM, 1200 nM, 1300 nM, 1400 nM, 1500 nM, 1600 nM, 1700 nM, 1800 nM, 1900 nM, 2000 nM, 3000 nM, 4000 nM, 5000 nM, 6000 nM, or more.

In one embodiment the control platelet population has a rFVIIa binding constant of about 200 nM. In one embodiment, the control platelet population has a rFVIIa binding constant of about 25 to 1100 nM. In another embodiment, the control platelet population has a rFVIIa binding constant of about 50 to 400 nM. In further embodiments, the control platelet population has a rFVIIa binding constant of about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 1100 nM, about 1200 nM, about 1300 nM, about 1400 nM, about 1500 nM, about 1600 nM, about 1700 nM, about 1800 nM, about 1900 nM, about 2000 nM, about 3000 nM, about 4000 nM, or about 5000 nM, about 6000 nM, about 7000 nM, about 8000 nM, about 9000 nM, about 10,000 nM, or more.

In other embodiments, the control platelet population has a rFVIIa binding constant of about 10 nM to 30 nM, about 20 nM to 40 nM, about 30 nM to 50 nM, about 40 nM to 60 nM, about 50 nM to 70 nM, about 60 nM to 80 nM, about 70 nM to 90 nM, about 80 nM to 100 nM, 90 nM to 110 nM, about 100 nM to 120 nM, about 110 nM to 130 nM, about 120 nM to 140 nM, about 130 nM to 150 nM, about 140 nM to 160 nM, about 150 nM to 170 nM, about 160 nM to 180 nM, about 170 nM to 190 nM, about 180 nM to 200 nM, about 190 nM to 210 nM, about 200 nM to 220 nM, about 210 nM to 230 nM, about 220 nM to 240 nM, about 230 nM to 250 nM, about 240 nM to 260 nM, about 250 nM to 270 nM, about 260 nM to 280 nM, about 270 nM to 290 nM, about 280 nM to 300 nM, about 290 nM to 310 nM, about 300 nM to 320 nM, about 310 nM to 330 nM, about 320 nM to 340 nM, about 330 nM to 350 nM, about 340 nM to 360 nM, about 350 nM to 370 nM, about 360 nM to 380 nM, about 370 nM to 390 nM, about 380 nM to 400 nM, about 390 nM to 410 nM, about 400 nM to 450 nM, about 450 nM to 500 nM, about 500 nM to 550 nM, about 550 nM to 600 nM, about 600 nM to 650 nM, about 650 nM to 700 nM, about 700 nM to 750 nM, about 750 nM to 800 nM, about 800 nM to 850 nM, about 850 nM to 900 nM, about 900 nM to 950 nM, about 950 nM to 1000 nM, about 1000 nM to 1050 nM, about 1050 nM to 1100 nM, about 1100 nM to 1150 nM, about 1150 nM to 1200 nM, about 1200 nM to 1250 nM, about 1250 nM to 1300 nM, about 1300 nM to 1350 nM, about 1350 nM to 1400 nM, about 1400 nM to 1450 nM, or about 1450 nM to 1500 nM, or any range in between.

In one embodiment, the platelets having a high binding capacity to rFVIIa have about a 25-fold higher binding capacity to rFVIIa, as compared to the binding capacity to rFVIIa of a control platelet population. In another embodiment, the platelets having a high binding capacity to rFVIIa have about a 35-fold higher binding capacity to rFVIIa, as compared to the binding capacity to rFVIIa of a control platelet population.

In one embodiment, the platelets having a high binding capacity to rFVIIa have about a 0.1-fold, 0.15-fold, 0.2-fold, 0.25-fold, 0.3-fold, 0.4-fold, 0.5 fold, 0.6-fold, 0.7-fold, 0.8-fold, 0.9-fold, 1-fold, 1.5-fold, 2 fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, or about a 9-fold higher binding capacity to rFVIIa, as compared to the binding capacity to rFVIIa of a control platelet population.

In another embodiment, the platelets having a high binding capacity to rFVIIa have about a 10-fold, 11-fold, 12 fold, 13-fold, 14-fold, 15-fold, 16-fold, 17-fold, 18-fold, or a 19-fold higher binding capacity to rFVIIa, as compared to the binding capacity to rFVIIa of a control platelet population.

In one embodiment, the platelets having a high binding capacity to rFVIIa have about a 20-fold, 21-fold, 22-fold, 23-fold, 24-fold, 25-fold, 26-fold, 27-fold, 28-fold, or a 29-fold higher binding capacity to rFVIIa, as compared to the binding capacity to rFVIIa of a control platelet population.

In another embodiment, the platelets having a high binding capacity to rFVIIa have about a 30-fold, 31-fold, 32-fold, 33-fold, 34-fold, 35-fold, 36-fold, 37-fold, 38-fold, or a 39-fold higher binding capacity to rFVIIa, as compared to the binding capacity to rFVIIa of a control platelet population.

In one embodiment, the platelets having a high binding capacity to rFVIIa have about a 40-fold, 41-fold, 42-fold, 43-fold, 44-fold, 45-fold, 46-fold, 47-fold, 48-fold, or a 49-fold higher binding capacity to rFVIIa, as compared to the binding capacity to rFVIIa of a control platelet population.

In another embodiment, the platelets having a high binding capacity to rFVIIa have about a 50-fold, 51-fold, 52-fold, 53-fold, 54-fold, 55-fold, 56-fold, 57-fold, 58-fold, 59-fold, 60-fold, 70-fold, 80-fold, 90-fold, 100-fold, 150-fold, 200-fold, 250-fold, 300-fold, 350-fold, 400 fold, 450-fold, or about a 500-fold higher binding capacity to rFVIIa, as compared to the binding capacity to rFVIIa of a control platelet population.

In another embodiment, the platelets having a high binding capacity to rFVIIa have about a 0.1-fold to 0.3-fold, 0.2-fold to 0.4-fold, 0.3-fold to 0.5-fold, 0.4-fold to 0.6-fold, 0.5-fold to 0.7-fold, 0.6-fold to 0.8-fold, 0.7-fold to 0.9-fold, 0.8-fold to 1.0-fold, 0.9-fold to 1.1-fold, 1-fold to 1.5-fold, 1.25-fold to 1.75-fold, 1.5-fold to 2-fold, 1.75-fold to 2.25-fold, 2-fold to 2.5-fold, 2.25-fold to 2.75-fold, 2.5-fold to 3-fold, 2.75-fold to 3.25-fold, 3-fold to 4-fold, 3.5-fold to 4.5-fold, 4-fold to 5-fold, 4.5-fold to 5.5-fold, 5-fold to 6-fold, 6-fold to 8-fold, 8-fold to 10-fold, 10-fold to 12-fold, 12-fold to 14-fold, 14-fold to 16-fold, 16-fold to 18-fold, 18-fold to 20-fold, 20-fold to 25-fold, 25-fold to 3-fold, 30-fold to 40-fold, 40-fold to 50-fold, 50-fold to 70-fold, 70-fold to 90-fold, 90-fold to 100-fold, 100-fold to 120-fold, 120-fold to 140-fold, 140-fold to 160-fold, 1-fold to 20-fold, 10-fold to 30-fold, 20-fold to 40-fold, 30-fold to 50-fold, 40-fold to 60-fold, 50-fold to 80-fold, 60-fold to 80-fold, 70-fold to 90-fold, 80-fold to 100-fold, 100-fold to 150-fold, 130-fold to 180-fold, or any range in between, higher binding capacity to rFVIIa, as compared to the binding capacity to rFVIIa of a control platelet population.

In another embodiment, the platelets having a high binding capacity to rFVIIa have about a 50%, 75%, 100%, 125%, 150%, 175%, 200%, 300%, 400%, or a 500% higher binding capacity to rFVIIa, as compared to the binding capacity to rFVIIa of a control platelet population.

In one embodiment, the platelets having a low binding capacity to rFVIIa have about a 5-fold higher binding capacity to rFVIIa, as compared to the binding capacity to rFVIIa of a control platelet population. In another embodiment, the platelets having a low binding capacity to rFVIIa have about a 10-fold higher binding capacity to rFVIIa, as compared to the binding capacity to rFVIIa of a control platelet population.

In one embodiment, the platelets having a low binding capacity to rFVIIa have about a 0.1-fold, 0.15-fold, 0.2-fold, 0.25-fold, 0.3-fold, 0.4-fold, 0.5 fold, 0.6-fold, 0.7-fold, 0.8-fold, 0.9-fold, 1-fold, 1.5-fold, 2 fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, or about a 9-fold higher binding capacity to rFVIIa, as compared to the binding capacity to rFVIIa of a control platelet population.

In another embodiment, the platelets having a low binding capacity to rFVIIa have about a 10-fold, 11-fold, 12 fold, 13-fold, 14-fold, 15-fold, 16-fold, 17-fold, 18-fold, or a 19-fold higher binding capacity to rFVIIa, as compared to the binding capacity to rFVIIa of a control platelet population.

In one embodiment, the platelets having a low binding capacity to rFVIIa have about a 20-fold, 21-fold, 22-fold, 23-fold, 24-fold, 25-fold, 26-fold, 27-fold, 28-fold, or a 29-fold higher binding capacity to rFVIIa, as compared to the binding capacity to rFVIIa of a control platelet population.

In another embodiment, the platelets having a low binding capacity to rFVIIa have about a 30-fold, 31-fold, 32-fold, 33-fold, 34-fold, 35-fold, 36-fold, 37-fold, 38-fold, or a 39-fold higher binding capacity to rFVIIa, as compared to the binding capacity to rFVIIa of a control platelet population.

In one embodiment, the platelets having a low binding capacity to rFVIIa have about a 40-fold, 41-fold, 42-fold, 43-fold, 44-fold, 45-fold, 46-fold, 47-fold, 48-fold, or a 49-fold higher binding capacity to rFVIIa, as compared to the binding capacity to rFVIIa of a control platelet population.

In another embodiment, the platelets having a low binding capacity to rFVIIa have about a 50-fold, 51-fold, 52-fold, 53-fold, 54-fold, 55-fold, 56-fold, 57-fold, 58-fold, 59-fold, 60-fold, 70-fold, 80-fold, 90-fold, 100-fold, 150-fold, 200-fold, 250-fold, 300-fold, 350-fold, 400-fold, 450-fold, or about a 500-fold higher binding capacity to rFVIIa, as compared to the binding capacity to rFVIIa of a control platelet population.

In another embodiment, the platelets having a low binding capacity to rFVIIa have about a 0.1-fold to 0.3-fold, 0.2-fold to 0.4-fold, 0.3-fold to 0.5-fold, 0.4-fold to 0.6-fold, 0.5-fold to 0.7-fold, 0.6-fold to 0.8-fold, 0.7-fold to 0.9-fold, 0.8-fold to 1.0-fold, 0.9-fold to 1.1-fold, 1-fold to 1.5-fold, 1.25-fold to 1.75-fold, 1.5-fold to 2-fold, 1.75-fold to 2.25-fold, 2-fold to 2.5-fold, 2.25-fold to 2.75-fold, 2.5-fold to 3-fold, 2.75-fold to 3.25-fold, 3-fold to 4-fold, 3.5-fold to 4.5-fold, 4-fold to 5-fold, 4.5-fold to 5.5-fold, 5-fold to 6-fold, 6-fold to 8-fold, 8-fold to 10-fold, 10-fold to 12-fold, 12-fold to 14-fold, 14-fold to 16-fold, 16-fold to 18-fold, 18-fold to 20-fold, 20-fold to 25-fold, 25-fold to 3-fold, 30-fold to 40-fold, 40-fold to 50-fold, 50-fold to 70-fold, 70-fold to 90-fold, 90-fold to 100-fold, 100-fold to 120-fold, 120-fold to 140-fold, 140-fold to 160-fold, 1-fold to 20-fold, 10-fold to 30-fold, 20-fold to 40-fold, 30-fold to 50-fold, 40-fold to 60-fold, 50-fold to 80-fold, 60-fold to 80-fold, 70-fold to 90-fold, 80-fold to 100-fold, 100-fold to 150-fold, 130-fold to 180-fold, or any range in between, higher binding capacity to rFVIIa, as compared to the binding capacity to rFVIIa of a control platelet population.

In another embodiment, the platelets having a low binding capacity to rFVIIa have about a 50%, 75%, 100%, 125%, 150%, 175%, 200%, 300%, 400%, or a 500% higher binding capacity to rFVIIa, as compared to the binding capacity to rFVIIa of a control platelet population.

In one embodiment, the sample of platelets is obtained from a blood sample or a serum sample from the subject. In another embodiment, the sample of platelets is a fresh sample, a concentrate, a preserved sample, a rehydrated lyophilized sample, or a frozen sample.

In one embodiment, the bleeding disorder is hemophilia. In one embodiment, the hemophilia is hemophilia A or hemophilia B. In another embodiment, the hemophilia A is congenital hemophilia A with inhibitors or acquired hemophilia A with inhibitory auto antibodies to FVIII, and the hemophilia B is congenital hemophilia B with inhibitors or acquired hemophilia B with inhibitory auto antibodies to FIX.

In one embodiment, the subject does not have an unacceptable risk of thrombosis. In another embodiment, the subject has an unacceptable risk of thrombosis.

In one embodiment, the bleeding disorder is a non-hemophilia bleeding disorder. In one embodiment, the non-hemophilia bleeding disorder is blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease or von Willebrand disease with inhibitors to von Willebrand factor.

In one embodiment, the alternative therapy is Prothrombin Complex Concentrate or activated Prothrombin Complex Concentrate. In one embodiment, the activated Prothrombin Complex Concentrate is FEIBA.

In one embodiment, the alternative therapy is BeneFix®, Kogenate® FS, Recombinate, Advate®, Helixate® FS, Koāte®-DVI, Stimate®, DDAVP®, Bebulin, Hemofil M®, cryoprecipitated antihaemophilic factor (AHF), or fresh frozen plasma (FFP).

In another embodiment, the alternative therapy is recombinant porcine FVIII, recombinant FV variants, recombinant FVIIa variants, recombinant FXa variants, FXIII, prothrombin, fibrinogen, a mix of coagulation factors, antibodies mimicking FVIII, peptides mimicking FVIII, compounds mimicking FVIII, peptide inhibitors of TFPI, antibody inhibitors of TFPI, compounds inhibiting TFPI or compounds inhibiting anti-coagulant proteins.

In one embodiment, the subject is a human.

2. Isolated Platelet Subpopulation

In another aspect, the present invention provides a subpopulation of platelets isolated from a platelet population, wherein the platelets in the subpopulation of platelets have at least a 4-fold higher binding capacity to rFVIIa as compared to the binding capacity to rFVIIa of the other platelets in the platelet population.

In one embodiment, the higher binding capacity to rFVIIa is determined by flow cytometry. In another embodiment, the higher binding capacity to rFVIIa is determined by immunofluorescence. In yet another embodiment, the higher binding capacity to rFVIIa is determined by microscopy, such as, but not limited to, electron microscopy or confocal laser scanning microscopy (CLSM or LSCM). In a further embodiment, the higher binding capacity to rFVIIa is determined by an immunoassay, such as, but not limited to, cell-based enzyme-linked immunosorbent assay. In another embodiment, the higher binding capacity to rFVIIa is determined by any method known to one skill in the art that would detect rFVIIa bound platelets.

In one embodiment, the binding capacity to rFVIIa of platelets in a platelet population or in a subpopulation of platelets is measured through detection of fluorescence intensity. In one embodiment, the fluorescence intensity is proportional to the amount of rFVIIa bound to the platelets.

In one embodiment, the platelets in the platelet population are activated. In another embodiment, the platelets in the platelet population are non-activated. In one embodiment, the platelets in the platelet population are coated. In another embodiment, the platelets in the platelet population are not coated.

In one embodiment, the platelets in the subpopulation of platelets are activated. In another embodiment, the platelets in the subpopulation of platelets are non-activated. In one embodiment, the platelets in the subpopulation of platelets are coated. In another embodiment, the platelets in the subpopulation of platelets are not coated.

In one embodiment, the platelets in the platelet population have a rFVIIa binding constant of about 25 to 1100 nM. In another embodiment, the platelets in the platelet population have a rFVIIa binding constant of about 50 to 400 nM. In further embodiments, the platelets in the platelet population have a rFVIIa binding constant of about 10 nM, about 20 nM, about 30 nM, about 40 nM, about 50 nM, about 60 nM, about 70 nM, about 80 nM, about 90 TIM, about 100 nM, about 200 nM, about 300 nM, about 400 nM, about 500 nM, about 600 nM, about 700 nM, about 800 nM, about 900 nM, about 1000 nM, about 1100 nM, about 1200 nM, about 1300 nM, about 1400 nM, about 1500 nM, about 1600 nM, about 1700 nM, about 1800 nM, about 1900 nM, about 2000 nM, about 3000 nM, about 4000 nM, or about 5000 nM, about 6000 nM, about 7000 nM, about 8000 nM, about 9000 nM, about 10,000 nM, or more.

In other embodiments, the platelets in the platelet population have a rFVIIa binding constant of about 10 nM to 30 nM, about 20 nM to 40 nM, about 30 nM to 50 nM, about 40 nM to 60 nM, about 50 nM to 70 nM, about 60 nM to 80 nM, about 70 nM to 90 nM, about 80 nM to 100 nM, 90 nM to 110 nM, about 100 nM to 120 nM, about 110 nM to 130 nM, about 120 nM to 140 nM, about 130 nM to 150 nM, about 140 nM to 160 nM, about 150 nM to 170 nM, about 160 nM to 180 nM, about 170 nM to 190 nM, about 180 nM to 200 nM, about 190 nM to 210 nM, about 200 nM to 220 nM, about 210 nM to 230 nM, about 220 nM to 240 nM, about 230 nM to 250 nM, about 240 nM to 260 nM, about 250 nM to 270 nM, about 260 nM to 280 nM, about 270 nM to 290 nM, about 280 nM to 300 nM, about 290 nM to 310 nM, about 300 nM to 320 nM, about 310 nM to 330 nM, about 320 nM to 340 nM, about 330 nM to 350 nM, about 340 nM to 360 nM, about 350 nM to 370 nM, about 360 nM to 380 nM, about 370 nM to 390 nM, about 380 nM to 400 nM, about 390 nM to 410 nM, about 400 nM to 450 nM, about 450 nM to 500 nM, about 500 nM to 550 nM, about 550 nM to 600 nM, about 600 nM to 650 nM, about 650 nM to 700 nM, about 700 nM to 750 nM, about 750 nM to 800 nM, about 800 nM to 850 nM, about 850 nM to 900 nM, about 900 nM to 950 nM, about 950 nM to 1000 nM, about 1000 nM to 1050 nM, about 1050 nM to 1100 nM, about 1100 nM to 1150 nM, about 1150 nM to 1200 nM, about 1200 nM to 1250 nM, about 1250 nM to 1300 nM, about 1300 nM to 1350 nM, about 1350 nM to 1400 nM, about 1400 nM to 1450 nM, or about 1450 nM to 1500 nM, or any range in between.

In other embodiments, the platelets in the subpopulation of platelets have a rFVIIa binding constant of about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 1100 nM, about 1200 nM, about 1300 nM, about 1400 nM, about 1500 nM, about 1600 nM, about 1700 nM, about 1800 nM, about 1900 nM, about 2000 nM, about 3000 nM, about 4000 nM, about 5000 nM, about 6000 nM, about 7000 nM, about 8000 nM, about 9000 nM, about 10,000 nM, or more.

In other embodiments, the platelets in the subpopulation of platelets have a rFVIIa binding constant of about 10 nM to 30 nM, about 20 nM to 40 nM, about 30 nM to 50 nM, about 40 nM to 60 nM, about 50 nM to 70 nM, about 60 nM to 80 nM, about 70 nM to 90 nM, about 80 nM to 100 nM, 90 nM to 110 nM, about 100 nM to 120 nM, about 110 nM to 130 nM, about 120 nM to 140 nM, about 130 nM to 150 nM, about 140 nM to 160 nM, about 150 nM to 170 nM, about 160 nM to 180 nM, about 170 nM to 190 nM, about 180 nM to 200 nM, about 190 nM to 210 nM, about 200 nM to 220 nM, about 210 nM to 230 nM, about 220 nM to 240 nM, about 230 nM to 250 nM, about 240 nM to 260 nM, about 250 nM to 270 nM, about 260 nM to 280 nM, about 270 nM to 290 nM, about 280 nM to 300 nM, about 290 nM to 310 nM, about 300 nM to 320 nM, about 310 nM to 330 nM, about 320 nM to 340 nM, about 330 nM to 350 nM, about 340 nM to 360 nM, about 350 nM to 370 nM, about 360 nM to 380 nM, about 370 nM to 390 nM, about 380 nM to 400 nM, about 390 nM to 410 nM, about 400 nM to 450 nM, about 450 nM to 500 nM, about 500 nM to 550 nM, about 550 nM to 600 nM, about 600 nM to 650 nM, about 650 nM to 700 nM, about 700 nM to 750 nM, about 750 nM to 800 nM, about 800 nM to 850 nM, about 850 nM to 900 nM, about 900 nM to 950 nM, about 950 nM to 1000 nM, about 1000 nM to 1050 nM, about 1050 nM to 1100 nM, about 1100 nM to 1150 nM, about 1150 nM to 1200 nM, about 1200 nM to 1250 nM, about 1250 nM to 1300 nM, about 1300 nM to 1350 nM, about 1350 nM to 1400 nM, about 1400 nM to 1450 nM, or about 1450 nM to 1500 nM, or any range in between.

In one embodiment, the platelets in the platelet population have about a 0.1-fold, 0.15-fold, 0.2-fold, 0.25-fold, 0.3-fold, 0.4-fold, 0.5-fold, 0.6-fold, 0.7-fold, 0.8-fold, 0.9-fold, 1-fold, 1.5-fold, 2 fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, or about a 9-fold higher binding capacity to rFVIIa, as compared to the binding capacity to rFVIIa of platelets in a control platelet population.

In another embodiment, the platelets in the platelet population have about a 10-fold, 11-fold, 12 fold, 13-fold, 14-fold, 15-fold, 16-fold, 17-fold, 18-fold, or a 19-fold higher binding capacity to rFVIIa, as compared to the binding capacity to rFVIIa of platelets in a control platelet population.

In one embodiment, the platelets in the platelet population have about a 20-fold, 21-fold, 22-fold, 23-fold, 24-fold, 25-fold, 26-fold, 27-fold, 28-fold, or a 29-fold higher binding capacity to rFVIIa, as compared to the binding capacity to rFVIIa of platelets in a control platelet population.

In another embodiment, the platelets in the platelet population have about a 30-fold, 31-fold, 32-fold, 33-fold, 34-fold, 35-fold, 36-fold, 37-fold, 38-fold, or a 39-fold higher binding capacity to rFVIIa, as compared to the binding capacity to rFVIIa of platelets in a control platelet population.

In another embodiment, the platelets in the platelet population have about a 40-fold, 41 fold, 42-fold, 43-fold, 44-fold, 45-fold, 46-fold, 47-fold, 48-fold, or a 49-fold higher binding capacity to rFVIIa, as compared to the binding capacity to rFVIIa of platelets in a control platelet population.

In another embodiment, the platelets in the platelet population have about a 50-fold, 51-fold, 52-fold, 53-fold, 54-fold, 55-fold, 56-fold, 57-fold, 58-fold, 59-fold, 60-fold, 70-fold, 80-fold, 90-fold, 100-fold, 150-fold, 200-fold, 250-fold, 300-fold, 350-fold, 400-fold, 450-fold, or about a 500-fold higher binding capacity to rFVIIa, as compared to the binding capacity to rFVIIa of platelets in a control platelet population.

In another embodiment, the platelets in the platelet population have about a 4-fold to 33-fold higher binding capacity, as compared to the binding capacity to rFVIIa of platelets in a control platelet population. In another embodiment, the platelets in the platelet population have about a 5-fold to 37-fold higher binding capacity, as compared to the binding capacity to rFVIIa of platelets in a control platelet population.

In another embodiment, the platelets in the platelet population have about a 0.3-fold to 2.4-fold higher binding capacity, as compared to the binding capacity to rFVIIa of platelets in a control platelet population. In another embodiment, the platelets in the platelet population have about a 0.3-fold to 2.5-fold higher binding capacity, as compared to the binding capacity to rFVIIa of platelets in a control platelet population.

In another embodiment, the platelets in the platelet population have about a 0.1-fold to 0.3-fold, 0.2-fold to 0.4-fold, 0.3-fold to 0.5-fold, 0.4-fold to 0.6-fold, 0.5-fold to 0.7-fold, 0.6-fold to 0.8-fold, 0.7-fold to 0.9-fold, 0.8-fold to 1.0-fold, 0.9-fold to 1.1-fold, 1-fold to 1.5-fold, 1.25-fold to 1.75-fold, 1.5-fold to 2-fold, 1.75-fold to 2.25-fold, 2-fold to 2.5-fold, 2.25-fold to 2.75-fold, 2.5-fold to 3-fold, 2.75-fold to 3.25-fold, 3-fold to 4-fold, 3.5-fold to 4.5-fold, 4-fold to 5-fold, 4.5-fold to 5.5-fold, 5-fold to 6-fold, 6-fold to 8-fold, 8-fold to 10-fold, 10-fold to 12-fold, 12-fold to 14-fold, 14-fold to 16-fold, 16-fold to 18-fold, 18-fold to 20-fold, 20-fold to 25-fold, 25-fold to 3-fold, 30-fold to 40-fold, 40-fold to 50-fold, 50-fold to 70-fold, 70-fold to 90-fold, 90-fold to 100-fold, 100-fold to 120-fold, 120-fold to 140-fold, 140-fold to 160-fold, 1-fold to 20-fold, 10-fold to 30-fold, 20-fold to 40-fold, 30-fold to 50-fold, 40-fold to 60-fold, 50-fold to 80-fold, 60-fold to 80-fold, 70-fold to 90-fold, 80-fold to 100-fold, 100-fold to 150-fold, 130-fold to 180-fold, or any range in between higher binding capacity to rFVIIa, as compared to the binding capacity to rFVIIa of platelets in a control platelet population.

In one embodiment, the platelets in the subpopulation of platelets have about a 0.1-fold, 0.15-fold, 0.2-fold, 0.25-fold, 0.3-fold, 0.4-fold, 0.5-fold, 0.6-fold, 0.7-fold, 0.8-fold, 0.9-fold, 1-fold, 1.5-fold, 2 fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, or about a 9-fold higher binding capacity to rFVIIa, as compared to the binding capacity to rFVIIa of the other platelets in the platelet population.

In another embodiment, the platelets in the subpopulation of platelets have about a 10-fold, 11-fold, 12 fold, 13-fold, 14-fold, 15-fold, 16-fold, 17-fold, 18-fold, or a 19-fold higher binding capacity to rFVIIa, as compared to the binding capacity to rFVIIa of the other platelets in the platelet population.

In one embodiment, the platelets in the subpopulation of platelets have about a 20-fold, 21-fold, 22-fold, 23-fold, 24-fold, 25-fold, 26-fold, 27-fold, 28-fold, or a 29-fold higher binding capacity to rFVIIa, as compared to the binding capacity to rFVIIa of the other platelets in the platelet population.

In another embodiment, the platelets in the subpopulation of platelets have about a 30-fold, 31-fold, 32-fold, 33-fold, 34-fold, 35-fold, 36-fold, 37-fold, 38-fold, or a 39-fold higher binding capacity to rFVIIa, as compared to the binding capacity to rFVIIa of the other platelets in the platelet population.

In one embodiment, the platelets in the subpopulation of platelets have about a 40-fold, 41-fold, 42-fold, 43-fold, 44-fold, 45-fold, 46-fold, 47-fold, 48-fold, or a 49-fold higher binding capacity to rFVIIa, as compared to the binding capacity to rFVIIa of the other platelets in the platelet population.

In another embodiment, the platelets in the subpopulation of platelets have about a 50-fold, 51-fold, 52-fold, 53-fold, 54-fold, 55-fold, 56-fold, 57-fold, 58-fold, 59-fold, 60-fold, 70-fold, 80-fold, 90-fold, 100-fold, 150-fold, 200-fold, 250-fold, 300-fold, 350-fold, 400-fold, 450-fold, or about a 500-fold higher binding capacity to rFVIIa, as compared to the binding capacity to rFVIIa of the other platelets in the platelet population.

In another embodiment, the platelets in the subpopulation of platelets have about a 0.1-fold to 0.3-fold, 0.2-fold to 0.4-fold, 0.3-fold to 0.5-fold, 0.4-fold to 0.6-fold, 0.5-fold to 0.7-fold, 0.6-fold to 0.8-fold, 0.7-fold to 0.9-fold, 0.8-fold to 1.0-fold, 0.9-fold to 1.1-fold, 1-fold to 1.5-fold, 1.25-fold to 1.75-fold, 1.5-fold to 2-fold, 1.75-fold to 2.25-fold, 2-fold to 2.5-fold, 2.25-fold to 2.75-fold, 2.5-fold to 3-fold, 2.75-fold to 3.25-fold, 3-fold to 4-fold, 3.5-fold to 4.5-fold, 4-fold to 5-fold, 4.5-fold to 5.5-fold, 5-fold to 6-fold, 6-fold to 8-fold, 8-fold to 10-fold, 10-fold to 12-fold, 12-fold to 14-fold, 14-fold to 16-fold, 16-fold to 18-fold, 18-fold to 20-fold, 20-fold to 25-fold, 25-fold to 3-fold, 30-fold to 40-fold, 40-fold to 50-fold, 50-fold to 70-fold, 70-fold to 90-fold, 90-fold to 100-fold, 100-fold to 120-fold, 120-fold to 140-fold, 140-fold to 160-fold, 1-fold to 20-fold, 10-fold to 30-fold, 20-fold to 40-fold, 30-fold to 50-fold, 40-fold to 60-fold, 50-fold to 80-fold, 60-fold to 80-fold, 70-fold to 90-fold, 80-fold to 100-fold, 100-fold to 150-fold, 130-fold to 180-fold, or any range in between, higher binding capacity to rFVIIa, as compared to the binding capacity to rFVIIa of the other platelets in the platelet population.

In another embodiment, the platelets in the subpopulation of platelets have about a 50%, 75%, 100%, 125%, 150%, 175%, 200%, 300%, 400%, or a 500% higher binding capacity to rFVIIa, as compared to the binding capacity to rFVIIa of the other platelets in the platelet population.

In one embodiment, the subpopulation of platelets with a higher binding capacity to rFVIIa, as compared to the binding capacity to rFVIIa of the other platelets in the platelet population, consists of at least 2% of the platelet population. In another embodiment, the subpopulation of platelets consists of at least 1%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 40%, 50%, or higher, of the platelet population.

In one embodiment, the subpopulation of platelets is supplied in the form of a pharmaceutical composition. In another embodiment, the pharmaceutical composition is administered systemically to a subject in need thereof.

In one embodiment, the pharmaceutical composition is used to treat a bleeding disorder. In one embodiment, the bleeding disorder is hemophilia. In one embodiment, the hemophilia is hemophilia with inhibitors. In another embodiment, the hemophilia is hemophilia without inhibitors. In a further embodiment, the hemophilia is hemophilia A. In yet another embodiment the hemophilia is hemophilia B. In one embodiment, the hemophilia is hemophilia A with inhibitors. In another embodiment, the hemophilia is hemophilia B with inhibitors. In one embodiment, the inhibitors are to Factor VIII. In another embodiment the inhibitors are to Factor IX. In another embodiment, the hemophilia is acquired hemophilia. In one embodiment, the hemophilia is congenital hemophilia A with inhibitors. In another embodiment, the hemophilia is acquired hemophilia A with inhibitory auto antibodies to FVIII. In one embodiment, the hemophilia is congenital hemophilia B with inhibitors. In another embodiment; the hemophilia is acquired hemophilia B with inhibitory auto antibodies to FIX.

In one embodiment, the bleeding disorder is a non-hemophilia bleeding disorder. In one embodiment, the bleeding disorder is blood loss from trauma. In another embodiment, the bleeding disorder is FVII deficiency. In one embodiment, the bleeding disorder is FV deficiency. In another embodiment, the bleeding disorder is FX deficiency. In one embodiment, the bleeding disorder is FXI deficiency. In one embodiment, the bleeding disorder is FXIII deficiency. In one embodiment, the bleeding disorder is fibrinogen deficiency. In one embodiment, the bleeding disorder is prothrombin deficiency. In another embodiment, the bleeding disorder is dilutional coagulopathy. In a further embodiment, the bleeding disorder is thrombocytopenia. In yet another embodiment, the bleeding disorder is blood loss from high-risk surgeries. In another embodiment, the bleeding disorder is intracerebral hemorrhage. In one embodiment, the bleeding disorder is von Willebrand disease. In a further embodiment, the bleeding disorder is von Willebrand disease with inhibitors to von Willebrand factor.

In one embodiment, the bleeding disorder is a congenital platelet function defect, including, but not limited to, platelet storage pool disorder, Glanzmann's thrombasthenia, or Bernard-Soulier syndrome. In one embodiment, the bleeding disorder is an acquired platelet function defect. In one embodiment, the bleeding disorder is a congenital deficiency of Factor II, Factor V, Factor VII, Factor X, or Factor XI. In one embodiment, the bleeding disorder is neonatal and pediatric coagulopathies. In one embodiment, the bleeding disorder is a platelet function disorder. In another embodiment, the bleeding disorder is heparin-induced thrombocytopenia. In one embodiment, the bleeding disorder is disseminated intravascular coagulation. In other embodiments, the bleeding disorder is any disorder known to one of skill in the art. For additional information on bleeding disorders, see e.g., The Absite Review, by Steven M. Fiser, Lippincott Williams and Wilkins 2004.

In one embodiment, the subject is an animal. In another embodiment, the subject is an animal that has or is diagnosed with a bleeding disorder. In one embodiment, the subject is an animal that is predisposed to or is at risk of developing a bleeding disorder. In other embodiments, the subject is a human. In other embodiments, the subject is a mammal. In some embodiments, the subject is a rodent, such as a mouse or a rat. In some embodiments, the subject is a cow, pig, sheep, goat, cat, horse, dog, and/or any other species of animal used as livestock or kept as pets.

In some embodiments, the subject is already suspected to have a bleeding disorder. In other embodiments, the subject is being treated for a bleeding disorder before being treated according to the methods of the invention. In other embodiments, the subject is not being treated for a bleeding disorder before being treated according to the methods of the invention.

3. Method of Diagnosis

In another aspect, the present invention provides a method of determining whether a subject is a candidate for treatment with rFVIIa, the method comprising (a) obtaining a sample of platelets derived from the subject; (b) incubating a platelet population from the sample with rFVIIa; and (c) detecting whether the platelet population contains a subpopulation of platelets having at least a 4-fold higher binding capacity to rFVIIa, as compared to the binding capacity to rFVIIa of the other platelets in the platelet population. Optionally, this candidate is a candidate for treatment with rFVIIa if the subject does not have an unacceptable risk of thrombosis, and if the platelet population contains a subpopulation of platelets having at least a 4-fold higher binding capacity to rFVIIa, as compared to the binding capacity to rFVIIa of the other platelets in the platelet population.

In another aspect, the present invention provides a method of determining whether a subject is a candidate for treatment with rFVIIa, the method comprising (a) obtaining a sample of platelets derived from the subject; (b) incubating a platelet population from the sample with rFVIIa; (c) detecting whether the platelet population contains a subpopulation of platelets having at least a 4-fold higher binding capacity to rFVIIa, as compared to the binding capacity to rFVIIa of the other platelets in the platelet population, wherein a subject is a candidate for treatment with rFVIIa if the subject has an unacceptable risk of thrombosis, and if the platelet population does not contain a subpopulation of platelets having at least a 4-fold higher binding capacity to rFVIIa, as compared to the binding capacity to rFVIIa of the other platelets in the platelet population.

In one embodiment, the detection is by flow cytometry. In another embodiment, the detection is by immunofluorescence. In yet another embodiment, the detection is by microscopy, such as, but not limited to, electron microscopy or confocal laser scanning microscopy (CLSM or LSCM). In a further embodiment, the detection is by an immunoassay, such as, but not limited to, cell-based enzyme-linked immunosorbent assay. In another embodiment, the detection is by any method known to one skill in the art that would detect rFVIIa bound platelets.

In one embodiment, the binding capacity to rFVIIa of platelets in a platelet population or in a subpopulation of platelets is measured through detection of fluorescence intensity. In one embodiment, the fluorescence intensity is proportional to the amount of rFVIIa bound to the platelets.

In one embodiment, the platelets in the platelet population are activated. In another embodiment, the platelets in the platelet population are non-activated. In one embodiment, the platelets in the platelet population are coated. In another embodiment, the platelets in the platelet population are not coated.

In one embodiment, the platelets in the subpopulation of platelets are activated. In another embodiment, the platelets in the subpopulation of platelets are non-activated. In one embodiment, the platelets in the subpopulation of platelets are coated. In another embodiment, the platelets in the subpopulation of platelets are not coated.

In one embodiment, the platelets in the platelet population have a rFVIIa binding constant of about 25 to 1100 nM. In another embodiment, the platelets in the platelet population have a rFVIIa binding constant of about 50 to 400 nM. In further embodiments, the platelets in the platelet population have a rFVIIa binding constant of about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 1100 nM, about 1200 nM, about 1300 nM, about 1400 nM, about 1500 nM, about 1600 nM, about 1700 nM, about 1800 nM, about 1900 nM, about 2000 nM, about 3000 nM, about 4000 nM, or about 5000 nM, about 6000 nM, about 7000 nM, about 8000 nM, about 9000 nM, about 10,000 nM, or more.

In other embodiments, the platelets in the platelet population have a rFVIIa binding constant of about 10 nM to 30 nM, about 20 nM to 40 nM, about 30 nM to 50 nM, about 40 nM to 60 nM, about 50 nM to 70 nM, about 60 nM to 80 nM, about 70 nM to 90 nM, about 80 nM to 100 nM, 90 nM to 110 nM, about 100 nM to 120 nM, about 110 nM to 130 nM, about 120 nM to 140 nM, about 130 nM to 150 nM, about 140 nM to 160 nM, about 150 nM to 170 nM, about 160 nM to 180 nM, about 170 nM to 190 nM, about 180 nM to 200 nM, about 190 nM to 210 nM, about 200 nM to 220 nM, about 210 nM to 230 nM, about 220 nM to 240 nM, about 230 nM to 250 nM, about 240 nM to 260 nM, about 250 nM to 270 nM, about 260 nM to 280 nM, about 270 nM to 290 nM, about 280 nM to 300 nM, about 290 nM to 310 nM, about 300 nM to 320 nM, about 310 nM to 330 nM, about 320 nM to 340 nM, about 330 nM to 350 nM, about 340 nM to 360 nM, about 350 nM to 370 nM, about 360 nM to 380 nM, about 370 nM to 390 nM, about 380 nM to 400 nM, about 390 nM to 410 nM, about 400 nM to 450 nM, about 450 nM to 500 nM, about 500 nM to 550 nM, about 550 nM to 600 nM, about 600 nM to 650 nM, about 650 nM to 700 nM, about 700 nM to 750 nM, about 750 nM to 800 nM, about 800 nM to 850 nM, about 850 nM to 900 nM, about 900 nM to 950 nM, about 950 nM to 1000 nM, about 1000 nM to 1050 nM, about 1050 nM to 1100 nM, about 1100 nM to 1150 nM, about 1150 nM to 1200 nM, about 1200 nM to 1250 nM, about 1250 nM to 1300 nM, about 1300 nM to 1350 nM, about 1350 nM to 1400 nM, about 1400 nM to 1450 nM, or about 1450 nM to 1500 nM, or any range in between.

In other embodiments, the platelets in the subpopulation of platelets have a rFVIIa binding constant of about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 1100 nM, about 1200 nM, about 1300 nM, about 1400 nM, about 1500 nM, about 1600 nM, about 1700 nM, about 1800 nM, about 1900 nM, about 2000 nM, about 3000 nM, about 4000 nM, about 5000 nM, about 6000 nM, about 7000 nM, about 8000 nM, about 9000 nM, about 10,000 nM, or more.

In other embodiments, the platelets in the subpopulation of platelets have a rFVIIa binding constant of about 10 nM to 30 nM, about 20 nM to 40 nM, about 30 nM to 50 nM, about 40 nM to 60 nM, about 50 nM to 70 nM, about 60 nM to 80 nM, about 70 nM to 90 nM, about 80 nM to 100 nM, 90 nM to 110 nM, about 100 nM to 120 nM, about 110 nM to 130 nM, about 120 nM to 140 nM, about 130 nM to 150 nM, about 140 nM to 160 nM, about 150 nM to 170 nM, about 160 nM to 180 nM, about 170 nM to 190 nM, about 180 nM to 200 nM, about 190 nM to 210 nM, about 200 nM to 220 nM, about 210 nM to 230 nM, about 220 nM to 240 nM, about 230 nM to 250 nM, about 240 nM to 260 nM, about 250 nM to 270 nM, about 260 nM to 280 nM, about 270 nM to 290 nM, about 280 nM to 300 nM, about 290 nM to 310 nM, about 300 nM to 320 nM, about 310 nM to 330 nM, about 320 nM to 340 nM, about 330 nM to 350 nM, about 340 nM to 360 nM, about 350 nM to 370 nM, about 360 nM to 380 nM, about 370 nM to 390 nM, about 380 nM to 400 nM, about 390 nM to 410 nM, about 400 nM to 450 nM, about 450 nM to 500 nM, about 500 nM to 550 nM, about 550 nM to 600 nM, about 600 nM to 650 nM, about 650 nM to 700 nM, about 700 nM to 750 nM, about 750 nM to 800 nM, about 800 nM to 850 nM, about 850 nM to 900 nM, about 900 nM to 950 nM, about 950 nM to 1000 nM, about 1000 nM to 1050 nM, about 1050 nM to 1100 nM, about 1100 nM to 1150 nM, about 1150 nM to 1200 nM, about 1200 nM to 1250 nM, about 1250 nM to 1300 nM, about 1300 nM to 1350 nM, about 1350 nM to 1400 nM, about 1400 nM to 1450 nM, or about 1450 nM to 1500 nM, or any range in between.

In one embodiment, the platelets in the platelet population have about a 0.1-fold, 0.15-fold, 0.2-fold, 0.25-fold, 0.3-fold, 0.4-fold, 0.5-fold, 0.6-fold, 0.7-fold, 0.8-fold, 0.9-fold, 1-fold, 1.5-fold, 2 fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, or about a 9-fold higher binding capacity to rFVIIa, as compared to the binding capacity to rFVIIa of platelets in a control platelet population.

In another embodiment, the platelets in the platelet population have about a 10-fold, 11-fold, 12 fold, 13-fold, 14-fold, 15-fold, 16-fold, 17-fold, 18-fold, or a 19-fold higher binding capacity to rFVIIa, as compared to the binding capacity to rFVIIa of platelets in a control platelet population.

In one embodiment, the platelets in the platelet population have about a 20-fold, 21-fold, 22-fold, 23-fold, 24-fold, 25-fold, 26-fold, 27-fold, 28-fold, or a 29-fold higher binding capacity to rFVIIa, as compared to the binding capacity to rFVIIa of platelets in a control platelet population.

In another embodiment, the platelets in the platelet population have about a 30-fold, 31-fold, 32-fold, 33-fold, 34-fold, 35-fold, 36-fold, 37-fold, 38-fold, or a 39-fold higher binding capacity to rFVIIa, as compared to the binding capacity to rFVIIa of platelets in a control platelet population.

In another embodiment, the platelets in the platelet population have about a 40-fold, 41-fold, 42-fold, 43-fold, 44-fold, 45-fold, 46-fold, 47-fold, 48-fold, or a 49-fold higher binding capacity to rFVIIa, as compared to the binding capacity to rFVIIa of platelets in a control platelet population.

In another embodiment, the platelets in the platelet population have about a 50-fold, 51-fold, 52-fold, 53-fold, 54-fold, 55-fold, 56-fold, 57-fold, 58-fold, 59-fold, 60-fold, 70-fold, 80-fold, 90-fold, 100-fold, 150-fold, 200-fold, 250-fold, 300-fold, 350-fold, 400-fold, 450-fold, or about a 500-fold higher binding capacity to rFVIIa, as compared to the binding capacity to rFVIIa of platelets in a control platelet population.

In another embodiment, the platelets in the platelet population have about a 4-fold to 33-fold higher binding capacity, as compared to the binding capacity to rFVIIa of platelets in a control platelet population. In another embodiment, the platelets in the platelet population have about a 5-fold to 37-fold higher binding capacity, as compared to the binding capacity to rFVIIa of platelets in a control platelet population.

In another embodiment, the platelets in the platelet population have about a 0.3-fold to 2.4-fold higher binding capacity, as compared to the binding capacity to rFVIIa of platelets in a control platelet population. In another embodiment, the platelets in the platelet population have about a 0.3-fold to 2.5-fold higher binding capacity, as compared to the binding capacity to rFVIIa of platelets in a control platelet population.

In another embodiment, the platelets in the platelet population have about a 0.1-fold to 0.3-fold, 0.2-fold to 0.4-fold, 0.3-fold to 0.5-fold, 0.4-fold to 0.6-fold, 0.5-fold to 0.7-fold, 0.6-fold to 0.8-fold, 0.7-fold to 0.9-fold, 0.8-fold to 1.0-fold, 0.9-fold to 1.1-fold, 1-fold to 1.5-fold, 1.25-fold to 1.75-fold, 1.5-fold to 2-fold, 1.75-fold to 2.25-fold, 2-fold to 2.5-fold, 2.25-fold to 2.75-fold, 2.5-fold to 3-fold, 2.75-fold to 3.25-fold, 3-fold to 4-fold, 3.5-fold to 4.5-fold, 4-fold to 5-fold, 4.5-fold to 5.5-fold, 5-fold to 6-fold, 6-fold to 8-fold, 8-fold to 10-fold, 10-fold to 12-fold, 12-fold to 14-fold, 14-fold to 16-fold, 16-fold to 18-fold, 18-fold to 20-fold, 20-fold to 25-fold, 25-fold to 3-fold, 30-fold to 40-fold, 40-fold to 50-fold, 50-fold to 70-fold, 70-fold to 90-fold, 90-fold to 100-fold, 100-fold to 120-fold, 120-fold to 140-fold, 140-fold to 160-fold, 1-fold to 20-fold, 10-fold to 30-fold, 20-fold to 40-fold, 30-fold to 50-fold, 40-fold to 60-fold, 50-fold to 80-fold, 60-fold to 80-fold, 70-fold to 90-fold, 80-fold to 100-fold, 100-fold to 150-fold, 130-fold to 180-fold, or any range in between higher binding capacity to rFVIIa, as compared to the binding capacity to rFVIIa of platelets in a control platelet population.

In one embodiment, the platelets in the subpopulation of platelets have about a 0.1-fold, 0.15-fold, 0.2-fold, 0.25-fold, 0.3-fold, 0.4-fold, 0.5-fold, 0.6-fold, 0.7-fold, 0.8-fold, 0.9-fold, 1-fold, 1.5-fold, 2 fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, or about a 9-fold higher binding capacity to rFVIIa, as compared to the binding capacity to rFVIIa of the other platelets in the platelet population.

In another embodiment, the platelets in the subpopulation of platelets have about a 10-fold, 11-fold, 12 fold, 13-fold, 14-fold, 15-fold, 16-fold, 17-fold, 18-fold, or a 19-fold higher binding capacity to rFVIIa, as compared to the binding capacity to rFVIIa of the other platelets in the platelet population.

In one embodiment, the platelets in the subpopulation of platelets have about a 20-fold, 21-fold, 22-fold, 23-fold, 24-fold, 25-fold, 26-fold, 27-fold, 28-fold, or a 29-fold higher binding capacity to rFVIIa, as compared to the binding capacity to rFVIIa of the other platelets in the platelet population.

In another embodiment, the platelets in the subpopulation of platelets have about a 30-fold, 31-fold, 32-fold, 33-fold, 34-fold, 35-fold, 36-fold, 37-fold, 38-fold, or a 39-fold higher binding capacity to rFVIIa, as compared to the binding capacity to rFVIIa of the other platelets in the platelet population.

In one embodiment, the platelets in the subpopulation of platelets have about a 40-fold, 41-fold, 42-fold, 43-fold, 44-fold, 45-fold, 46-fold, 47-fold, 48-fold, or a 49-fold higher binding capacity to rFVIIa, as compared to the binding capacity to rFVIIa of the other platelets in the platelet population.

In another embodiment, the platelets in the subpopulation of platelets have about a 50-fold, 51-fold, 52-fold, 53-fold, 54-fold, 55-fold, 56-fold, 57-fold, 58-fold, 59-fold, 60-fold, 70-fold, 80-fold, 90-fold, 100-fold, 150-fold, 200-fold, 250-fold, 300-fold, 350-fold, 400-fold, 450-fold, or about a 500-fold higher binding capacity to rFVIIa, as compared to the binding capacity to rFVIIa of the other platelets in the platelet population.

In another embodiment, the platelets in the subpopulation of platelets have about a 0.1-fold to 0.3-fold, 0.2-fold to 0.4-fold, 0.3-fold to 0.5-fold, 0.4-fold to 0.6-fold, 0.5-fold to 0.7-fold, 0.6-fold to 0.8-fold, 0.7-fold to 0.9-fold, 0.8-fold to 1.0-fold, 0.9-fold to 1.1-fold, 1-fold to 1.5-fold, 1.25-fold to 1.75-fold, 1.5-fold to 2-fold, 1.75-fold to 2.25-fold, 2-fold to 2.5-fold, 2.25-fold to 2.75-fold, 2.5-fold to 3-fold, 2.75-fold to 3.25-fold, 3-fold to 4-fold, 3.5-fold to 4.5-fold, 4-fold to 5-fold, 4.5-fold to 5.5-fold, 5-fold to 6-fold, 6-fold to 8-fold, 8-fold to 10-fold, 10-fold to 12-fold, 12-fold to 14-fold, 14-fold to 16-fold, 16-fold to 18-fold, 18-fold to 20-fold, 20-fold to 25-fold, 25-fold to 3-fold, 30-fold to 40-fold, 40-fold to 50-fold, 50-fold to 70-fold, 70-fold to 90-fold, 90-fold to 100-fold, 100-fold to 120-fold, 120-fold to 140-fold, 140-fold to 160-fold, 1-fold to 20-fold, 10-fold to 30-fold, 20-fold to 40-fold, 30-fold to 50-fold, 40-fold to 60-fold, 50-fold to 80-fold, 60-fold to 80-fold, 70-fold to 90-fold, 80-fold to 100-fold, 100-fold to 150-fold, 130-fold to 180-fold, or any range in between, higher binding capacity to rFVIIa, as compared to the binding capacity to rFVIIa of the other platelets in the platelet population.

In another embodiment, the platelets in the subpopulation of platelets have about a 50%, 75%, 100%, 125%, 150%, 175%, 200%, 300%, 400%, or a 500% higher binding capacity to rFVIIa, as compared to the binding capacity to rFVIIa of the other platelets in the platelet population.

In one embodiment, the subpopulation of platelets with a higher binding capacity to rFVIIa, as compared to the binding capacity to rFVIIa of the other platelets in the platelet population, consists of at least 2% of the platelet population. In another embodiment, the subpopulation of platelets consists of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 40%, 50%, or higher, of the platelet population. In another embodiment, the subpopulation of platelets consists of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 40%, 50%, or higher, of the platelet population.

In one embodiment, the platelet population contains a subpopulation of platelets having about a 0.1-fold, 0.15-fold, 0.2-fold, 0.25-fold, 0.3-fold, 0.4-fold, 0.5 fold, 0.6-fold, 0.7-fold, 0.8-fold, 0.9-fold, 1-fold, 1.5-fold, 2 fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, or about a 9-fold higher binding capacity to rFVIIa, as compared to the binding capacity to rFVIIa of the other platelets in the platelet population.

In one embodiment, the platelet population contains a subpopulation of platelets having about a 10-fold, 11-fold, 12 fold, 13-fold, 14-fold, 15-fold, 16-fold, 17-fold, 18-fold, or a 19-fold higher binding capacity to rFVIIa, as compared to the binding capacity to rFVIIa of the other platelets in the platelet population.

In another embodiment, the platelet population contains a subpopulation of platelets having about a 20-fold, 21-fold, 22-fold, 23-fold, 24-fold, 25-fold, 26-fold, 27-fold, 28-fold, or a 29-fold higher binding capacity to rFVIIa, as compared to the binding capacity to rFVIIa of the other platelets in the platelet population.

In another embodiment, the platelet population contains a subpopulation of platelets having about a 30-fold, 31-fold, 32-fold, 33-fold, 34-fold, 35-fold, 36-fold, 37-fold, 38-fold, or a 39-fold higher binding capacity to rFVIIa, as compared to the binding capacity to rFVIIa of the other platelets in the platelet population.

In another embodiment, the platelet population contains a subpopulation of platelets having about a 40-fold, 41-fold, 42-fold, 43-fold, 44-fold, 45-fold, 46-fold, 47-fold, 48-fold, or a 49-fold higher binding capacity to rFVIIa, as compared to the binding capacity to rFVIIa of the other platelets in the platelet population.

In another embodiment, the platelet population contains a subpopulation of platelets having about a 50-fold, 51-fold, 52-fold, 53-fold, 54-fold, 55-fold, 56-fold, 57-fold, 58-fold, 59-fold, 60-fold, 70-fold, 80-fold, 90-fold, 100-fold, 150-fold, 200-fold, 250-fold, 300-fold, 350-fold, 400-fold, 450-fold, or about a 500-fold higher binding capacity to rFVIIa, as compared to the binding capacity to rFVIIa of the other platelets in the platelet population.

In another embodiment, the platelet population contains a subpopulation of platelets having about a 50%, 75%, 100%, 125%, 150%, 175%, 200%, 300%, 400%, or a 500% higher binding capacity to rFVIIa, as compared to the binding capacity to rFVIIa of the other platelets in the platelet population.

In one embodiment, the platelet subpopulation with a higher binding capacity to rFVIIa, as compared to the binding capacity to rFVIIa of the other platelets in the platelet population, consists of at least 2% of the platelet population. In another embodiment, the platelet subpopulation consists of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 40%, 50%, or higher, of the platelet population. In another embodiment, the platelet subpopulation consists of about 1%, 2%, 3%, 4%, 5%, 6%, 7%, 8%, 9%, 10%, 11%, 12%, 13%, 14%, 15%, 16%, 17%, 18%, 19%, 20%, 21% a, 22%, 23%, 24%, 25%, 26%, 27%, 28%, 29%, 30%, 40%, 50%, or higher, of the platelet population.

In one embodiment, the sample of platelets is obtained from a blood sample from the subject. In another embodiment, the sample of platelets is obtained from a serum sample from the subject. In one embodiment, the sample of platelets is a fresh sample. In another embodiment, the sample of platelets is a concentrate. In one embodiment, the sample of platelets is a preserved sample. In another embodiment, the sample of platelets is a rehydrated lyophilized sample. In one embodiment, the sample of platelets is a frozen sample.

In one embodiment, the subject has a bleeding disorder. In one embodiment, the bleeding disorder is hemophilia. In one embodiment, the hemophilia is hemophilia with inhibitors. In another embodiment, the hemophilia is hemophilia without inhibitors. In a further embodiment, the hemophilia is hemophilia A. In yet another embodiment the hemophilia is hemophilia B. In one embodiment, the hemophilia is hemophilia A with inhibitors. In another embodiment, the hemophilia is hemophilia B with inhibitors. In one embodiment, the inhibitors are to Factor VIII, In another embodiment the inhibitors are to Factor IX. In another embodiment, the hemophilia is acquired hemophilia. In one embodiment, the hemophilia is congenital hemophilia A with inhibitors. In another embodiment, the hemophilia is acquired hemophilia A with inhibitory auto antibodies to FVIII. In one embodiment, the hemophilia is congenital hemophilia B with inhibitors. In another embodiment, the hemophilia is acquired hemophilia B with inhibitory auto antibodies to FIX.

In one embodiment, the bleeding disorder is a non-hemophilia bleeding disorder. In one embodiment, the bleeding disorder is blood loss from trauma. In another embodiment, the bleeding disorder is FVII deficiency. In one embodiment, the bleeding disorder is FV deficiency. In another embodiment, the bleeding disorder is FX deficiency. In one embodiment, the bleeding disorder is FXI deficiency. In one embodiment, the bleeding disorder is FXIII deficiency. In one embodiment, the bleeding disorder is fibrinogen deficiency. In one embodiment, the bleeding disorder is prothrombin deficiency. In another embodiment, the bleeding disorder is dilutional coagulopathy. In a further embodiment, the bleeding disorder is thrombocytopenia. In yet another embodiment, the bleeding disorder is blood loss from high-risk surgeries. In another embodiment, the bleeding disorder is intracerebral hemorrhage. In one embodiment, the bleeding disorder is von Willebrand disease. In a further embodiment, the bleeding disorder is von Willebrand disease with inhibitors to von Willebrand factor.

In one embodiment, the bleeding disorder is a congenital platelet function defect; including, but not limited to, platelet storage pool disorder, Glanzmann's thrombasthenia, or Bernard-Soulier syndrome. In one embodiment, the bleeding disorder is an acquired platelet function defect. In one embodiment, the bleeding disorder is a congenital deficiency of Factor II, Factor V, Factor VII, Factor X, or Factor XI. In one embodiment, the bleeding disorder is neonatal and pediatric coagulopathies. In one embodiment, the bleeding disorder is a platelet function disorder. In another embodiment, the bleeding disorder is heparin-induced thrombocytopenia. In one embodiment, the bleeding disorder is disseminated intravascular coagulation. In other embodiments, the bleeding disorder is any disorder known to one of skill in the art (for additional information, see e.g., The Absite Review, by Steven M. Fiser, Lippincott Williams and Wilkins 2004).

In one embodiment, the subject is an animal. In another embodiment, the subject is an animal that has or is diagnosed with a bleeding disorder. In one embodiment, the subject is an animal that is predisposed to or is at risk of developing a bleeding disorder. In other embodiments, the subject is a human. In other embodiments, the subject is a mammal. In some embodiments, the subject is a rodent, such as a mouse or a rat. In some embodiments, the subject is a cow, pig, sheep, goat, cat, horse, dog, and/or any other species of animal used as livestock or kept as pets.

In some embodiments, the subject is already suspected to have a bleeding disorder. In other embodiments, the subject is being treated for a bleeding disorder, before being treated according to the methods of the invention. In other embodiments, the subject is not being treated for a bleeding disorder, before being treated according to the methods of the invention.

4. Formulations, Dosage and Methods of Administration

In certain embodiments, the subject is a human and a platelet population or a subpopulation of platelets according to the methods described herein are human cells.

In some embodiments, a platelet population or a subpopulation of platelets according to the methods described herein can be administered to any suitable location in the subject, for example in the blood vessel, or any suitable site where administered platelet population or a subpopulation of platelets according to the methods described herein, binds to rFVIIa. In some embodiments, a platelet population or a subpopulation of platelets according to the methods described herein can be introduced by injection, catheter, or the like.

In some embodiments, a platelet population or a subpopulation of platelets according to the methods described herein can be supplied in the form of a pharmaceutical composition, comprising an isotonic excipient prepared under sufficiently sterile conditions for human administration. For general principles in medicinal formulation of platelets, see Sweeney et al., 1995, Quality of Platelet Concentrates, *Immunological Investigations,* 24(1&2), 353-370; and Stroncek D. F. and Rebulla P., 2007, Platelet Transfusions, *The Lancet,* 370(9585), 427-438. Choice of the excipient and any accompanying elements of the composition comprising a platelet population or a subpopulation of platelets according to the methods described herein will be adapted in accordance with the route and device used for administration. In some embodiments, a composition comprising a platelet population or a subpopulation of platelets according to the methods described herein can also comprise, or be accompanied with, one or more other ingredients that facilitate the delivery or functional mobilization of the platelet population or a subpopulation of platelets according to the methods described herein. Suitable ingredients include, for example, citrate phosphate dextrose (CPD) solution, plasma solutes, glucose, phosphate based buffering systems, bicarbonate based buffering systems, fatty acids, amino acids, sodium acetate, or other ingredients that support the storage and delivery of a platelet population or a subpopulation of platelets according to the methods described herein. In another embodiment, the composition may comprise autologous blood plasma or blood plasma (for additional information, see Sweeney et al., 1995).

In certain aspects, a platelet population or a subpopulation of platelets according to the methods described herein can be administered systemically. A platelet population or a subpopulation of platelets according to the methods described herein can be administered systemically, such as, but not limited to, intra-arterial or intravenous administration. In alternative embodiments, a platelet population or a subpopulation of platelets according to the methods described herein can be administered to the vascular system in various ways as would be determined appropriate by one of skill in the art (for additional information, see Sweeney et al., 1995 and Stroncek et al., 2007).

Administration of a platelet population or a subpopulation of platelets is not restricted to a single route, but may encompass administration by multiple routes. Multiple administrations may be sequential or concurrent. Other modes of application by multiple routes will be apparent to one of skill in the art.

In certain embodiments, a platelet population or a subpopulation of platelets according to the methods described herein can be administered and dosed in accordance with good medical practice, taking into account the clinical condition of the individual patient, the site and method of administration, scheduling of administration, patient age, sex, body weight and other factors known to one of skill in the art; such as, but not limited to, a medical practitioner. A platelet population or a subpopulation of platelets according to the methods described herein may be administered to a subject in a therapeutically effective amount to treat a bleeding disorder. A "therapeutically effective amount", for purposes herein, is thus determined by such considerations as are known in the art. The amount can be effective to achieve improvement, including, but not limited to, improved bleeding time, improved clotting time, improved prothrombin time, improved partial thromboplastin time, improved activated clotting time, or improvement or elimination of symptoms and other indicators as are selected as appropriate measures by those skilled in the art. For additional information, see e.g., The Absite Review by Steven M. Fiser, Lippincott Williams and Wilkins 2004.

A therapeutically effective amount of a platelet population or a subpopulation of platelets according to the methods described herein, that treats a bleeding disorder, can depend upon a number of factors known to those of ordinary skill in the art. The dose(s) of a platelet population or a subpopulation of platelets according to the methods described herein can vary, for example, depending upon the identity, size, and condition of the subject or sample being treated, further depending upon the route by which a platelet population or a subpopulation of platelets according to the methods described herein, is to be administered, if applicable, and the effect which the practitioner desires the platelet population or a subpopulation of platelets according to the invention to have upon the target of interest. These amounts can be readily determined by one of skill in the art. These amounts include, for example, number of platelets per kilogram (kg) of subject weight, such as about $1\times10^9$ cells/10 kg, about $1\times10^{10}$ cells/10 kg, about $1\times10^{11}$ cells/10 kg, about $1\times10^{12}$ cells/10 kg, or between about $1\times10^9$ cells/10 kg to $1\times10^{10}$ cells/10 kg, $1\times10^{10}$ cells/10 kg to $1\times10^{11}$ cells/10 kg, or to $1\times10^{11}$ cells/10 kg to $1\times10^{12}$ cells/10 kg, or any range in between. These amounts also include a unit dose of platelets, for example, at least $1\times10^9$ cells, $1\times10^{10}$ cells, $1\times10^{11}$ cells, $1\times10^{12}$ cells, or $1\times10^{13}$ cells, or more. For additional information, see Stroncek et al., 2007. Any of the therapeutic applications described herein can be applied to any subject in need of such therapy, including, for example, a mammal such as a human.

Appropriate dosing regimens can also be determined by one of skill in the art without undue experimentation, in order to determine, for example, whether to administer the agent in one single dose or in multiple doses, and in the case of multiple doses, to determine an effective interval between doses.

In certain embodiments, a platelet population or a subpopulation of platelets according to the methods described herein can be administered alone, or in combination with other cells, tissue, tissue fragments, clotting factors, such as, but not limited to, recombinant Factor VIIa (rFVIIa), and other known clotting factors, small molecules, biologically active or inert compounds, or other additive intended to enhance the delivery, efficacy, tolerability, or function of the platelet population or a subpopulation of platelets.

In certain embodiments, a platelet population or a subpopulation of platelets according to the methods described herein is stored for later injection/infusion. In some embodiments, a platelet population or a subpopulation of platelets according to the methods described herein can be stored for up to 5 days, up to one week, or up to two weeks. For additional information, see Stroncek et al., 2007.

Therapy dose and duration will depend on a variety of factors, such as the disease type, patient age, therapeutic index of the drugs, patient weight, and tolerance of toxicity. Initial dose levels will be selected based on their ability to achieve ambient concentrations shown to be effective in in vivo models, and in clinical trials. The skilled clinician using standard pharmacological approaches can determine the dose of a particular therapeutic and duration of therapy for a particular patient in view of the above stated factors. The response to treatment can be monitored by analysis of coagulation measures, and one of skill in the art, such as a clinician, will adjust the dose and duration of therapy based on the response to treatment revealed by these measurements.

A platelet population or a subpopulation of platelets according to the invention described herein can be administered to the subject once (e.g., as a single injection or infusion). Alternatively, a platelet population or a subpopulation of platelets according to the methods described herein can be administered once or twice daily to a subject in need thereof for a period of from about two to about twenty-eight days, or from about seven to about ten days. A platelet population or a subpopulation of platelets according to the methods described herein can also be administered once or twice daily to a subject for a period of 1, 2, 3, 4, 5, 6, 7, 8, 9, 10, 11, 12 times per year, or a combination thereof. Furthermore, a platelet population or a subpopulation of platelets according to the methods described herein can be co-administrated with another therapeutic.

A platelet population or a subpopulation of platelets according to the methods described herein can be formulated and administered to reduce the symptoms associated with a bleeding disorder by any means that allow the platelets to exert their effect on the subject in vivo. For example, a platelet population or a subpopulation of platelets may be administered to the subject by known procedures including, but not limited to, intravascular or intravenous administration. A platelet population or a subpopulation of platelets of the invention may be administered parenterally, or by intravascular, intravenous, delivery. For example, delivery may be by injection, infusion, or catheter delivery. In one embodiment, a platelet population or a subpopulation of platelets of the invention may be administered to the subject by way of delivery directly to the vascular system, such as by way of a catheter inserted into, a vein of the subject.

A platelet population or a subpopulation of platelets according to the invention can be administered by any conventional means available for use in conjunction with pharmaceuticals, either as individual therapeutic active ingredients, or in a combination of therapeutic active ingredients. It can be administered alone, but are generally administered with a pharmaceutical carrier selected on the basis of the chosen route of administration and standard pharmaceutical practice.

Pharmaceutical compositions for use in accordance with the invention can be formulated in conventional manner using one or more physiologically acceptable carriers or excipients. The therapeutic compositions of the invention can be formulated for a variety of routes of administration, including systemic administration. Techniques and formulations generally can be found in *Remmington's Pharmaceutical Sciences*, Meade Publishing Co., Easton, Pa. (20$^{th}$ Ed., 2000), the entire disclosure of which is herein incorporated by reference. For systemic administration, an injection is useful, intravenous and intraarterial. For injection, the therapeutic compositions of the invention can be formulated in liquid solutions, for example in physiologically compatible buffers, such as citrate phosphate dextrose solution (see e.g., Sweeney et al., 1995). In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the platelet population or subpopulation of platelets according to the invention can be used. Supplementary active compounds can also be incorporated into the compositions.

A pharmaceutical composition of the invention is formulated to be compatible with its intended route of administration. Examples of routes of administration include parenteral, e.g., intravenous, and intraarterial administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, containers, or blood bags made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water; ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of injectable compositions can be brought about by incorporating an agent which delays absorption, for example, aluminum monostearate and gelatin.

Sterile injectable solutions can be prepared by incorporating the platelet population or a subpopulation of platelets in the required amount in an appropriate solvent with one or a combination of ingredients enumerated herein, as required, followed by filtered sterilization. Generally, dispersions are prepared by incorporating a platelet population or a subpopulation of platelets of the invention into a sterile vehicle which contains a basic dispersion medium and the required other ingredients from those enumerated herein.

Examples of diluents and/or carriers and/or other additives that may be used include, but are not limited to, water, glycols, oils, alcohols, aqueous solvents, organic solvents, DMSO, saline solutions, physiological buffer solutions, peptide carriers, starches, sugars, preservatives, antioxidants, coloring agents, pH buffering agents, granulating agents, lubricants, binders, disintegrating agents, emulsifiers, binders, excipients, extenders, glidants, solubilizers, stabilizers, surface active agents, suspending agents, tonicity agents, viscosity-altering agents, carboxymethyl cellulose, crystalline cellulose, glycerin, gum arabic, lactose, magnesium stearate, methyl cellulose, powders, saline, sodium alginate. The combination of diluents and/or carriers and/or other additives used can be varied taking into account the nature of the active agents used (for example the solubility and stability of the active agents), the route of delivery (e.g. oral, parenteral, etc.), whether the agents are to be delivered over an extended period (such as from a controlled-release capsule), whether the agents are to be co-administered with other agents, and various other factors. One of skill in the art will readily be able to formulate the composition for the desired use without undue experimentation.

For parenteral administration (i.e., administration by through a route other than the alimentary canal), a platelet population or subpopulation of platelets of the invention may be combined with a sterile aqueous solution that is isotonic with the blood of the subject. Such a formulation may be prepared by dissolving the active ingredient in water containing physiologically-compatible substances, such as sodium chloride, glycine and the like, and having a buffered pH compatible with physiological conditions, so as to produce an aqueous solution, then rendering the solution sterile. The formulation may be presented in unit or multi-dose containers, such as, but not limited to, containers or blood bags. The formulation may be delivered by injection, infusion, or other means known in the art.

In some embodiments, a platelet population or subpopulation of platelets of the invention is provided in unit dose form such as a single-dose injection or infusion vial.

According to the methods of the invention, a platelet population or subpopulation of platelets of the invention can be administered to a subject either as a single agent, or in combination with one or more other agents. In one embodiment, a platelet population or subpopulation of platelets of the invention is administered to a subject as a single agent. In one embodiment, a platelet population or subpopulation of platelets of the invention is administered to a subject alone. In one embodiment, a platelet population or subpopulation of platelets of the invention is administered to a subject in combination with one or more other agents.

In certain embodiments, a platelet population or subpopulation of platelets of the invention may be used in combination with other agents that are used for the treatment or prevention of a bleeding disorders. In certain embodiments, a platelet population or subpopulation of platelets of the invention may be used in combination with other agents that are not used for the treatment or prevention of bleeding disorders. In one embodiment, a platelet population or subpopulation of platelets of the invention may be delivered to a subject as part of the same pharmaceutical composition or formulation containing one or more additional active agents. In another embodiment, a platelet population or subpopulation of platelets of the invention may be delivered to a subject in a composition or formulation containing only that active agent, while one or more other agents are administered to the subject in one or more separate compositions or formulations. In one embodiment, the other agents are not used for the treatment or prevention of bleeding disorders. In another embodiment, the other agents are used for the treatment or prevention of bleeding disorders.

A platelet population or subpopulation of platelets of the invention, and the other agents that are used for the treatment or prevention of bleeding disorders may be administered to the subject at the same time, or at different times. A platelet population or subpopulation of platelets of the invention, and the other agents that are not used for the treatment or prevention of bleeding disorders may be administered to the subject at the same time, or at different times. For example, a platelet population or subpopulation of platelets of the invention and the other agents may be administered within minutes, hours, days, weeks, or months of each other, for example as part of the overall treatment regimen of a subject. In some embodiments, a platelet population or subpopulation of platelets of the invention may be administered prior to the administration of other agents. In other embodiments, a platelet population or subpopulation of platelets of the invention may be administered subsequent to the administration of other agents.

A platelet population or subpopulation of platelets of the invention may also be used in combination with known therapies for a bleeding disorder. Examples include, but are not limited to, recombinant Factor VIIa, such as Novoseven®, FEIBA, BeneFix® (recombinant Factor IX), Kogenate® FS (recombinant Factor VIII), Recombinate (recombinant Factor VIII), Advate® (recombinant Factor VIII), Helixate® FS (recombinant Factor VIII), Koāte®-DVI (recombinant Factor VIII), Stimate® (desmopressin acetate), DDAVP® (desmopressin acetate), Bebulin (Factor IX Complex), Hemofil M® (human factor VIII), cryoprecipitated antihaemophilic factor (AHF), fresh frozen plasma (FFP), recombinant porcine FVIII, recombinant FV variants, recombinant FVIIa variants, recombinant FXa variants, FXIII, prothrombin, a mix of coagulation factors, antibodies mimicking FVIII, peptides mimicking FVIII, compounds mimicking FVIII, peptide inhibitors of TFPI, antibody inhibitors of compounds inhibiting TFPI, compounds inhibiting anti-coagulant proteins, and any therapy for treating a bleeding disorder that does not comprise rFVIIa as a single agent, as determined by a person of skill in the art.

A platelet population or subpopulation of platelets of the invention may also be used in combination with surgical or other interventional treatment regimens used for the treatment of bleeding disorders. In some embodiments, a platelet population or subpopulation of platelets of the invention is used as an adjuvant therapy. In other embodiments, a platelet population or subpopulation of platelets of the invention is used in combination with an adjuvant therapy.

EXAMPLE

This example is provided below to facilitate a more complete understanding of the present invention. However, the scope of the invention is not limited to specific embodiments disclosed in this example, which are for purposes of illustration only.

Example 1

Detection of High Donor Variation in Binding of Recombinant Activated Factor VII (rFVIIa) to Human Platelets, and of a Subpopulation Binding High Amounts of rFVIIa The variation of the rFVIIa binding capacity of platelets in platelet concentrates from 21 healthy donors, and the occurrence and frequency of a platelet subpopulation capable of binding high amounts of rFVIIa, are described herein.

Methods

Platelets are identified by staining for CD61 and P-selectin (CD62P) and forward/side scatter gating to discriminate their activation status. rFVIIa bound to activated or non-activated platelets is quantified using a DyLight488-labeled anti human FVIIa antibody. Fresh platelet concentrates are adjusted to 40,000 platelets per ml in 20 mM HEPES and 150 mM NaCl containing buffer adjusted to pH7.35. Platelets were diluted with 10× buffer containing 0.1 μg/mL convulxin (a collagen receptor GPVI agonist) and 5 nM thrombin, if activation was required, and incubated with rFVIIa (BAX 817 or Novoseven) at concentrations from 50 to 2000 nM for 7-15 min at 37° C. and 300 rpm. Then, platelets were fixed with 3.8% final concentration of paraformaldehyde contained in the same buffer and 5 mM CaCl$_2$.

Platelets were filtered through a 50 μm mesh filter and blocked for 10 min at room temperature by adding 5% fetal bovine serum. Then, platelets are centrifuged for 10 mM at 4° C. and 700 g. For staining of rFVIIa bound to the platelet surface, a rabbit anti human FVIIa polyclonal Dylight 488 antibody conjugate (Affinity BioReagents order #PA1-100250) was used at a final concentration of 20 μg/mL. After 15 min incubation at room temperature in the dark, platelets are counterstained by adding mouse monoclonal antibodies against CD61 (BD order #22458; conjugated to PerCP, 1.2 μg/ml final concentration) and CD62P (BD order #01732; P-selectin, conjugated to PE, final dilution 1:5) and incubated for 15 min at room temperature in the dark. Fibrinogen can be co-stained using a Dylight633 conjugated sheep anti-human fibrinogen conjugate (Affinity Biologicals order #SAFG-AP; at 10 μg/mL). Then, wash buffer is added (same buffer w/o FBS), mixed and centrifuged for 10 min at 4° C. and 700 g. Samples are resuspended for FACS analysis. Controls include platelets without rFVIIa, and a mouse IgG1 isotype control conjugated to PerCP (BD order #) at 1.2 μg/mL final concentration. Median fluorescence intensities of rFVIIa bound to all platelets and to sub-populations varying in rFVIIa binding were determined by flow cytometry. $K_D$ values were calculated using SigmaPlot v12.0.

Results

Figure 2B:
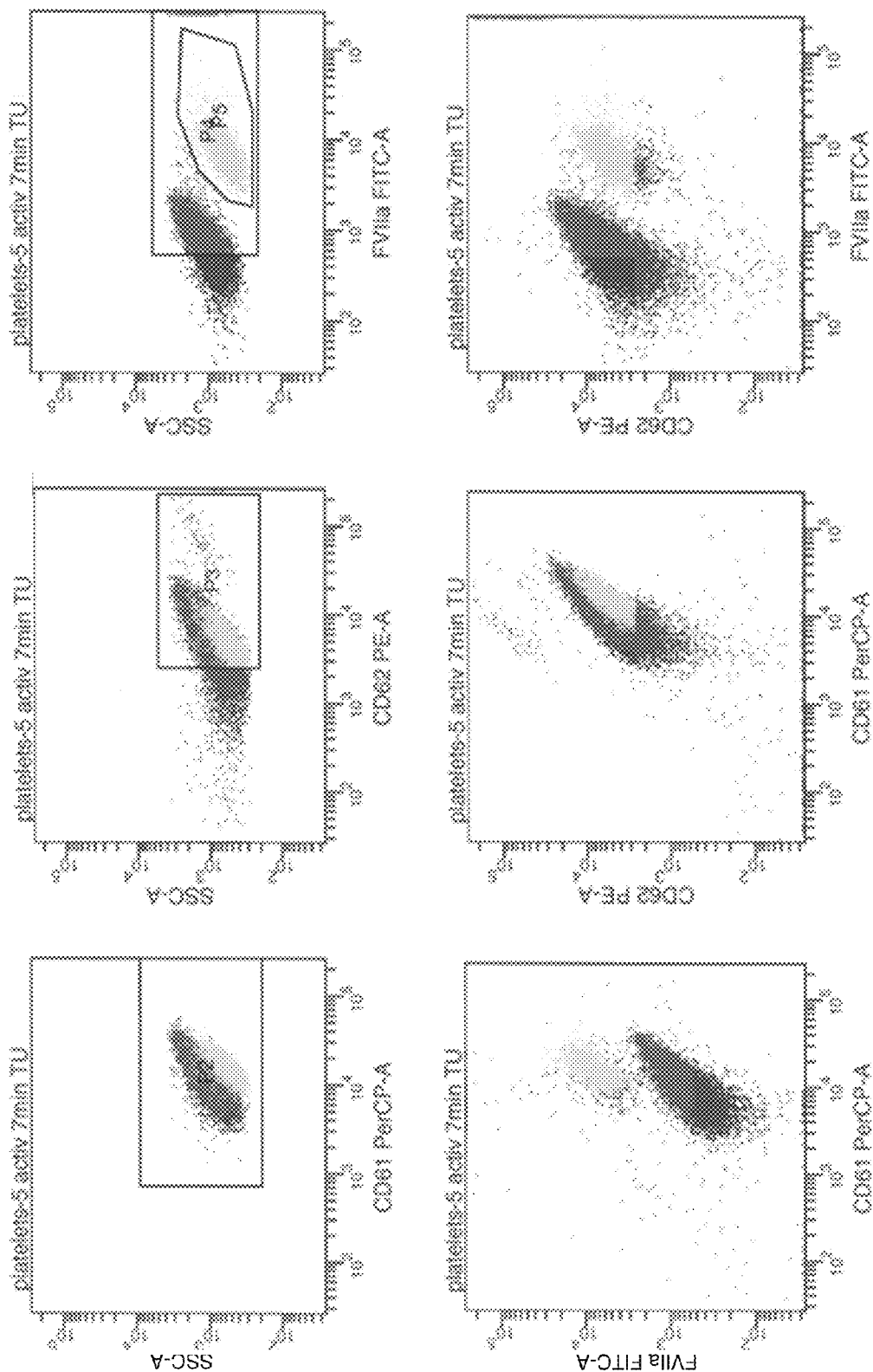

FACS raw data typical for one experiment are shown in FIG. 1, where 100 nM rFVIIa have been added without platelet activation and incubated for 7 min, and the same sample and handling steps with dual agonist activation in FIG. 2.

CD61 and CD62P Signals on Non-Activated and Activated Platelets

Figure 3:
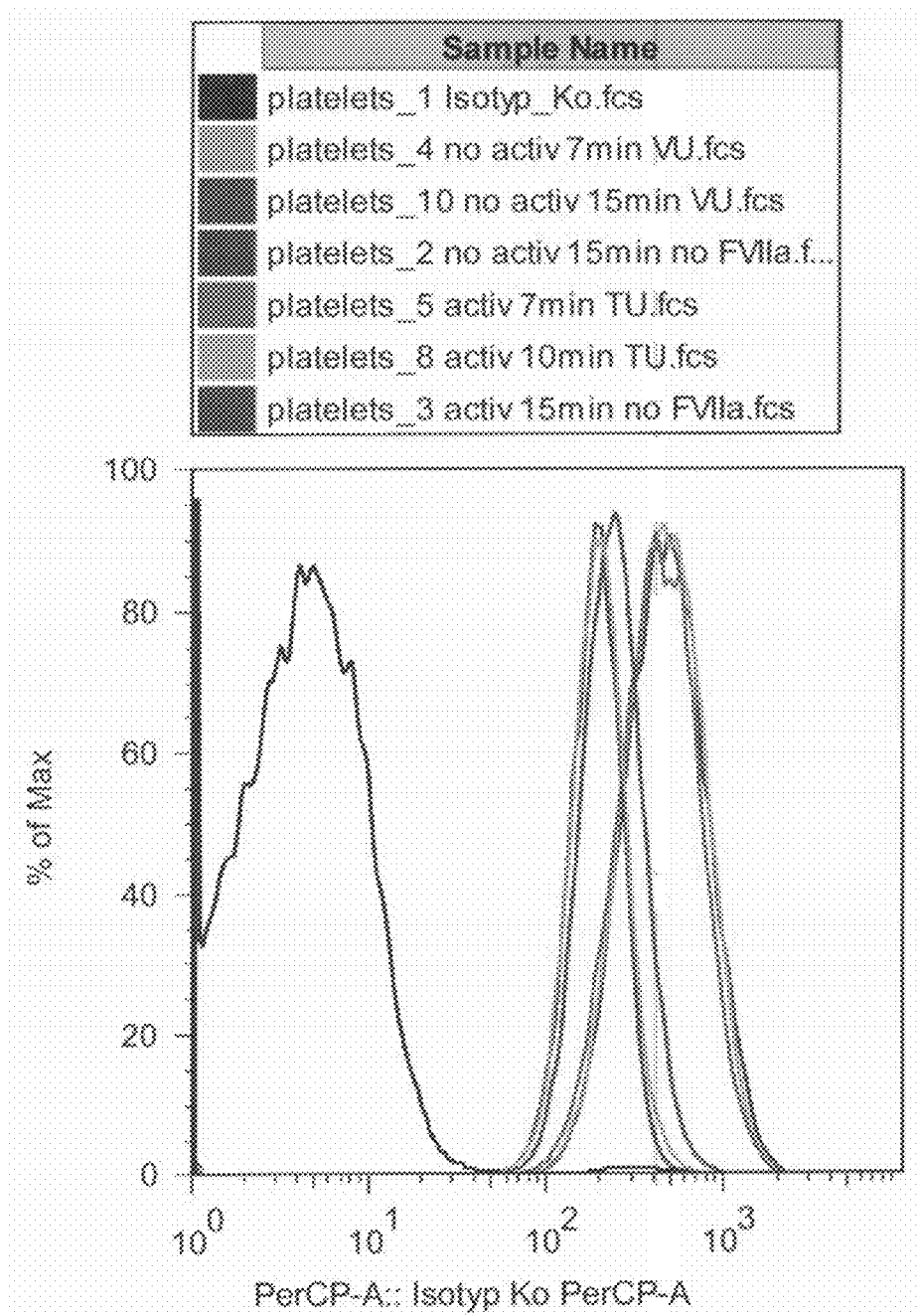
FIG. 3. Histogram overlay of the CD61PerCP staining for different samples as indicated. Population is gated by forward scatter versus side scatter. Graph showing detection of platelets using CD61 (GPIIIa, Integrin b3) as total platelet marker. Shown are three histograms each of dual-agonist activated and non activated platelet samples with rFVIIa added and stained with a mouse monoclonal antibody against human CD61 or with an IgG1 isotype control with the same fluorochrome label PerCP. The isotype control (black solid line) was also an activated sample. Activation led to a shift of peaks towards a higher signal.

The CD61 signal versus the isotype control for gating of platelets is shown in FIG. 3 for activated and non-activated platelets. Activation increases the CD61 signal approximately two-fold. Varying incubation times of 7, 10 and 15 min do not have an influence on the CD61 signal.

Figure 4:
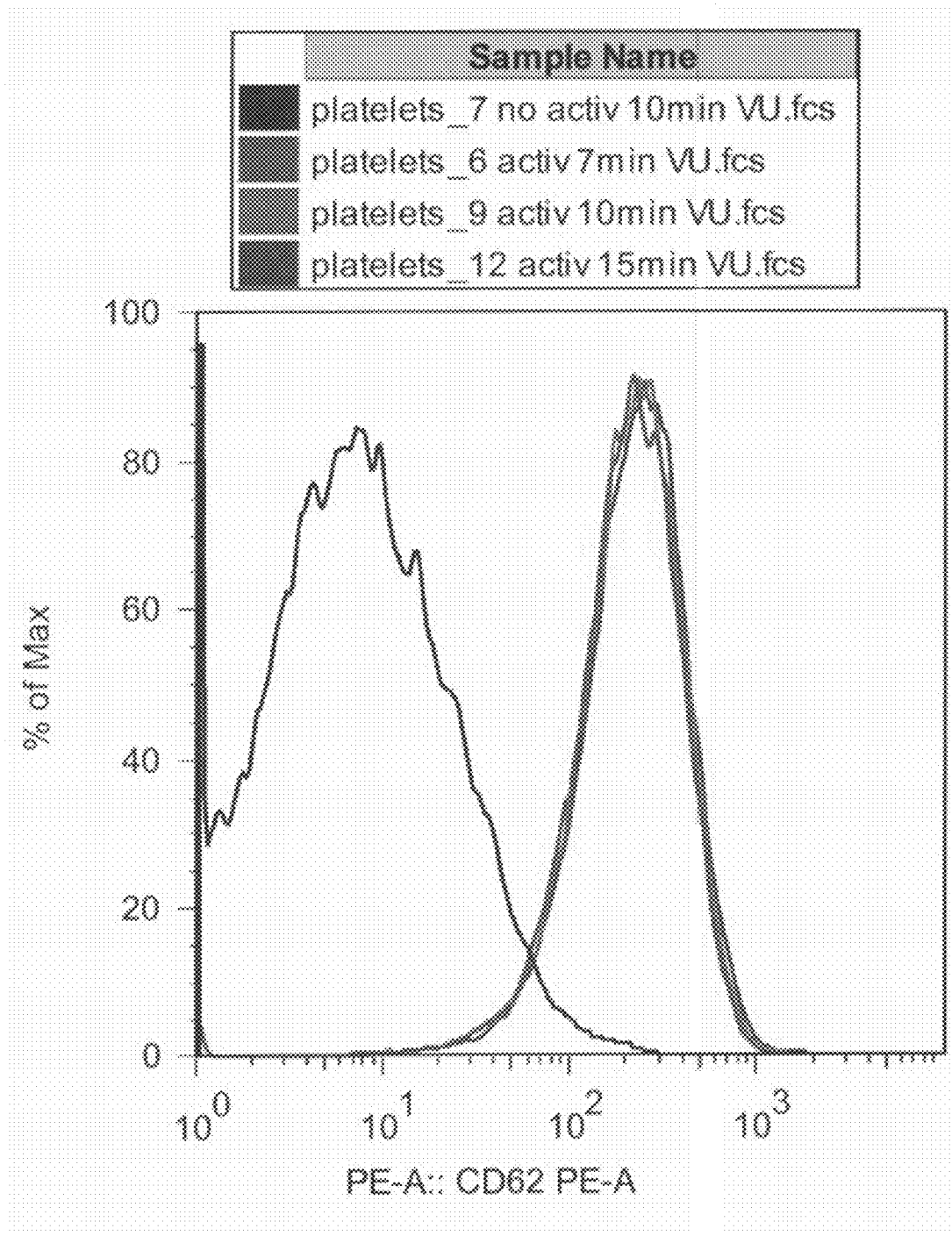
FIG. 4. Histogram overlay of the CD62PE staining for different samples as indicated. Population is gated by forward scatter versus side scatter and CD61. Graph showing measurement of platelet activation using CD62P (P-selectin) as marker for activated platelets. One histogram (black line) represents non-activated platelets with rFVIIa added and incubated for 10 min. Three histograms show platelets after dual-agonist activation with thrombin and convulxin in presence of 100 nM rFVIIa after 7 minutes (red line), 10 minutes (green line), and 15 min (blue line) incubation time.
Figure 5:
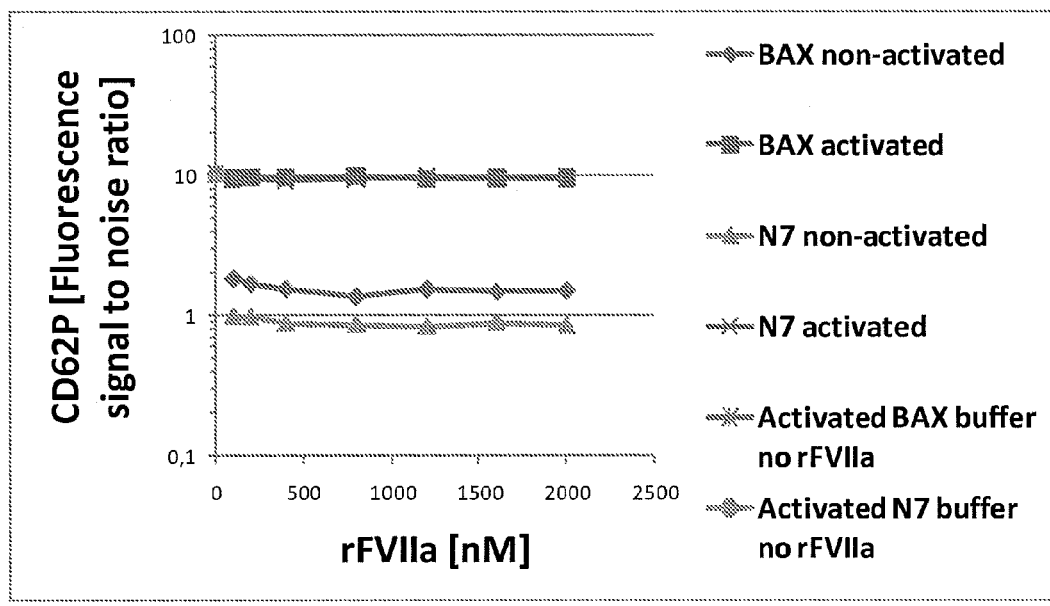
FIG. 5. CD62P signal as an indicator for platelet activation at a range of rFVIIa concentrations from 100 to 2000 nM. The CD62P signal was compared to non-activated platelet background in Novoseven N7 or Bax 817 formulation buffer. Shown are CD62P signal to noise ratios of non-activated or dual-agonist activated platelets with 100-2000 nM rFVIIa bound (Novoseven or BAX 817).

Activated and non activated platelets as depicted in FIG. 4 stained with an anti-CD62P antibody-fluorochrome conjugate show that there is no influence of the activation time of 7, 10 and 15 min on the CD62P quantity on activated platelets. In FIG. 5, the CD62P signal is shown as an indicator for platelet activation. The CD62P signal was compared to non-activated platelet background in N7 or BAX 817 formulation buffer. It was shown that the CD62P signal intensity does not depend on rFVIIa concentration. Without being bound by theory, a higher degree of activation can be caused by BAX 817 without activators. It is noted that N7 did not lead to higher activation.

Dose Dependent Binding of rFVIIa to Platelets

Figure 6:
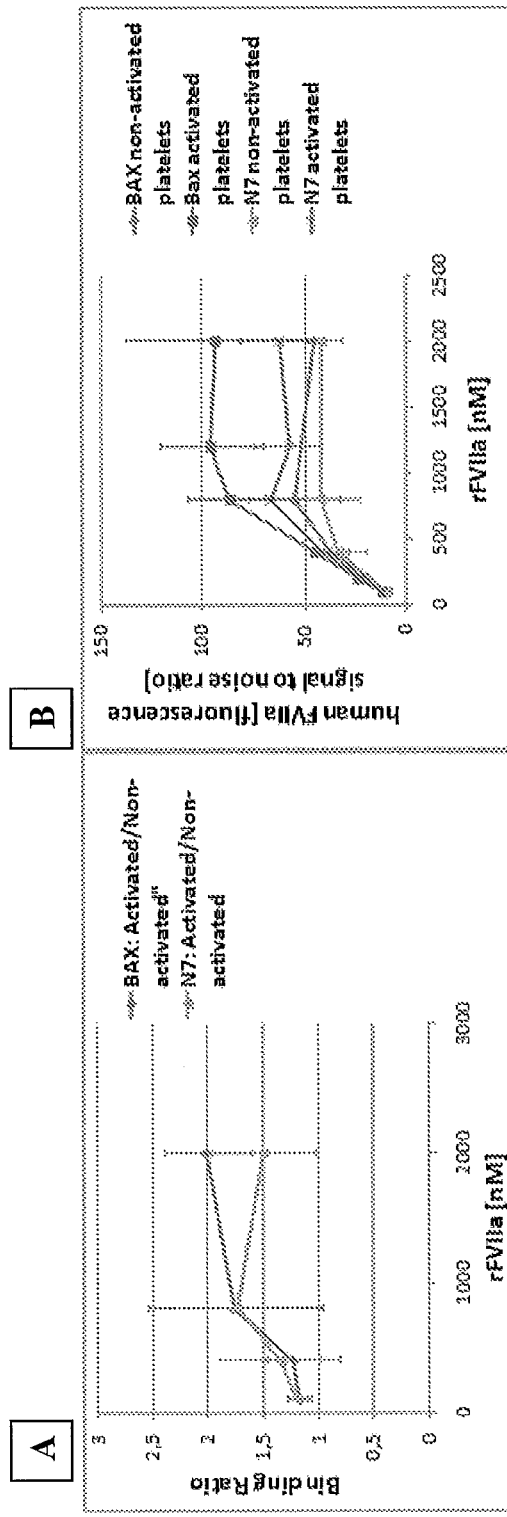
FIGS. 6A-B. Titration of rFVIIa (BAX=BAX 817, N7=Novoseven) on platelets. The median fluorescence values of rFVIIa bound to activated and non-activated platelets (CD61-positive population) are shown.

In FIG. 6, the titration of rFVIIa on platelets is shown. The median fluorescence values of rFVIIa bound to activated and non-activated platelets (CD61-positive population) are shown. Binding of BAX817 was somewhat higher than N7; ratios of binding to activated or non-activated platelets were similar. Binding of both rFVIIa preparations was shown dose dependent on activated or non activated platelets until saturation was reached. Without being bound by theory; a similar platelet interaction for BAX817 and Novoseven can be observed at rFVII a concentrations of 100 nM.

Detection of a rFVIIa High Binding Subpopulation

An additional, strongly positive FVII—fluorescein isothiocyanate (FITC) population was detected, which is shifting to the left closer to the major peak with longer incubation times (7, 10, 15 min) (mean and median fluorescence becomes lower over time). The percentage of the high FVIIa binding and the major platelet population stayed equal. Two NovoSeven lots were tested and show similar behavior.

Figure 7:
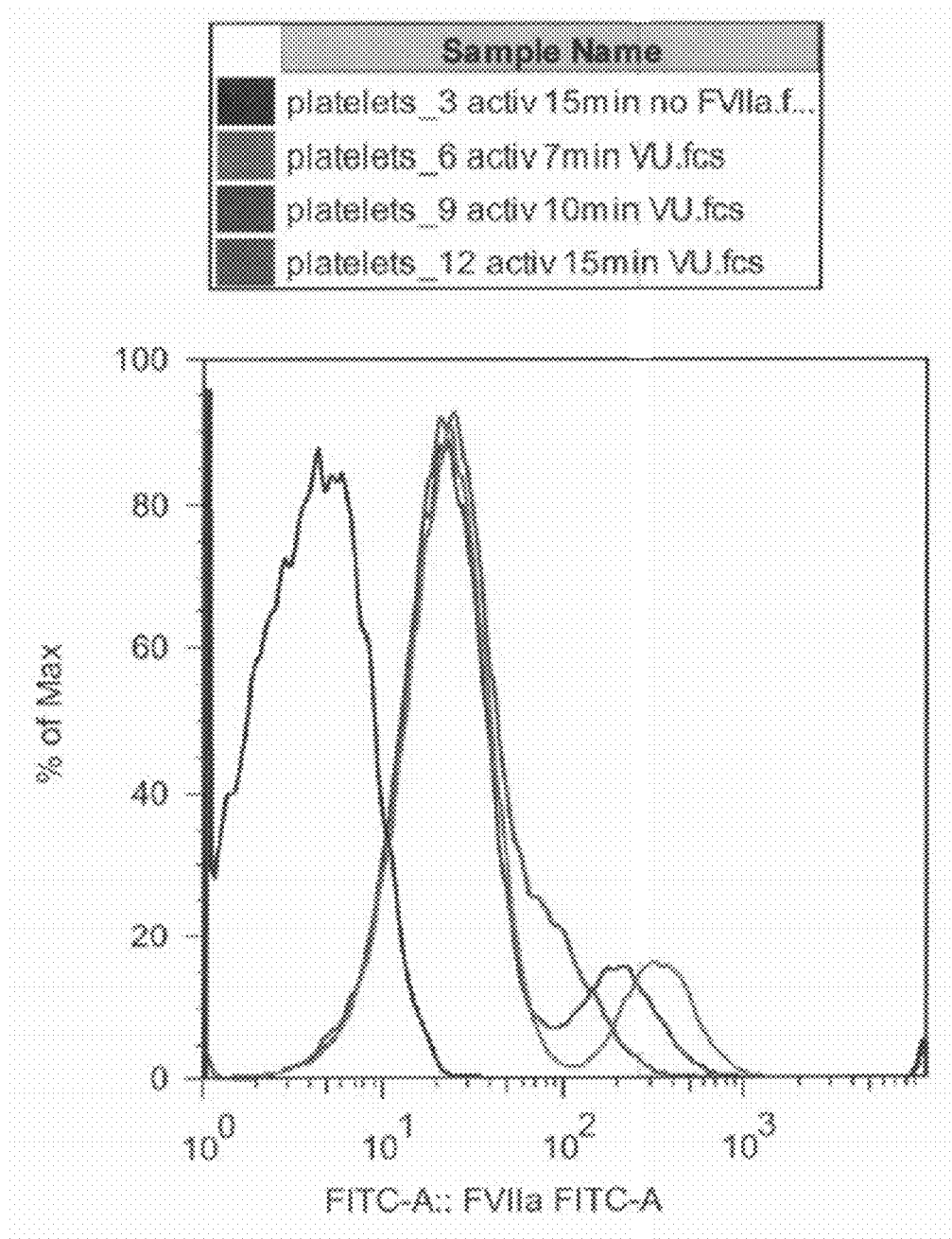
FIG. 7. Histogram overlay of the FVII DyLight488 staining for platelets after different activation times with thrombin/convulxin in presence or absence of 100 nM rFVIIa (Novoseven) as indicated. Populations are gated by forward scatter versus side scatter and CD61.

Histogram overlay of the FVII DyLight488 staining for different samples as indicated. Population is gated by forward scatter versus side scatter and CD61 (FIG. 7).

Figure 8:
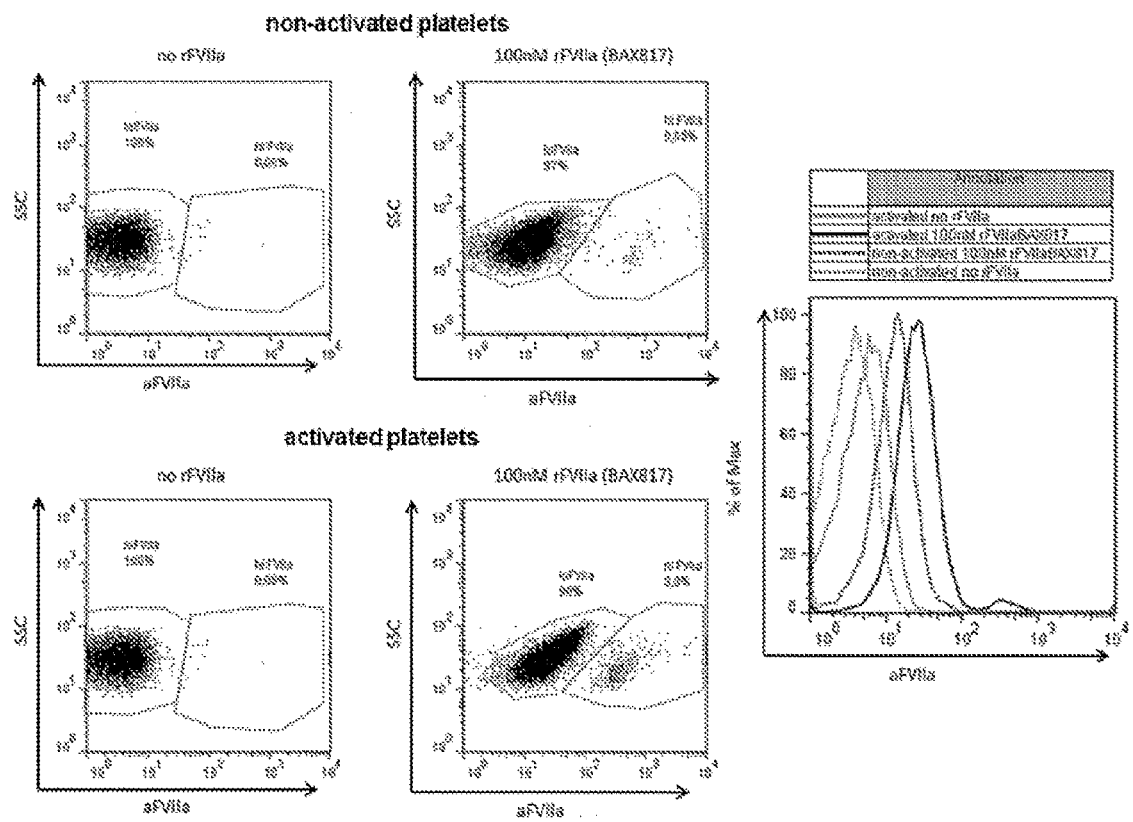
FIG. 8. FVIIa staining on non-activated (upper panel and dotted histogram lines) and thrombin and convulxin dual agonist activated (lower panel and solid histogram lines) platelets. Platelets were identified by forward- and side-scatter distribution and CD61 counterstaining. Stained platelets treated without rFVIIa are shown on the left side, platelets incubated with 100 nM rFVIIa on the right.
Figure 9:
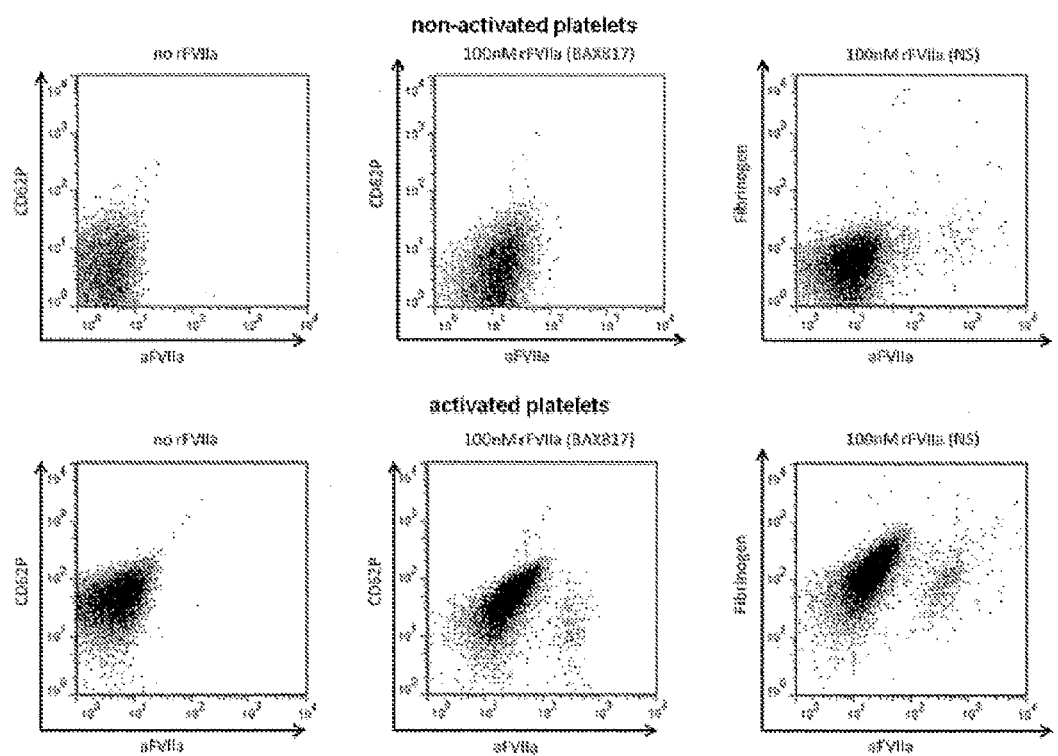
FIG. 9. FVIIa and CD62P or Fibrinogen counterstaining on non-activated (upper panel) and thrombin and convulxin dual agonist activated (lower panel) platelets. CD62P surface expression versus rFVIIa binding of platelets treated without rFVIIa is shown on the left side, CD62P surface expression versus FVIIa binding of platelets incubated with 100 nM rFVIIa BAX817 is shown in the middle. Fibrinogen surface expression versus FVIIa binding of platelets treated with 100 nM rFVIIa from NovoSeven (NS) is shown on the right. CD62P expression on resting or activated platelets treated with of 100 nM NovoSeven and 100 nM BAX817 was comparable.

In FIG. 8, platelet histograms and dotplots of non-activated and activated platelets from a typical donor are shown. Dotplots of the rFVIIa against the CD62P signal (FIG. 9) did not show a difference in the amounts of CD62P on the main and the rFVIIa high binding population. In FIG. 9 co-staining of rFVIIa and fibrinogen on platelets from one donor having the high-rFVIIa binding subpopulation is shown. The amount of fibrinogen exposed by the high rFVIIa binding platelets could not be distinguished from fibrinogen exposed by the major platelet population before and after activation. For resting platelets, a 2-fold increase in CD62P expression was observed for high binding platelet sub-populations, which was low compared to that in CD62P expression observed upon platelet activation (~40-fold).

Figure 10:
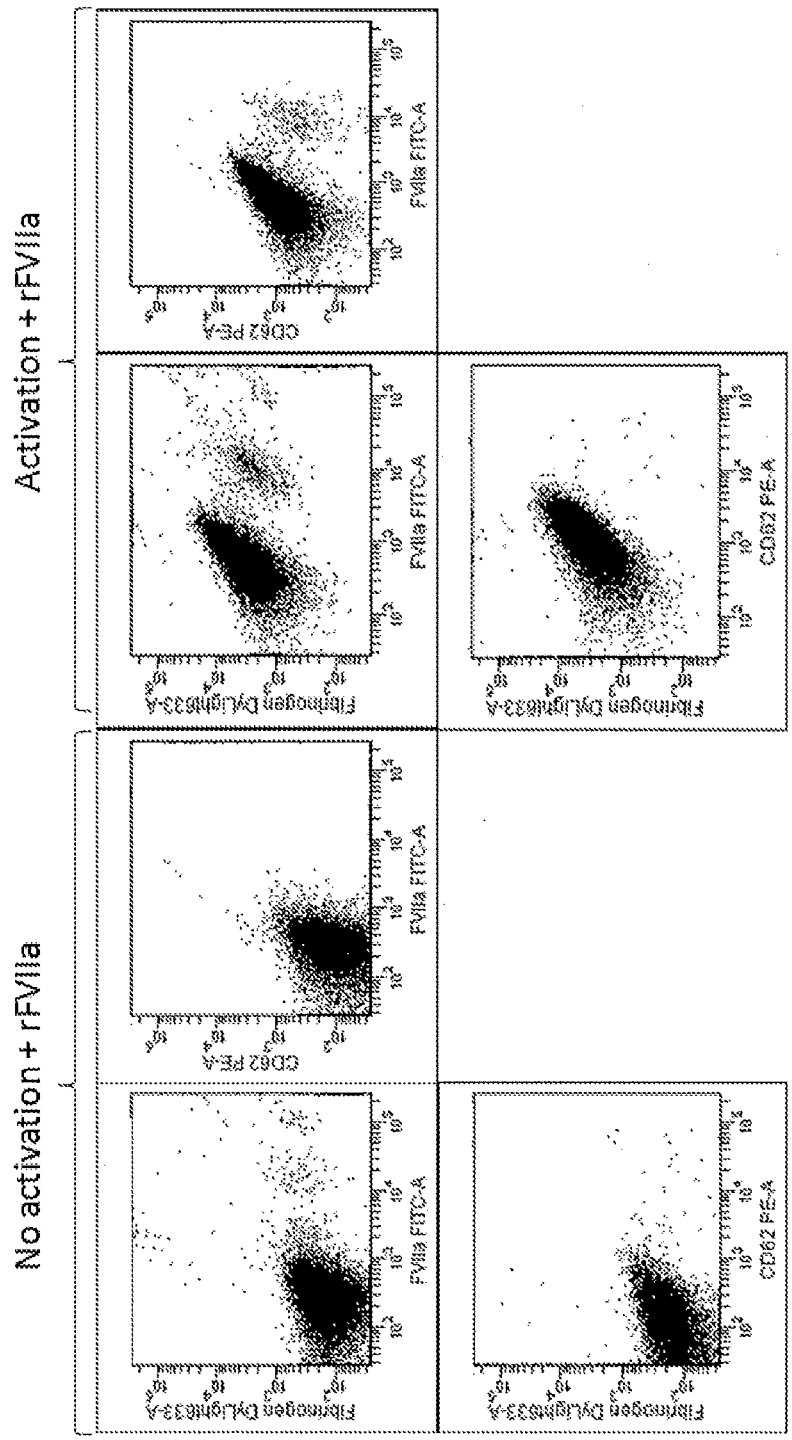
FIG. 10. FACS analysis showing platelet characteristics. The left-hand panel shows a non-activated platelet population and rFVIIa. The right-hand panel shows an activated platelet population and rFVIIa.

In FIG. 10, the platelet population is homogenous in terms of fibrinogen and CD62P exposure, but not rFVIIa binding (100 nM rFVIIa added). The high level of fibrinogen indicates that all platelets are "coated". Without being bound by theory, the subpopulation of platelets can be considered small.

Figure 11:
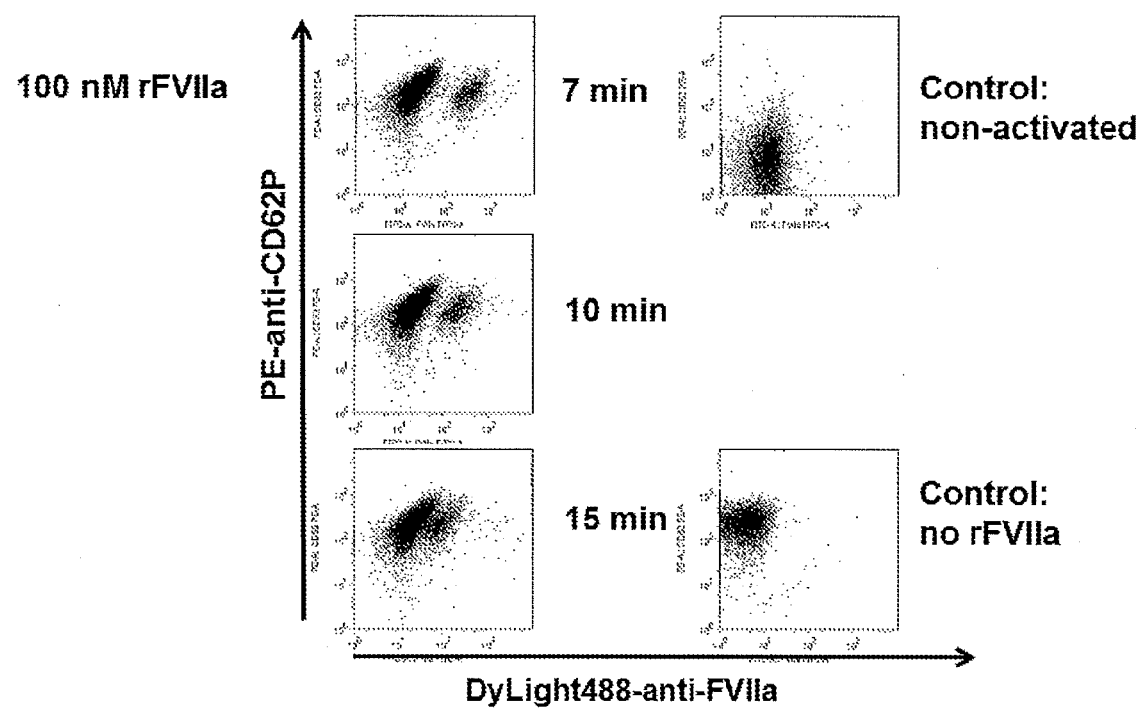
FIG. 11. FACS analysis showing a time course of the rFVIIa signal on activated platelets.
Figure 14:
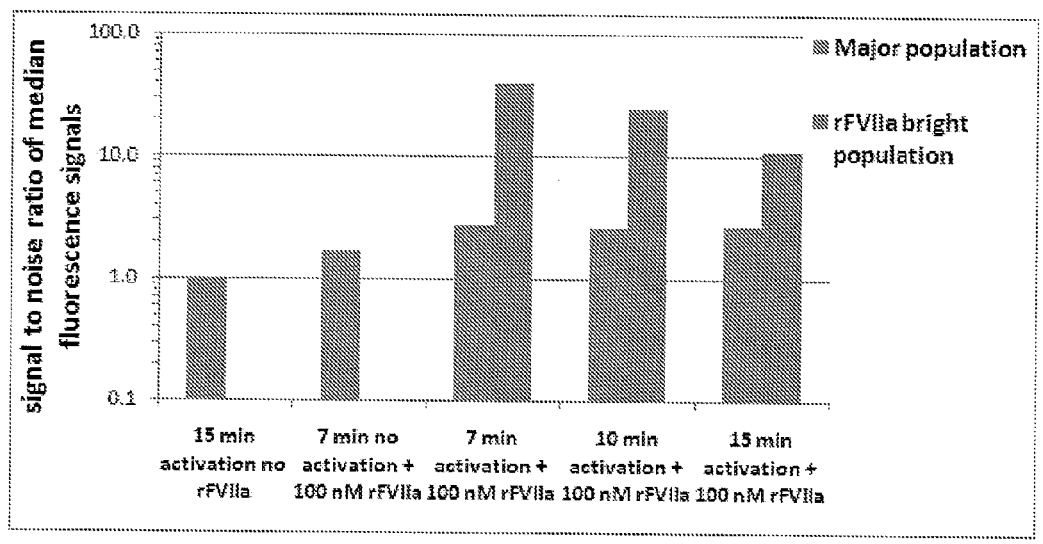
FIG. 14. Histogram showing the statistics of the time course of the rFVIIa signal on activated platelets.
Figure 15:
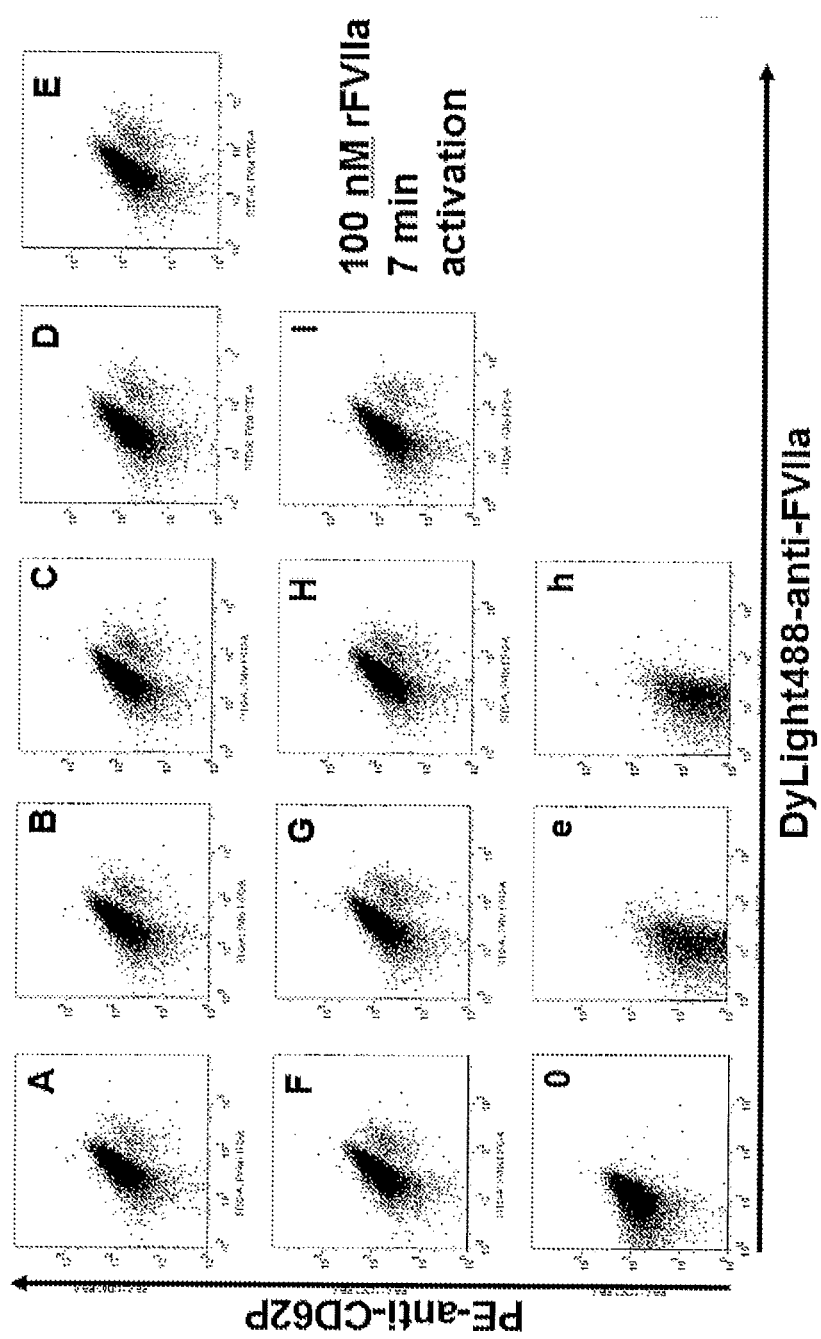
FIG. 15. Dotplots of BAX 817 lots and N7 gated on CD61. 100 nM rFVIIa and a 7 min dual agonist activation were used. Panels A-E use the BAX 817 lots; panels F-I use N7; panel 0) uses Des-GlaFVIIa; panel e) uses the BAX 817 lots and panel h) uses N7 lot on non-activated platelets.

In FIG. 11, the bright side-population that was detected was shown to be losing signal with time. This is shown also in FIG. 14.

Detection of High Donor Variation in rFVIIa Platelet Binding, and Characterization of Donors Regarding the High Binding Subpopulation Using FACS technology, binding of rFVIIa to platelet concentrates of 21 healthy donors was quantified, based on the assumption that the amount of rFVIIa bound to per cell correlates with the measured fluorescence intensity. In Tables 2 (non-activated) and 3 (double-activated platelets), all donors are listed with protocol addresses, $K_D$ values if calculable, relative median fluorescence intensities of the rFVIIa signals of all platelets compared to the controls without rFVIIa, and of frequencies and relative median fluorescence intensities of high binding populations compared to the major rFVIIa binding population. rFVIIa bound concentration dependently to non-activated and dual agonist activated platelets. On activated and non-activated platelets, binding was saturated at rFVIIa concentrations between 200 and 1200 nM. Median fluorescence intensity increase at 100 nM rFVIIa ranged from 4- to 33-fold for non-activated (mean±standard deviation: 14±8-fold) and from 5- to 37-fold for activated platelets (mean±standard deviation: 15±9-fold) compared with controls without rFVIIa. When assessing the total platelet population, binding constants for activated platelets ranged from 29 to 1025 nM (mean±standard deviation 392±355 nM; n=6), and from 56 to 357 nM (mean±standard deviation 184±88; n=10) for non-activated platelets.

TABLE 1

Mean and median fluorescence of FITC pos 1 (=major) population and the FITC pos 2 (=high rFVIIa binding) population after 7, 10 and 15 min incubation times

| Samples | FITC pos 1 | | | | FITC pos 2 | | | |
|---|---|---|---|---|---|---|---|---|
| | Median FITC | Mean FITC | CV FITC | % of parent | Median FITC | Mean FITC | CV FITC | % of parent |
| platelets_5 activ 7 min Novoseyen #1 | 25.41 | 28.13 | 52.17 | 81.05% | 271.45 | 302.17 | 52.65 | 14.97% |
| platelets_8 activ 10 min Novoseven #1 | 24.87 | 27.50 | 51.22 | 81.49% | 173.83 | 196.88 | 56.24 | 15.41% |
| platelets_11 activ 15 min Novoseven #1 | 24.91 | 27.46 | 50.40 | 80.96% | 93.77 | 107.98 | 57.62 | 15.39% |
| platelets 6 activ 7 min Novoseven #2 | 22.36 | 24.97 | 52.65 | 81.55% | 328.93 | 363.61 | 48.93 | 13.72% |
| platelets_9 activ 10 min Novoseven #2 | 21.45 | 24.20 | 54.40 | 80.87% | 199.54 | 229.02 | 60.42 | 14.05% |
| platelets_12 activ 15 min Novoseven #2 | 21.96 | 24.47 | 52.33 | 77.55% | 89.98 | 108.76 | 70.21 | 16.47% |

Figure 12:
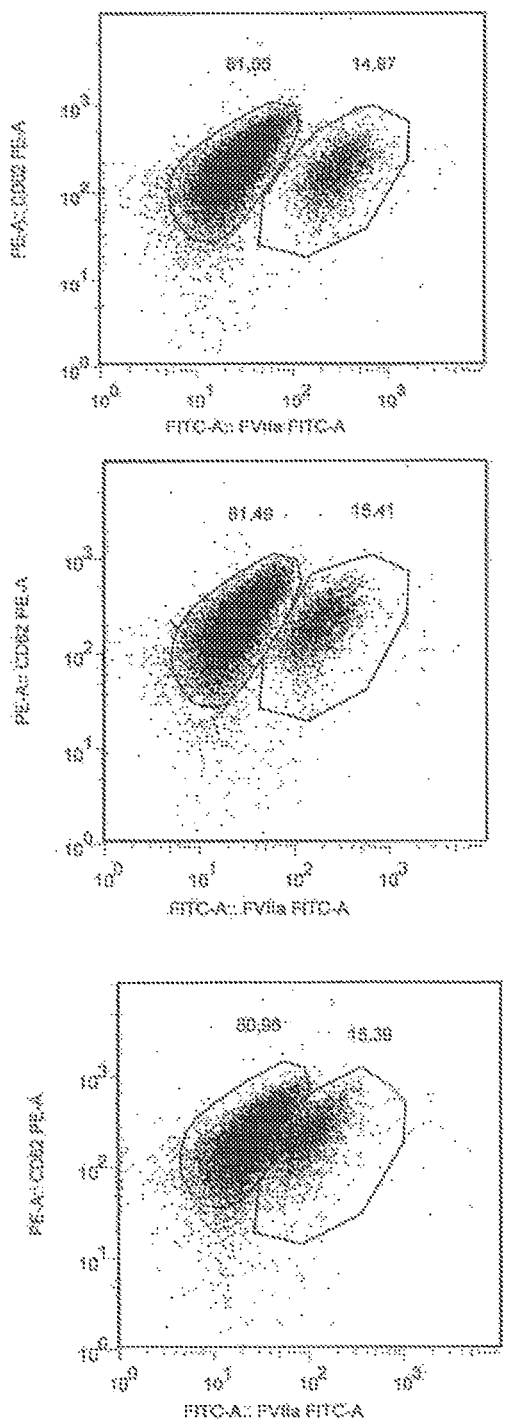
FIG. 12. Dot plot of FVII versus CD62P of Novoseven lot#1 bound to different platelet samples as indicated. Platelets with 100 nM Novoseven were thrombin/convulxin activated for 7 minutes (top), 10 minutes (middle), or 15 minutes (bottom). Platelets were identified via forward/side scatter properties and CD61 staining. Percentages of the CD61-population falling into the two regions defining the major and high-rFVIIa binding populations are shown just above each region.

Dot plot of FVII versus CD62 of Novoseven lot#1 for different platelet samples as indicated. Platelets were activated and incubated with Novoseven for 7 minutes (top), 10 minutes (middle), or 15 minutes (bottom) (FIG. 12).

Figure 13:
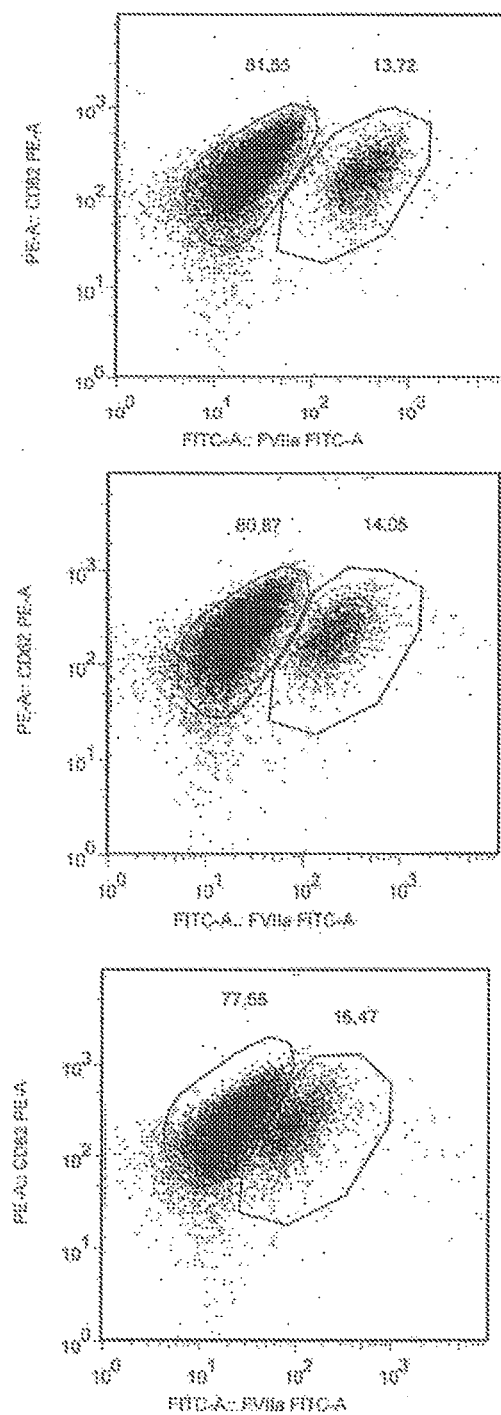
FIG. 13. Dot plot of FVII versus CD62P of Novoseven lot#2 bound to different platelet samples as indicated. Platelets with 100 nM Novoseven were thrombin/convulxin activated for 7 minutes (top), 10 minutes (middle), or 15 minutes (bottom). Platelets were identified via forward/side scatter properties and CD61 staining. Percentages of the CD61-population falling into the two regions defining the major and high-rFVIIa binding populations are given.

Dot plot of FVII versus CD62 of Novoseven lot#2 for different platelet samples as indicated. Platelets were activated and incubated with Novoseven for 7 minutes (top), 10 minutes (middle), or 15 minutes (bottom) (FIG. 13).

A platelet sub-population consisting of more than 2% was detected in 7 of 21 non-activated platelet donor concentrates, and in 16 of 21 after dual activation. In one donor, this population was visible only within resting platelets, in 9 donors only within activated platelets, and in 6 donors within resting and activated platelets. Up to 24% of total platelets were characterized by high capacity of rFVIIa binding in platelet concentrates from donors positive for this sub-population.

Regarding all donors described, this subpopulation bound on average 32-fold more rFVIIa than the main platelet population when non-activated, and on average 6-fold more within activated platelets. The rFVIIa high binding capacity subpopulation formation did not correlate with platelet activation or "coated" platelet formation, since all dual agonist activated platelets had similar distribution of CD62P and fibrinogen expression following activation.

A substantial inter-individual variation in binding of rFVIIa to resting and activated platelets was observed among a group of 21 donors. In some donor platelet concentrates, sub-populations of platelets with a ≥10-fold increase in rFVIIa binding, consisting of up to >20% of total platelets after activation, were identified.

This finding supports prediction of therapy outcomes or thrombogenic risks with rFVIIa or other bypassing therapies when studying a patient's platelet population, but also serves as means to improve hemophilia inhibitor bypassing therapy e.g. by recruiting platelet donors possessing the ability to bind high amounts of rFVIIa and isolating their platelets for transfusion. The invention solves the problem of a lack of understanding about this platelet population which is needed to carry out successful hemophilia therapy, off-label use of rFVIIa, or gene therapy when targeting platelets in an effort to treat bleeding disorders. Prior to this invention, there was no explanation why platelets bind more or less rFVIIa, but with this invention including functional and phenotypic characterization and identification of correlating factors, one induce/suppress high binding of rFVIIa to platelets in a patient.

TABLE 2

Percentages of the high rFVIIa binding sub-population, and ratios of fluorescence of the high binding versus the main platelet population for all rFVIIa concentrations measured from all donors; non-activated platelets. Values for populations <2% are in italic with grey fillings.

| Sample number | rFVIIa conc [nM] | % high rFVIIa binding subpopulation of all platelets | X-fold median fluorescence intensity of high rFVIIa binding population compared to the major population | KD [nM] | Saturation reached at rFVIIa concentration [nM] | X-fold median fluorescence intensity of all platelets compared to the control w/o rFVIIa at 100 nM |
|---|---|---|---|---|---|---|
| AH163 | 0 | *0.1* | *89* | 357 | 1200 | 8 |
|  | 100 | *0.6* | *29* |  |  |  |
|  | 200 | *0.9* | *17* |  |  |  |
|  | 400 | *1.1* | *25* |  |  |  |
|  | 800 | *1.2* | *20* |  |  |  |
|  | 1200 | *1.9* | *18* |  |  |  |
|  | 1600 | 2.1 | 17 |  |  |  |
|  | 2000 | 2.1 | 14 |  |  |  |
| AH162 | 0 | *0.1* | *108* | 219 | 800 | 9 |
|  | 100 | *1.2* | *56* |  |  |  |
|  | 200 | *1.3* | *57* |  |  |  |
|  | 400 | *1.6* | *39* |  |  |  |
|  | 800 | 2.2 | 25 |  |  |  |
|  | 1200 | 3.6 | 17 |  |  |  |
|  | 1600 | 3.8 | 19 |  |  |  |
|  | 2000 | 4.7 | 21 |  |  |  |
| AH155 | 0 | *0.2* | *77* | 242 | 800 | 9 |
|  | 100 | 2.0 | 36 |  |  |  |
|  | 200 | *1.6* | *36* |  |  |  |
|  | 400 | 2.1 | 24 |  |  |  |
|  | 800 | 2.6 | 17 |  |  |  |
|  | 1200 | 3.5 | 9 |  |  |  |

TABLE 2-continued

Percentages of the high rFVIIa binding sub-population, and ratios of fluorescence of the high binding versus the main platelet population for all rFVIIa concentrations measured from all donors; non-activated platelets. Values for populations <2% are in italic with grey fillings.

|       |      |     |    |     |                  |    |
|-------|------|-----|----|-----|------------------|----|
|       | 1600 | 3.7 | 9  |     |                  |    |
|       | 2000 | 3.5 | 9  |     |                  |    |
| AH153 | 0    | *0.4* | *45* |   | No saturation    | 12 |
|       | 100  | *1.3* | *55* |   |                  |    |
|       | 300  | *1.4* | *38* |   |                  |    |
|       | 900  | 2.2 | 18 |     |                  |    |
|       | 1800 | 3.7 | 10 |     |                  |    |
| AH148 | 0    | *0.0* | *22* |   | (800)            |    |
|       | 800  | *0.9* | *20* |   |                  |    |
|       | 2000 | *1.1* | *12* |   |                  |    |
|       | 4000 | *0.6* | *8*  |   |                  |    |
| AH146 | 0    | *0.0* | *47* |   | No saturation    | 9  |
|       | 100  | 2.1 | 52 |     |                  |    |
|       | 400  | 2.2 | 31 |     |                  |    |
|       | 800  | 2.7 | 19 |     |                  |    |
| AH141 | 0    | *0.2* | *33* |   | Not applicable   | 6  |
|       | 100  | *0.9* | *31* |   |                  |    |
|       | 500  | 3.1 | 46 |     |                  |    |
| AH139 | 0    | *0.6* | *48* |   | Not applicable   | 12 |
|       | 100  | *1.6* | *54* |   |                  |    |
| AH138 | 0    | *0.1* | *49* |   | Not applicable   | 11 |
|       | 100  | *0.7* | *42* |   |                  |    |
| AH135 | 0    | *0.2* | *22* |   | Not applicable   | 6  |
|       | 100  | *0.8* | *22* |   |                  |    |
| AH134 | 0    | *0.5* | *29* |   | Not applicable   | 5  |
|       | 100  | *0.9* | *14* |   |                  |    |
|       | 100  | *0.7* | *44* |   |                  | 4  |
| AH132 | 0    | *0.2* | *35* |   | Not applicable   | 5  |
|       | 100  | *0.7* | *22* |   |                  |    |
| JK070 | 0    | *0.1* | *11* |   | 200              | 20 |
|       | 50   | *0.9* | *45* |   |                  |    |
|       | 100  | *0.8* | *48* |   |                  |    |
|       | 200  | *0.9* | *43* |   |                  |    |
|       | 400  | *1.0* | *41* |   |                  |    |
|       | 800  | *1.3* | *25* |   |                  |    |
|       | 0    | *0.2* | *55* |   | 200              | 19 |
|       | 50   | *0.8* | *37* |   |                  |    |
|       | 100  | *0.8* | *36* |   |                  |    |
|       | 200  | *1.0* | *34* |   |                  |    |
|       | 400  | *0.9* | *30* |   |                  |    |
|       | 800  | *0.9* | *25* |   |                  |    |
| JK069 | 0    | *0.0* | *71* | 177 | 400            | 14 |
|       | 50   | *0.3* | *49* |   |                  |    |
|       | 100  | *0.3* | *38* |   |                  |    |

TABLE 2-continued

Percentages of the high rFVIIa binding sub-population, and ratios of fluorescence of the high binding versus the main platelet population for all rFVIIa concentrations measured from all donors; non-activated platelets. Values for populations <2% are in italic with grey fillings.

| | | | | | | |
|---|---|---|---|---|---|---|
| | 200 | *0.3* | *32* | | | |
| | 400 | *0.3* | *18* | | | |
| | 800 | *0.5* | *18* | | | |
| | 0 | *0.0* | *49* | | 400 | 15 |
| | 50 | *0.2* | *38* | | | |
| | 100 | *0.2* | *32* | | | |
| | 200 | *0.3* | *36* | | | |
| | 400 | *0.4* | *18* | | | |
| | 800 | *0.4* | *19* | | | |
| JK067 | 0 | *0.1* | *10* | 100 | 400 | 15 |
| | 50 | *1.0* | *26* | | | |
| | 100 | *1.1* | *29* | | | |
| | 200 | *1.1* | *35* | | | |
| | 400 | *1.2* | *28* | | | |
| | 800 | *1.1* | *20* | | | |
| | 0 | *0.3* | *9* | | 400 | 17 |
| | 50 | *1.0* | *27* | | | |
| | 100 | *0.8* | *32* | | | |
| | 200 | *1.0* | *32* | | | |
| | 400 | *1.1* | *24* | | | |
| | 800 | *1.1* | *19* | | | |
| JK066 | 0 | *0.1* | *14* | 158 | 400 | 23 |
| | 50 | *1.9* | *34* | | | |
| | 100 | 2.3 | 34 | | | |
| | 200 | 2.4 | 32 | | | |
| | 400 | 2.8 | 27 | | | |
| | 800 | 2.5 | 19 | | | |
| | 0 | *0.2* | *10* | | 400 | 20 |
| | 50 | 2.0 | 31 | | | |
| | 100 | 2.1 | 33 | | | |
| | 200 | 2.3 | 30 | | | |
| | 400 | 2.5 | 24 | | | |
| | 800 | 2.5 | 19 | | | |
| JK065 | 0 | *0.0* | *87* | | 200 | 22 |
| | 50 | 4.3 | 21 | | | |
| | 100 | 4.3 | 24 | | | |
| | 200 | 4.8 | 23 | | | |
| | 400 | 5.0 | 21 | | | |
| | 800 | 5.3 | 15 | | | |
| | 0 | *0.2* | *9* | | 300 | 26 |
| | 50 | 3.9 | 17 | | | |
| | 100 | 4.4 | 19 | | | |
| | 200 | 4.4 | 19 | | | |
| | 400 | 4.3 | 17 | | | |

TABLE 2-continued

Percentages of the high rFVIIa binding sub-population, and ratios of fluorescence of the high binding versus the main platelet population for all rFVIIa concentrations measured from all donors; non-activated platelets. Values for populations <2% are in italic with grey fillings.

| Donor | Conc | % | Ratio | | | |
|---|---|---|---|---|---|---|
| | 800 | 5.0 | 13 | | | |
| JK063 | 0 | *0.8* | *13* | 258 | No saturation | 33 |
| | 50 | *0.3* | *20* | | | |
| | 100 | *0.4* | *22* | | | |
| | 200 | *0.6* | *24* | | | |
| | 400 | *0.6* | *22* | | | |
| | 800 | *0.7* | *19* | | | |
| | 0 | *1.2* | *13* | | No saturation | 31 |
| | 50 | *0.2* | *28* | | | |
| | 100 | *0.3* | *24* | | | |
| | 200 | *0.6* | *23* | | | |
| | 400 | *0.6* | *22* | | | |
| | 800 | *0.7* | *19* | | | |
| JK062 | 0 | *0.3* | *22* | | 800 | 14 |
| | 50 | *0.6* | *44* | | | |
| | 100 | *0.5* | *51* | | | |
| | 200 | *0.6* | *41* | | | |
| | 400 | *0.7* | *33* | | | |
| | 800 | *0.8* | *21* | | | |
| | 0 | *0.3* | *16* | | 400 | 17 |
| | 50 | *0.5* | *33* | | | |
| | 100 | *0.5* | *38* | | | |
| | 200 | *1.1* | *8* | | | |
| | 400 | *0.7* | *25* | | | |
| | 800 | *0.5* | *24* | | | |
| JK061 | 0 | *0.1* | *13* | 125 | 400 | 11 |
| | 100 | *0.5* | *27* | | | |
| | 200 | *0.7* | *32* | | | |
| | 400 | *0.8* | *22* | | | |
| | 800 | *0.7* | *22* | | | |
| | 1200 | *1.0* | *14* | | | |
| | 0 | *0.2* | *12* | | 800 | 14 |
| | 100 | *0.5* | *35* | | | |
| | 200 | *0.6* | *28* | | | |
| | 400 | *0.6* | *21* | | | |
| | 800 | *0.7* | *17* | | | |
| | 1200 | *0.8* | *12* | | | |
| JK060 | 0 | *0.3* | *14* | 56 | 200 | 8 |
| | 100 | *1.0* | *46* | | | |
| | 200 | *1.3* | *35* | | | |
| | 400 | *1.7* | *30* | | | |
| | 800 | *1.5* | *27* | | | |
| | 1200 | *1.9* | *18* | | | |
| | 0 | *0.3* | *11* | | 200 | 8 |
| | 100 | *1.1* | *32* | | | |

TABLE 2-continued

Percentages of the high rFVIIa binding sub-population, and ratios of fluorescence of the high binding versus the main platelet population for all rFVIIa concentrations measured from all donors; non-activated platelets. Values for populations <2% are in italic with grey fillings.

|  | 200 | *1.1* | *28* |  |  |  |
|---|---|---|---|---|---|---|
|  | 400 | *1.3* | *26* |  |  |  |
|  | 800 | *1.5* | *20* |  |  |  |
|  | 1200 | *1.6* | *16* |  |  |  |
| JK059-2 | 0 | *0.7* | *10* | 148 | 400 | 7 |
|  | 100 | *1.2* | *23* |  |  |  |
|  | 200 | *0.9* | *29* |  |  |  |
|  | 400 | *1.0* | *23* |  |  |  |
|  | 800 | *0.8* | *16* |  |  |  |
|  | 1200 | *0.9* | *12* |  |  |  |
|  | 0 | *0.7* | *11* |  | 400 | 8 |
|  | 100 | *0.9* | *24* |  |  |  |
|  | 200 | *0.9* | *30* |  |  |  |
|  | 400 | *0.9* | *22* |  |  |  |
|  | 800 | *0.8* | *16* |  |  |  |
|  | 1200 | *0.8* | *14* |  |  |  |

TABLE 3

Percentages of the high rFVIIa binding sub-population, and ratios of fluorescence of the high binding versus the main platelet population for all rFVIIa concentrations measured from all donors; dual agonist-activated platelets. Values for populations <2% are italic with grey fillings.

| Donor protocol address | rFVIIa conc [nM] | % high rFVIIa binding subpopulation of all platelets | X-fold median fluorescence intensity of high rFVIIa binding population compared to the major population | $K_D$ [nM] | Saturation reached at rFVIIa concentration [nM] | X-fold median fluorescence intensity of all platelets compared to the control w/o rFVIIa at 100 nM |
|---|---|---|---|---|---|---|
| AH163 | 0 | *0.2* | *53* |  | 1000 | 18 |
|  | 100 | 21.0 | 5 |  |  |  |
|  | 200 | 22.5 | 5 |  |  |  |
|  | 400 | 22.2 | 5 |  |  |  |
|  | 800 | 22.6 | 4 |  |  |  |
|  | 1200 | 17.7 | 5 |  |  |  |

TABLE 3-continued

Percentages of the high rFVIIa binding sub-population, and ratios of
fluorescence of the high binding versus the main platelet population for all rFVIIa concentrations
measured from all donors; dual agonist-activated platelets. Values for populations <2% are italic
with grey fillings.

|  |  |  |  |  |  |  |
|---|---|---|---|---|---|---|
|  | 1600 | 16.1 | 4 |  |  |  |
|  | 2000 | 13.7 | 5 |  |  |  |
| AH162 | 0 | *0.2* | *104* |  | 1200 | 12 |
|  | 100 | *1.4* | *9* |  |  |  |
|  | 200 | *1.3* | *10* |  |  |  |
|  | 400 | *1.1* | *13* |  |  |  |
|  | 800 | *1.9* | *8* |  |  |  |
|  | 1200 | 2.5 | 9 |  |  |  |
|  | 1600 | 2.4 | 9 |  |  |  |
|  | 2000 | 3.9 | 9 |  |  |  |
| AH155 | 0 | *0.1* | *58* | 418 | 1000 | 11 |
|  | 100 | 2.3 | 6 |  |  |  |
|  | 200 | 2.0 | 7 |  |  |  |
|  | 400 | 2.5 | 5 |  |  |  |
|  | 800 | 2.9 | 4 |  |  |  |
|  | 1200 | 3.1 | 5 |  |  |  |
|  | 1600 | 3.4 | 5 |  |  |  |
|  | 2000 | 4.1 | 5 |  |  |  |
| AH153 | 0 | *0.2* | *29* | 29 | No | 12 |
|  | 100 | *1.2* | *30* |  | saturation |  |
|  | 300 | *0.9* | *11* |  |  |  |
|  | 900 | *1.4* | *9* |  |  |  |
|  | 1800 | 2.0 | 6 |  |  |  |
| AH148 | 0 | *0.0* | *267* |  | (800) |  |
|  | 800 | *1.3* | *7* |  |  |  |
|  | 1200 | *1.3* | *5* |  |  |  |
|  | 2000 | *1.2* | *6* |  |  |  |
|  | 3000 | *0.7* | *7* |  |  |  |
|  | 4000 | *0.6* | *7* |  |  |  |
| AH146 | 0 | *0.0* | *32* |  | No | 11 |
|  | 100 | 2.4 | 6 |  | saturation |  |
|  | 200 | *1.8* | *5* |  |  |  |
|  | 400 | *1.6* | *5* |  |  |  |
|  | 600 | *1.8* | *4* |  |  |  |
|  | 800 | *1.5* | *6* |  |  |  |
| AH141 | 0 | *0.2* | *15* |  | Not | 7 |
|  | 100 | 3.9 | 8 |  | applicable |  |
|  | 50 | 7.6 | 7 |  | No | 5 |
|  | 100 | 5.9 | 8 |  | saturation |  |
|  | 250 | 6.1 | 10 |  |  |  |
|  | 400 | 5.7 | 11 |  |  |  |
|  | 500 | 5.8 | 13 |  |  |  |
|  | 100 | 4.8 | 7 |  | Not | 6 |
|  |  |  |  |  | applicable |  |
|  | 100 | 4.1 | 6 |  | Not | 6 |
|  |  |  |  |  | applicable |  |
|  | 100 | 5.1 | 6 |  | Not | 6 |

TABLE 3-continued

Percentages of the high rFVIIa binding sub-population, and ratios of fluorescence of the high binding versus the main platelet population for all rFVIIa concentrations measured from all donors; dual agonist-activated platelets. Values for populations <2% are italic with grey fillings.

|  |  |  |  |  |  |  |
|---|---|---|---|---|---|---|
|  |  |  |  |  | applicable |  |
|  | 100 | 5.5 | 7 |  | Not applicable | 6 |
| AH139 | 0 | *0.5* | *13* |  | Not applicable | 9 |
|  | 100 | 7.7 | 5 |  |  |  |
|  | 100 | 4.2 | 5 |  | Not applicable | 10 |
|  | 100 | 5.0 | 5 |  | Not applicable | 8 |
|  | 100 | 8.4 | 4 |  | Not applicable | 8 |
|  | 100 | 6.1 | 6 |  | Not applicable | 7 |
| AH138 | 0 | *0.2* | *16* |  | Not applicable | 6 |
|  | 100 | 3.0 | 14 |  |  |  |
| AH135 | 0 | *0.6* | *21* |  | Not | 11 |
|  | 100 | 2.0 | 18 |  | applicable |  |
|  | 100 | 1.4 | 21 |  | Not applicable | 13 |
|  | 100 | 1.3 | 17 |  | Not applicable | 12 |
|  | 100 | 1.3 | 15 |  | Not applicable | 12 |
|  | 100 | 1.5 | 19 |  | Not applicable | 9 |
| AH134 | 0 | *0.5* | *13* |  | Not applicable | 5 |
|  | 100 | *0.9* | *6* |  |  |  |
|  | 100 | 0.9 | 14 |  | Not applicable | 5 |
| AH132 | 0 | *0.2* | *26* |  | Not | 7 |
|  | 100 | *0.9* | *16* |  | applicable |  |
| JK070 | 0 | *0.1* | *80* |  | 400 | 29 |
|  | 50 | *0.6* | *14* |  |  |  |
|  | 100 | *0.6* | *11* |  |  |  |
|  | 200 | *1.3* | *6* |  |  |  |
|  | 400 | *1.0* | *6* |  |  |  |
|  | 800 | *0.5* | *14* |  |  |  |
|  | 0 | *0.2* | *9* |  | 300 | 24 |
|  | 50 | *0.3* | *12* |  |  |  |
|  | 100 | *0.3* | *17* |  |  |  |
|  | 200 | *0.9* | *5* |  |  |  |
|  | 400 | *1.0* | *7* |  |  |  |
|  | 800 | *0.6* | *11* |  |  |  |

TABLE 3-continued

Percentages of the high rFVIIa binding sub-population, and ratios of fluorescence of the high binding versus the main platelet population for all rFVIIa concentrations measured from all donors; dual agonist-activated platelets. Values for populations <2% are italic with grey fillings.

| | | | | | | |
|---|---|---|---|---|---|---|
| JK069 | 0 | *0.0* | *0* | 302 | 400 | 22 |
| | 50 | *0.2* | *25* | | | |
| | 100 | *0.4* | *9* | | | |
| | 200 | *1.5* | *5* | | | |
| | 400 | 11.0 | 3 | | | |
| | 800 | 24.0 | 3 | | | |
| | 0 | *0.0* | *36* | | 400 | 22 |
| | 50 | *0.1* | *36* | | | |
| | 100 | *0.4* | *14* | | | |
| | 200 | *0.8* | *5* | | | |
| | 400 | 6.3 | 3 | | | |
| | 800 | 13.0 | 3 | | | |
| JK067 | 0 | *0.0* | *9* | | 400 | 15 |
| | 50 | *0.1* | *44* | | | |
| | 100 | *0.2* | *31* | | | |
| | 200 | *0.3* | *16* | | | |
| | 400 | *0.9* | *8* | | | |
| | 800 | *0.5* | *12* | | | |
| | 0 | *0.0* | *9* | | 400 | 15 |
| | 50 | *0.1* | *43* | | | |
| | 100 | *0.2* | *36* | | | |
| | 200 | *0.4* | *12* | | | |
| | 400 | *0.5* | *8* | | | |
| | 800 | *0.3* | *11* | | | |
| JK066 | 0 | *0.2* | *13* | 108 | 400 | 35 |
| | 50 | 2.1 | *5* | | | |
| | 100 | 2.6 | *4* | | | |
| | 200 | 2.6 | *4* | | | |
| | 400 | *1.4* | *5* | | | |
| | 800 | *0.6* | *11* | | | |
| | 0 | *0.2* | *11* | | 400 | 30 |
| | 50 | *1.7* | *4* | | | |
| | 100 | *1.9* | *4* | | | |
| | 200 | 2.2 | 4 | | | |
| | 400 | *1.9* | *4* | | | |
| | 800 | *0.9* | *8* | | | |
| JK065 | 0 | *0.31* | *9* | | 200 | 36 |
| | 50 | *0.87* | *10* | | | |
| | 100 | *0.84* | *9* | | | |
| | 200 | *0.91* | *8* | | | |
| | 400 | *0.67* | *9* | | | |
| | 800 | *0.67* | *14* | | | |
| | 0 | *0.01* | *646* | | 300 | 32 |
| | 50 | *0.48* | *16* | | | |
| | 100 | *0.75* | *10* | | | |
| | 200 | *1* | *6* | | | |
| | 400 | *0.46* | *9* | | | |
| | 800 | *0.64* | *10* | | | |

TABLE 3-continued

Percentages of the high rFVIIa binding sub-population, and ratios of fluorescence of the high binding versus the main platelet population for all rFVIIa concentrations measured from all donors; dual agonist-activated platelets. Values for populations <2% are italic with grey fillings.

| | | | | | | |
|---|---|---|---|---|---|---|
| JK063 | 0 | *1.2* | *12* | 472 | No saturation | 33 |
| | 50 | *0.1* | *50* | | | |
| | 100 | *0.2* | *31* | | | |
| | 200 | *1.2* | *6* | | | |
| | 400 | *1.1* | *5* | | | |
| | 800 | *0.6* | *9* | | | |
| | 0 | *1.5* | *12* | | 800 | 37 |
| | 50 | *0.2* | *21* | | | |
| | 100 | *0.6* | *6* | | | |
| | 200 | *0.8* | *6* | | | |
| | 400 | *0.6* | *6* | | | |
| | 800 | *0.5* | *6* | | | |
| JK062 | 0 | *0.3* | *13* | 1025 | No saturation | 20 |
| | 50 | 3.5 | 5 | | | |
| | 100 | 4.2 | 5 | | | |
| | 200 | 4.0 | 4 | | | |
| | 400 | 4.1 | 4 | | | |
| | 800 | 11.0 | 3 | | | |
| | 0 | *0.4* | *28* | | 800 | 22 |
| | 50 | 2.9 | 4 | | | |
| | 100 | 2.8 | 4 | | | |
| | 200 | 3.8 | 4 | | | |
| | 400 | 4.7 | 3 | | | |
| | 800 | 5.6 | 4 | | | |
| JK061 | 0 | *0.2* | *10* | | 400 | 14 |
| | 100 | 3.0 | 4 | | | |
| | 200 | 2.5 | 5 | | | |
| | 400 | 2.5 | 6 | | | |
| | 800 | 3.1 | 7 | | | |
| | 1200 | 2.2 | 8 | | | |
| | 0 | *0.2* | *11* | | 400 | 12 |
| | 100 | 2.0 | 5 | | | |
| | 200 | 2.4 | 5 | | | |
| | 400 | *1.9* | *6* | | | |
| | 800 | *1.8* | *8* | | | |
| | 1200 | 2.5 | 8 | | | |
| JK060 | 0 | *0.3* | *11* | | 400 | 11 |
| | 100 | 4.2 | 4 | | | |
| | 200 | 5.4 | 4 | | | |
| | 400 | 12.0 | 4 | | | |
| | 800 | 9.7 | 5 | | | |
| | 1200 | 11.0 | 5 | | | |
| | 0 | *0.2* | *12* | | 200 | 11 |
| | 100 | *1.6* | *5* | | | |

TABLE 3-continued

Percentages of the high rFVIIa binding sub-population, and ratios of fluorescence of the high binding versus the main platelet population for all rFVIIa concentrations measured from all donors; dual agonist-activated platelets. Values for populations <2% are italic with grey fillings.

| Donor | Conc. | % | Ratio | | Conc. | Ratio |
|---|---|---|---|---|---|---|
| | 200 | 4.3 | 4 | | | |
| | 400 | 6.1 | 4 | | | |
| | 800 | 5.1 | 5 | | | |
| | 1200 | 6.4 | 4 | | | |
| JK059-2 | 0 | *0.7* | *9* | | 400 | 6 |
| | 100 | 2.7 | 5 | | | |
| | 200 | 2.5 | 6 | | | |
| | 400 | 3.1 | 5 | | | |
| | 800 | 3.7 | 5 | | | |
| | 1200 | 6.8 | 6 | | | |
| | 0 | *0.6* | *9* | | 400 | 8 |
| | 100 | 2.5 | 5 | | | |
| | 200 | 3.3 | 6 | | | |
| | 400 | 2.8 | 5 | | | |
| | 800 | 3.2 | 5 | | | |
| | 1200 | 4.5 | 4 | | | |

TABLE 4

$K_D$ estimations of high rFVIIa binding platelet subpopulations compared to the major populations (populations >2% were included); cut offs: $K_D R^2 > 0.90$. Only activated platelets from some donors fulfilled these criteria.

| | $K_D$ [nM] | |
|---|---|---|
| Donor protocol address | high rFVIIa binding population | Major population |
| JK069 | | 685 |
| JK066 | 200 | 109 |
| JK062 | 554 | 935 |
| AH163 | | 354 |
| AH155 | | 413 |

What is claimed is:

1. A method of treating a bleeding disorder in a subject in need thereof, the method comprising
   a) selecting a subject by (i) incubating a platelet population obtained from the subject with at least 5 nm of rFVIIa and (ii) detecting a subpopulation of platelets comprising at least 1% of the platelet population wherein said platelet subpopulation has at least a 4-fold higher binding capacity to rFVIIa, as compared to the binding capacity to rFVIIa of the other platelets in the platelet population and
   b) administering a therapeutically effective amount of rFVIIa to a subject identified by step (ii).

2. The method of claim 1, wherein the subpopulation of platelets comprises platelets having about a 6-fold higher binding capacity to rFVIIa, as compared to the binding capacity to rFVIIa of the other platelets in the platelet population.

3. The method of claim 1, wherein the bleeding disorder is hemophilia A or hemophilia B.

4. The method of claim 1, wherein the subject is a human.

5. The method of claim 1, wherein the bleeding disorder is a non-hemophilia bleeding disorder and the subject does not have an unacceptable risk of thrombosis.

6. The method of claim 1, wherein the subpopulation of platelets comprises at least 2% of the platelet population.

7. The method of claim 1, wherein the subpopulation of platelets comprises at least 3% of the platelet population.

8. The method of claim 1, wherein the bleeding disorder is congenital hemophilia A with inhibitors or acquired hemophilia A with inhibitory auto an bodies to FVIII.

9. The method of claim 1, wherein the bleeding disorder is congenital hemophilia B with inhibitors or acquired hemophilia B with inhibitory auto antibodies to FIX.

10. The method of claim 1, wherein the bleeding disorder is blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease or von Willebrand disease with inhibitors to von Willebrand factor.

11. The method of claim 1, wherein the platelets in the subpopulation of platelets are activated.

12. The method of claim 1, wherein the platelets in the subpopulation of platelets are non-activated.

13. The method of claim 1, wherein the platelets in the subpopulation of platelets are coated.

14. A method of treating a bleeding disorder in a subject in need thereof, the method comprising
   a) selecting a subject by (i) incubating a platelet population obtained from the subject with at least 5 nm of rFVIIa and (ii) determining that the subject lacks a subpopulation of platelets comprising at least 1% of the platelet population wherein said platelet subpopulation has at least a 4-fold higher binding capacity to rFVIIa, as compared to the binding capacity to rFVIIa of the other platelets in the platelet population, and
   b) administering a therapeutically effective amount of an alternative therapy that does not comprise the administration of rFVIIa to a subject identified by step (ii).

15. The method of claim 14, wherein (ii) comprises determining that the subject lacks a subpopulation of platelets comprising at least 1% of the platelet population wherein said platelet subpopulation has about a 6-fold higher binding capacity to rFVIIa, as compared to the binding capacity to rFVIIa of the other platelets in the platelet population.

16. The method of claim 14, wherein the alternative therapy is Prothrombin Complex Concentrate, activated Prothrombin Complex Concentrate, recombinant Factor IX, recombinant Factor VIII, recombinant anti-hemophilic factor, desmopressin, Factor IX complex, cryoprecipitated anti-hemophilic factor (AHF), fresh frozen plasma (FFP), recombinant porcine FVIII, recombinant FV variants, recombinant FVIIIa variants, recombinant FXa variants, FXIII, prothrombin, fibrinogen, a mix of coagulation factors, antibodies mimicking FVIII, peptides mimicking FVIII, compounds mimicking FVIII, peptide inhibitors of TFPI, antibody inhibitors of TFPI, compounds inhibiting TFPI, or compounds inhibiting anti-coagulant proteins.

17. The method of claim 14, wherein the bleeding disorder is hemophilia A or hemophilia B.

18. The method of claim 14, wherein the subject is a human.

19. The method of claim 14, wherein the bleeding disorder is a non-hemophilia bleeding disorder.

20. A method of treating a bleeding disorder in subject in need thereof, the method comprising
    a) selecting a subject by (i) incubating a platelet population from a subject with at least 5 nm of rFVIIa and (ii) detecting a subpopulation of platelets comprising at least 1% of the platelet population wherein said platelet subpopulation has at least a 3.5 fold higher binding capacity to rFVIIa upon dual activation of the platelet population by two agonists, as compared to the binding capacity to rFVIIa of non-activated platelets obtained from subject, and
    b) administering a therapeutically effective amount of rFVIIa to a subject identified by step (ii).

21. The method of claim 20, wherein the bleeding disorder is hemophilia, blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease or von Willebrand disease with inhibitors to von Willebrand factor.

22. The method of claim 20, wherein the subject is a human.

23. The method of claim 20, wherein the subpopulation of platelets comprises at least 2% of the platelet population.

24. The method of claim 20, wherein the subpopulation of platelets comprises at least 3% of the platelet population.

25. The method of claim 20, wherein the bleeding disorder is congenital hemophilia A with inhibitors or acquired hemophilia A with inhibitory auto antibodies to FVIII.

26. The method of claim 20, wherein the bleeding disorder is congenital hemophilia B with inhibitors or acquired hemophilia B with inhibitory auto antibodies to FIX.

* * * * *